US007700798B1

(12) United States Patent
Davies et al.

(10) Patent No.: US 7,700,798 B1
(45) Date of Patent: Apr. 20, 2010

(54) EROGORGIAENE CONGENERS AND METHODS AND INTERMEDIATES USEFUL IN THE PREPARATION OF SAME

(75) Inventors: Huw M. L. Davies, East Amherst, NY (US); Abbas M. Walji, Pasadena, CA (US)

(73) Assignee: The Research Foundation of State University of New York, Amherst, NY (US)

( * ) Notice: Subject to any disclaimer, the term of this patent is extended or adjusted under 35 U.S.C. 154(b) by 402 days.

(21) Appl. No.: 11/449,143

(22) Filed: Jun. 8, 2006

Related U.S. Application Data

(60) Provisional application No. 60/688,590, filed on Jun. 8, 2005.

(51) Int. Cl.
*C07C 69/76* (2006.01)
(52) U.S. Cl. ....................................................... 560/56
(58) Field of Classification Search .................. None
See application file for complete search history.

(56) References Cited

U.S. PATENT DOCUMENTS

| 2,507,631 | A | 5/1950 | Hartmann et al. |
|---|---|---|---|
| 2,957,880 | A | 10/1960 | Rometsch et al. |
| 4,133,881 | A | 1/1979 | Cale, Jr. et al. |
| 4,238,488 | A | 12/1980 | Howe et al. |
| 4,866,048 | A | 9/1989 | Calverley et al. |
| 5,036,053 | A | 7/1991 | Himmelsbach et al. |
| 5,175,311 | A | 12/1992 | Doyle |
| 5,296,595 | A | 3/1994 | Doyle |
| 5,401,732 | A | 3/1995 | Calverley et al. |
| 5,591,854 | A | 1/1997 | Davies |
| 5,665,890 | A | 9/1997 | Jacobsen et al. |
| 5,760,055 | A | 6/1998 | Davies |
| 6,410,746 | B1 | 6/2002 | Davies |
| 6,762,304 | B2 | 7/2004 | Davies |
| 6,962,891 | B2 | 11/2005 | Davies et al. |
| 7,030,051 | B2 | 4/2006 | Davies |
| 2003/0130112 | A1* | 7/2003 | Davies et al. ................ 502/159 |

FOREIGN PATENT DOCUMENTS

| GB | 2 260 903 A | 5/1993 |
|---|---|---|
| WO | 00/64583 | 11/2000 |

OTHER PUBLICATIONS

Snyder et al., "Oxidative Cleavage of Hydroquinone Ethers with Argentic Oxide," J. Am. Chem. Soc., 94(1):227-231 (1972).
Grieco et al., "Organoselenium Chemistry. A Facile One-Step Synthesis of Alkyl Aryl Selenides from Alcohols," J. Org. Chem., 41(8):1485-1486 (1976).
Adachi et al., "Series of Aromatic Sesquiterpenes. IV. The Synthesis of gamma-Calacorene, Calamenene, and 4-Methoxyisocadalene," Bull. Chem. Soc. Jpn., 56:651-652 (1983).
Davies et al., "Stereoselective Synthesis of Seven-Membered Carbocycles by a Tandem Cyclopropanation/Cope Rearrangement Between Rhodium(II)-Stabilized Vinylcarbenoids and Dienes," J. Org. Chem., 56(12):3817-3824 (1991).
Zubaidha et al., "Synthesis of (±)Heritol," Tetrahedron, 47(30):5759-5768 (1991).
Davies et al., "Highly Stereoselective [3+2] Annulations by Cyclopropanation of Vinyl Ethers with Rhodium (II)-Stabilized Vinylcarbenoids Followed by a Formally Forbidden 1,3-Sigmatropic Rearrangement," J. Org. Chem., 57(11):3186-3190 (1992).
Xu et al., "Enantioselective Total Syntheses and Stereochemical Studies of All Four Stereoisomers of Yingzhaosu C," J. Org. Chem., 60(10):3039-3044 (1995).
Chavan et al., "Enantiospecific Total Synthesis of (+)-Laevigatin," Tetrahedron:Asymmetry, 8(15):2517-2518 (1997).
Corey et al., "A Direct and Efficient Stereocontrolled Synthetic Route to the Pseudopterosins, Potent Marine Antiinflammatory Agents," J. Am. Chem. Soc., 120(49):12777-12782 (1998).
Davies et al., "Asymmetric Catalytic C-H Activation Applied to the Synthesis of Syn-Aldol Products," Org. Lett., 2(26):4153-4156 (2000).
Rodriguez et al., "A Marine Diterpene with a Novel Tetracyclic Framework from the West Indian Gorgonian Octocoral *Pseudopterogorgia elisabethae*," Org. Lett., 2(4):507-510 (2000).
Rodriguez et al., "Novel Terpenoids from the West Indian Sea Whip *Pseudopterogorgia elisabethae* (Bayer). Elisapterosins A and B: Rearranged Diterpenes Possessing an Unprecedented Cagelike Framework," J. Org. Chem., 65(5):1390-1398 (2000).

(Continued)

*Primary Examiner*—Paul A Zucker
(74) *Attorney, Agent, or Firm*—Peter Rogalskyj, Esq

(57) ABSTRACT

Disclosed are compounds having the formula:

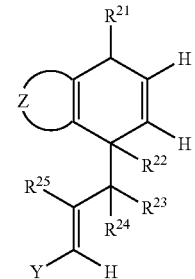

wherein $R^{21}$ is an alkyl, aryl, alkoxy, hydroxy, or amino group or a halogen atom; wherein $R^2$ is hydrogen or an alkyl, aryl, alkoxy, or amino group; wherein $R^{23}$ and $R^{24}$ are independently selected from hydrogen, an alkyl, aryl, alkoxy, hydroxy, or amino group, and a halogen atom or wherein $R^{23}$ and $R^{24}$, taken together with the carbon atom to which they are bound, form a ring; wherein $R^{25}$ is hydrogen, an alkyl, aryl, alkoxy, hydroxy, or O-silyl group or a halogen atom; wherein Z, taken together with the carbons to which it is bonded, forms a 5-12 membered ring; and wherein Y is an electron withdrawing group. These compounds can be used to prepare erogorgiaene congeners, such as erogorgiaene, pseudopterosin A, helioporin E, pseudopteroxazole, colombiasin A, elisapoterosin B, elisabethadione, p-benzoquinone natural products, ileabethin, sinulobtain B, sinulobtain C, and sinulobtain D.

35 Claims, 15 Drawing Sheets

OTHER PUBLICATIONS

Dehmel et al., "Unexpected endo Selectivity of Conjugate Nucleophilic Addition to an Arene-Cr(CO)3 Complex: Enantioselective Synthesis of the Diterpene 11-epi-Helioporin B," Org. Lett., 3(22):3579-3582 (2001).

Ferraz et al., "Thallium Trinitrate-Mediated Ring Contraction of 1,2-dihydronaphthalenes: An Approach to the Synthesis of Indans," Tetrahedron, 57(9):1709-1713 (2001).

Harrowven et al., "Towards Colombiasin A," Tetrahedron Lett., 42(49):8709-8711 (2001).

Johnson et al., "Enantiospecific Synthesis of the Proposed Structure of the Antitubercular Marine Diterpenoid Pseudopteroxazole: Revision of Stereochemistry," J. Am. Chem. Soc., 123(19):4475-4479 (2001).

Nicolaou et al., "Total Synthesis of Colombiasin A," Angew. Chem., Int. Ed., 40(13):2482-2486 (2001).

Nicolaou et al., "Total Synthesis of Colombiasin A and Determination of Its Absolute Configuration," Chem. Eur. J., 7(24):5359-5371 (2001).

Ono et al., "Total Synthesis of (S)-(+)-Curcudiol, and (S)-(+) and (R)-(−)-Curcuphenol," Chem. Pharm. Bull., 49:1581-1585 (2001).

Rodriguez et al., "Serrulatane Diterpenes with Antimycobacterial Activity Isolated from the West Indian Sea Whip *Pseudopterogorgia elisabethae*," J. Nat. Prod., 64(1):100-102 (2001).

Tohma et al., "Novel and Efficient Synthesis of p-Quinones in Water via Oxidative Demethylation of Phenol Ethers Using Hypervalent Iodine(III) Reagents," Tetrahedron Lett., 42(39):6899-6902 (2001).

Chaplin et al., "An Enantioselective Double Diels—Alder Approach to the Tetracyclic Framework of Colombiasin A," Org. Biomol. Chem., 1:1842-1844 (2003).

Davidson et al., "First Enantiospecific Total Synthesis of the Antitubercular Marine Natural Product Pseudopteroxazole. Revision of Assigned Stereochemistry," J. Am. Chem. Soc., 125(44):13486-13489 (2003).

Davies et al., "Catalytic Enantioselective C-H Activation by Means of Metal-Carbenoid-Induced C-H Insertion," Chem. Rev., 103(8):2861-2904 (2003).

Davies et al., "Dirhodium Tetraprolinate-Catalyzed Asymmetric Cyclopropanations with High Turnover Numbers," Org. Lett., 5(9):1403-1406 (2003).

Heckrodt et al., "Total Synthesis of Elisabethin A: Intramolecular Diels-Alder Reaction under Biomimetic Conditions," J. Am. Chem. Soc., 125(16):4680-4681 (2003).

Kim et al., "Unified Strategy for the Synthesis of (−)-Elisapterosin B and (−)-Colombiasin A," Angew. Chem., Int. Ed., 42(11):1267-1270 (2003).

Nowlan et al., "Isotope Effects and the Nature of Selectivity in Rhodium-Catalyzed Cyclopropanations," J. Am. Chem. Soc., 125(51):15902-15911 (2003).

Waizumi et al., "A General Strategy to Elisabethane Diterpenes: Stereocontrolled Synthesis of Elisapterosin B via Oxidative Cyclization of an Elisabethin Precursor," J. Am. Chem. Soc., 125(43):13022-13023 (2003).

Cesati et al., "Enantioselective Total Synthesis of Erogorgiaene: Applications of Asymmetric Cu-Catalyzed Conjugate Additions of Alkylzincs to Acyclic Enones," J. Am. Chem. Soc., 126(1):96-101 (2004).

Davies et al., "Asymmetric Catalysis Special Feature Part I: Catalytic Asymmetric Reactions for Organic Synthesis: The Combined C-H Activation/Cope Rearrangement," Proc. Natl. Acad. Sci. USA, 101(15):5472-5475 (2004).

Davies et al., "Catalytic Asymmetric Reactions for Organic Synthesis: The Combined C-H Activation/Siloxy-Cope Rearrangement," J. Org. Chem., 69(26):9241-9247 (2004).

Davies et al., "Highly Diastereoselective and Enantioselective C-H Functionalization of 1,2-Dihydronaphthalenes: A Combined C-H Activation/Cope Rearrangement Followed by a Retro-Cope Rearrangement," J. Am. Chem. Soc., 126(35):10862-10863 (2004).

Harmata et al., "Benzothiazines in Synthesis. Toward the Synthesis of Pseudopteroxazole," Org. Lett., 6(13):2201-2203 (2004).

Rodriguez et al., "New Pseudopterosin and seco-Pseudopterosin Diterpene Glycosides from Two Colombian Isolates of *Pseudopterogorgia elisabethae* and Their Diverse Biological Activities," J. Nat. Prod., 67(10):1672-1680 (2004).

Zanoni et al., "Elisabethin A: A Marine Diterpenoid Yet To Surrender to Total Synthesis," Angew. Chem., Int. Ed., 43(37):4837-4841 (2004).

Boezio et al., "Efficient Total Syntheses of (−)-Colombiasin A and (−)-Elisapterosin B: Application of the Cr-Catalyzed Asymmetric Quinone Diels-Alder Reaction," Angew. Chem., Int. Ed., 44(37):6046-6050 (2005).

Davies et al., "Direct Synthesis of (+)-Erogorgiaene Through a Kinetic Enantiodifferentiating Step," Angew. Chem. Int. Ed., 44(11):1733-1735 (2005).

Harmata et al., "Benzothiazines in Synthesis. A Total Synthesis of Pseudopteroxazole," Org. Lett., 7(16):3581-3583 (2005).

Harmata et al., "Benzothiazines in Synthesis. Formal Synthesis of Erogorgiaene," Tetrahedron Lett., 46(22):3847-3849 (2005).

Heckrodt et al., "Marine Natural Products from *Pseudopterogorgia elisabethae*: Structures, Biosynthesis, Pharmacology, and Total Synthesis," J. Top. Curr. Chem., 244:1-42 (2005).

Davies et al., "C-H Activation as a Strategic Reaction: Enantioselective Synthesis of 4-Substituted Indoles," J. Am. Chem. Soc., 128:1060-1061 (2006).

Davies et al., "Combined C-H Activation/Cope Rearrangement as a Strategic Reaction in Organic Synthesis: Total Synthesis of (−)-Colombiasin A and (−)-Elisapterosin B," J. Am. Chem. Soc., 128(7):2485-2490 (2006).

* cited by examiner

| Rh(II) | yield, % (6 + 7 + 13) | ratio 6 : 7 : 13 |
|---|---|---|
| $Rh_2(OOct)_4$ | 73 | 3 : 61 : 36 |

22
colombiasin A 23
elisapterosin B (+)-elisabethadione    (+)-p-benzoquinone

EROGORGIAENE CONGENERS AND METHODS AND INTERMEDIATES USEFUL IN THE PREPARATION OF SAME

The present application claims the benefit of U.S. Provisional Patent Application Ser. No. 60/688,590, filed Jun. 8, 2005, which provisional patent application is hereby incorporated by reference.

The present invention was made with the support of the National Science Foundation Contract Nos. CHE0092490 and CHE0350536. The Federal Government may have certain rights in this invention.

FIELD OF THE INVENTION

The present invention relates to diterpenes and to methods and intermediates that can be used to make such diterpenes and, more particularly, to erogorgiaene congeners and to methods and intermediates that can be used to make such erogorgiaene congeners.

BACKGROUND OF THE INVENTION

Natural product synthesis continues to be a fertile area and proving ground for the development of new synthetic methods. On occasion, certain classes of natural products with a rich combination of promising biological activity and intriguing structural architecture become highly attractive synthetic targets.

A class of compounds that is generating much current interest is a super-family of diterpenes, several members of which have been isolated from gorgonian chorals (Heckrodt et al., *J. Topics in Current Chemistry*, 244:1-42 (2005); Coleman et al., *Tetrahedron*, 56:9569-9574 (2000); Rodriguez et al., *Org. Lett.*, 2:507-510 (2000); Nicolaou et al., *Angew. Chem., Int. Ed.*, 40:2482-2486 (2001); Nicolaou et al., *Chem. Eur. J.*, 7:5359-5371 (2001); Kim et al., *Angew. Chem. Int. Ed.*, 42:1267-1270 (2003); Harrowven et al., *Angew. Chem., Int. Ed.*, 44:1221-1222 (2005); Boezio et al., *Angew. Chem., Int. Ed.*, 44:6046-6050 (2005); Harrowven et al., *Tetrahedron Lett.*, 42:8709-8711 (2001); Chaplin et al., *Org. Biomol. Chem.*, 1:1842-1844 (2003); Rodriguez et al., *J. Org. Chem.*, 65:1390-1398 (2000); Waizumi et al., *J. Am. Chem. Soc.*, 125:13022-13023 (2003); Rodriguez et al., *Nat. Prod.*, 64:100-102 (2001); Cesati et al., *J. Am. Chem. Soc.*, 126:96-101 (2004); Davies et al., *Angew. Chem., Int. Ed.*, 44:1733-1735 (2005); Harmata et al., *Tetrahedron Lett.*, 46:3847-3849 (2005); Heckrodt et al., *J. Am. Chem. Soc.*, 125:4680-4681 (2003); Zanoni et al., *Angew. Chem., Int. Ed.*, 43:4837-4841 (2004); Johnson et al., *J. Am. Chem. Soc.*, 123:4475-4479 (2001); Davidson et al., *J. Am. Chem. Soc.*, 125:13486-13489 (2003); Harmata et al., *Org. Lett.*, 6:2201-2203 (2004); Harmata et al., *Org. Lett.*, 7:3581-3583 (2005), which are hereby incorporated by reference.

For example, this diverse family of diterpenes can contain from bicyclic to hexacyclic systems, and a large number are derived biosynthetically from elisabethatriene. Examples of these natural products are (−)-colombiasin A, (−)-elisapterosin B, and (+)-erogorgiaene. Many members of this super-family display substantial biological activity as anti-inflammatory, anticancer, antitubercular, and/or general antibacterial agents (Rodriguez et al., *J. Nat. Prod.*, 67:1672-1680 (2004), which is hereby incorporated by reference). Due to the common biosynthetic ancestry of these natural products, all of these natural products have three distinctive stereocenters. As some of the above-cited references evidence, from a synthetic perspective, these three stereocenters have represented considerable challenges because there are no convenient neighboring functional groups available to assist in their stereocontrol.

A need continues to exist for synthetic methods for the preparation of erogorgiaene, colombiasin A, elisapterosin B, and other erogorgiaene congeners, and for intermediates useful in such methods. The present invention is directed to addressing this need.

SUMMARY OF THE INVENTION

The present invention relates to a compound having the formula:

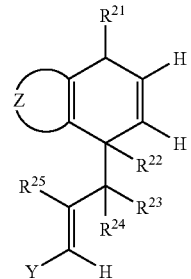

wherein $R^{21}$ is an alkyl group, an aryl group, an alkoxy group, a hydroxy group, an amino group, or a halogen atom; wherein $R^2$ is hydrogen atom, an alkyl group, an aryl group, an alkoxy group, or an amino group; wherein $R^{23}$ and $R^{24}$ are independently selected from a hydrogen atom, an alkyl group, an aryl group, an alkoxy group, a hydroxy group, an amino group, and a halogen atom or wherein $R^{23}$ and $R^{24}$, taken together with the carbon atom to which they are bound, form a ring; wherein $R^{25}$ is a hydrogen atom, an alkyl group, an aryl group, an alkoxy group, a hydroxy group, an O-silyl group, or a halogen atom; wherein Z, taken together with the carbons to which it is bonded, forms a 5-12 membered ring; and wherein Y is an electron withdrawing group.

The present invention also relates to a method for preparing a compound having the formula:

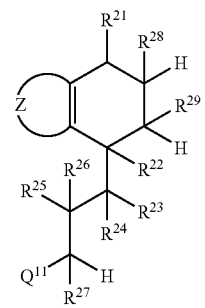

wherein $R^{21}$ is an alkyl group, an aryl group, an alkoxy group, a hydroxy group, an amino group, or a halogen atom; wherein $R^{22}$ is hydrogen atom, an alkyl group, an aryl group, an alkoxy group, or an amino group; wherein $R^{23}$ and $R^{24}$ are independently selected from a hydrogen atom, an alkyl group, an aryl group, an alkoxy group, a hydroxy group, an amino group, and a halogen atom or wherein $R^{23}$ and $R^{24}$, taken together with the carbon atom to which they are bound, form a ring; wherein $R^{25}$ is a hydrogen atom, an alkyl group, an aryl group, an alkoxy group, a hydroxy group, an O-silyl group, or a halogen atom; wherein Z, taken together with the carbons to which it is bonded, forms a 5-12 membered ring; wherein $Q^{11}$ is Y or an alkyl group; wherein each of $R^{21}$ and $R^{27}$ is a hydrogen atom or wherein $R^{26}$ and $R^{27}$, taken together, represent a second bond between the carbon atoms to which $R^{26}$ and $R^{27}$ are bonded; wherein each of $R^{28}$ and $R^{29}$ is a hydrogen atom or wherein $R^{28}$ and $R^{29}$, taken together, represent a second bond between the carbon atoms to which $R^{28}$ and $R^{29}$ are bonded; and wherein Y is an electron withdrawing group. The method includes providing a cyclohexene compound and providing a vinyldiazo compound. The method further includes contacting the cyclohexene compound with a vinyldiazo compound in the presence of a dirhodium catalyst under conditions effective to produce a compound having the following formula:

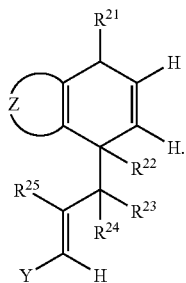

Optionally, this compound can be contacted with a reducing agent under conditions effective to reduce the ring double bond between the carbons to which Z is not bonded, to reduce the double bond between the carbons to which $R^{25}$ and Y are bonded, and/or to reduce Y.

DETAILED DESCRIPTION OF THE INVENTION

Figure 1:
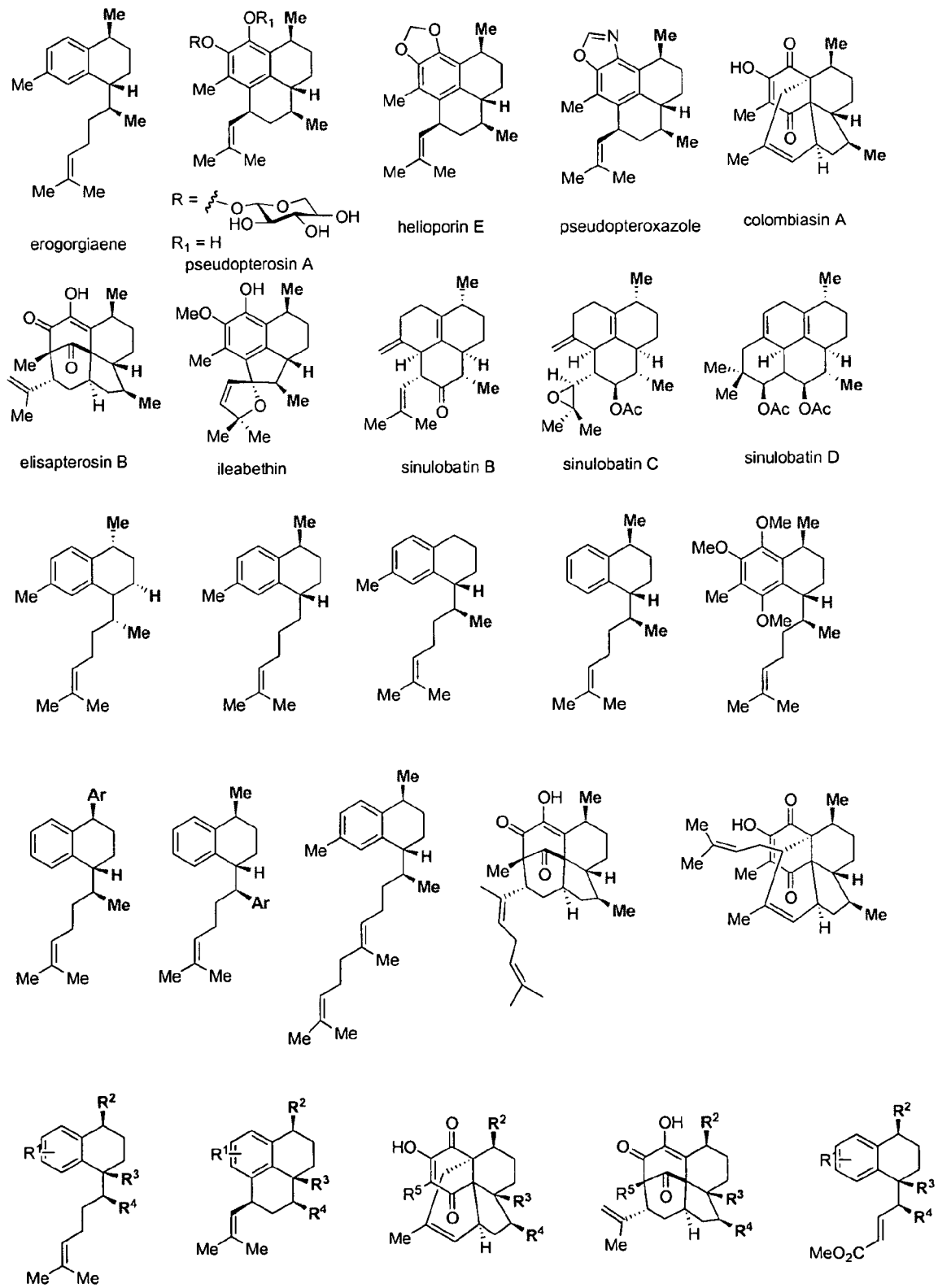
FIG. 1 is a series of chemical formulae of various erogorgiaene congeners that can be prepared using compounds and methods of the present invention.

The present invention, in one aspect thereof, relates to a compound having the formula ("Formula XXI"):

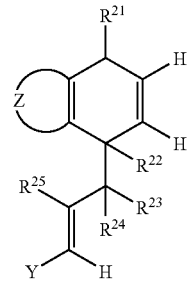

wherein $R^{21}$ is an alkyl group, an aryl group, an alkoxy group, a hydroxy group, an amino group, or a halogen atom; wherein $R^2$ is hydrogen atom, an alkyl group, an aryl group, an alkoxy group, or an amino group; wherein $R^{23}$ and $R^{24}$ are independently selected from a hydrogen atom, an alkyl group, an aryl group, an alkoxy group, a hydroxy group, an amino group, and a halogen atom or wherein $R^{23}$ and $R^{24}$, taken together with the carbon atom to which they are bound, form a ring; wherein $R^{25}$ is a hydrogen atom, an alkyl group, an aryl group, an alkoxy group, a hydroxy group, an O-silyl group, or a halogen atom; wherein Z, taken together with the carbons to which it is bonded, forms a 5-12 membered ring; and wherein Y is an electron withdrawing group.

As used herein, "alkyl" is meant to include linear alkyls, branched alkyls, and cycloalkyls, each of which can be substituted or unsubstituted. "Alkyl" is also meant to include lower linear alkyls (e.g., C1-C6 linear alkyls), such as methyl, ethyl, n-propyl, n-butyl, n-pentyl, and n-hexyl; lower branched alkyls (e.g., C3-C8 branched alkyls), such as isopropyl, t-butyl, 1-methylpropyl, 2-methylpropyl, 1-methylbutyl, 2-methylbutyl, 3-methylbutyl, 1,2-dimethylpropyl, 1,1-dimethylpropyl, 2,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 2-methyl-2-ethylpropyl, 2-methyl-1-ethylpropyl, and the like; and lower cycloalkyls (e.g., C3-C8 cycloalkyls), such as cyclopropyl, cyclobutyl, cyclopentyl, cyclohexyl, and the like. "Alkyl", as use herein, is meant to include unsubstituted alkyls, such as those set forth above, in which no atoms other than carbon and hydrogen are present. "Alkyl", as use herein, is also meant to include substituted alkyls. Suitable substituents include aryl groups (which may themselves be substituted), heterocyclic rings (saturated or unsaturated and optionally substituted), alkoxy groups (which is meant to include aryloxy groups (e.g., phenoxy groups)), amine groups (e.g., disubstituted with aryl or alkyl groups), carboxylic acid derivatives (e.g., carboxylic acid esters, amides, etc.), halogen atoms (e.g., Cl, Br, and I), and the like. Further, alkyl groups bearing one or more alkenyl or alkynyl substituents (e.g., a methyl group itself substituted with a prop-1-en-1-yl group to produce a but-2-en-1-yl substituent) is meant to be included in the meaning of "alkyl". Other suitable substituents include hydroxy groups and protected hydroxy groups (e.g., an acyloxy group, such at an acetoxy group; a silyl ether group, such as a trimethylsilyl ("TMS") ether group and a tert-butyldimethylsilyl ("TBS") ether group).

As used herein, "alkoxy" is meant to include groups having the formula —O—R, where R is an alkyl or aryl group. They include methoxy, ethoxy, propoxy, phenoxy, 4-methylphenoxy, and the like.

As used herein, "aryl" is meant to include aromatic rings, for example, aromatic rings having from 4 to 12 members, such as phenyl rings. These aromatic rings can optionally contain one or more heteroatoms (e.g., one or more of N, O, and S), and, thus, "aryl", as used herein, is meant to include heteroaryl moieties, such as pyridyl rings and furanyl rings. The aromatic rings can be optionally substituted. "Aryl" is also meant to include aromatic rings to which are fused one or more other aryl rings or non-aryl rings. For example, naphthyl groups, indole groups, and 5,6,7,8-tetrahydro-2-naphthyl groups (each of which can be optionally substituted) are aryl groups for the purposes of the present application. As indicated above, the aryl rings can be optionally substituted. Suitable substituents include alkyl groups (which can optionally be substituted), other aryl groups (which may themselves be substituted), heterocyclic rings (saturated or unsaturated), alkoxy groups (which is meant to include aryloxy groups (e.g., phenoxy groups)), amine groups (e.g., disubstituted with aryl or alkyl groups), carboxylic acid groups, carboxylic acid derivatives (e.g., carboxylic acid esters, amides, etc.), halogen atoms (e.g., Cl, Br, and I), and the like.

As used herein, "ring" refers to a homocyclic or heterocyclic ring which can be saturated or unsaturated, aromatic or non-aromatic. The ring can be unsubstituted, or it can be substituted with one or more substituents. The substituents can be saturated or unsaturated, aromatic or nonaromatic, and examples of suitable substituents include those recited above in the discussion relating to substituents on alkyl and aryl groups. Furthermore, two or more ring substituents can combine to form another ring, so that "ring", as used herein, is meant to include fused ring systems. In the case where the ring is saturated (i.e., in the case where each of the atoms making up the ring are joined by single bonds to other members of the ring), the ring may optionally include unsaturated (aromatic or nonaromatic) or saturated substituents.

In certain embodiments, the compound of the present invention has the formula ("Formula XXII"):

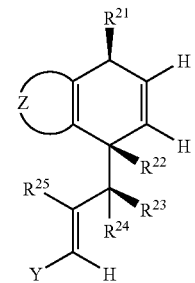

In other embodiments, the compound of the present invention has the formula ("Formula XXIII"):

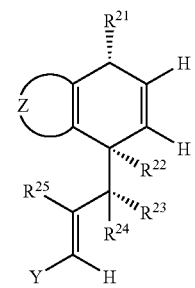

In certain other embodiments, the compound of the present invention is present as a mixture of compounds having Formula XXII and Formula XXIII.

In each of Formulae XXI, XXII, and XXII, $R^{21}$ can be a methyl group. Additionally or alternatively, $R^{22}$ can be a hydrogen atom. Still additionally or alternatively, $R^{23}$ can be a methyl group and/or $R^{24}$ can be a hydrogen atom. For example, In certain embodiments, $R^{21}$ is a methyl group, $R^{22}$ is a hydrogen atom, $R^{23}$ is a methyl group, and $R^{24}$ is a hydrogen atom. As further illustration, each of $R^{23}$ and $R^{24}$ can combine with the carbon atom to which they are bound to form a ring such as a saturated or unsaturated, heterocyclic or homocyclic, substituted or unsubstituted ring (e.g., a C5-C6 saturated or unsaturated, substituted or unsubstituted ring).

As discussed above, n certain embodiments, Z, taken together with the carbons to which it is bonded, forms a ring. The ring can be aromatic or non-aromatic, heterocyclic or homocyclic, substituted or unsubstituted. The ring can be a ring system, such as in the case where two or more rings are fused together, and these ring systems can be bridged or not. The aforementioned rings (or ring systems) can contain any suitable number of members, such as from 5 to 40 members, e.g., from 5 to 20 members, from 5 to 15 members, from 5 to 12 members, from 5 to 10 members, from 5-8 members, and/or from 5 to 6 members. In one illustrative embodiment, Z, taken together with the carbons to which it is bonded, forms a C5-C12 substituted or unsubstituted ring. For example, Z, taken together with the carbons to which it is bonded, can form a C5-C12 substituted or unsubstituted ring, such as in the case where Z, taken together with the carbons to which it is bonded, forms a C6 substituted or unsubstituted ring aromatic ring.

Illustratively, the compound of the present invention can have the formula ("Formula XXIV"):

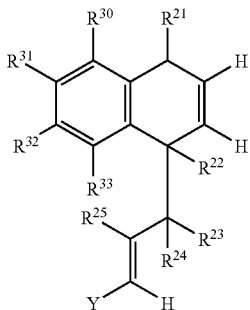

wherein $R^{30}$, $R^{31}$, $R^{32}$, and $R^{33}$ are independently selected from a hydrogen atom, an alkyl group, an aryl group, an alkoxy group, a hydroxy group, a protected hydroxy group (e.g., an acyloxy group, such at an acetoxy group; a silyl ether group, such as a trimethylsilyl ("TMS") ether group and a tert-butyldimethylsilyl ("TBS") ether group); an amino group, a halogen atom, a carboxylic acid group, a carboxylic amide group, carboxylic ester group, a nitro group, a sulfonic acid group, a sulfonamide group, a sulfonic ester group, a keto group, and an aldehyde group. Alternatively, two of $R^{30}$, $R^{31}$, $R^{32}$, and $R^{33}$ (e.g., $R^{30}$ and $R^{31}$, or $R^{31}$ and $R^{32}$ or $R^{32}$ and $R^{33}$) taken together with the carbon atoms to which they are bonded, can form a 5-12 (e.g., a 5-10, 5-8, and/or 5-6) membered ring, and this ring can be aromatic or non-aromatic, homocyclic or heterocyclic, and substituted or unsubstituted.

In certain embodiments, $R^{30}$, $R^{31}$, $R^{32}$, and $R^{33}$ are independently selected from a hydrogen atom, an alkyl group, an aryl group, and an alkoxy group. In certain other embodiments, $R^{30}$, $R^{31}$, $R^{32}$, and $R^{33}$ are independently selected from a hydrogen atom, an alkyl group, an aryl group, a protected hydroxy group, and an alkoxy group. In certain other embodiments, $R^{30}$, $R^{31}$, $R^{32}$, and $R^{33}$ are independently selected from a hydrogen atom, an alkyl group, an aryl group, an acyloxy group, a silyl ether group, and an alkoxy group. In certain other embodiments, $R^{30}$, $R^{31}$, $R^{32}$, and $R^{33}$ are independently selected from a hydrogen atom, an alkyl group, and an alkoxy group. In certain other embodiments, $R^{30}$, $R^{31}$, $R^{32}$, and $R^{33}$ are independently selected from a hydrogen atom, an alkyl group, a protected hydroxy group, and an alkoxy group. In certain other embodiments, $R^{30}$, $R^{31}$, $R^{32}$, and $R^{33}$ are independently selected from a hydrogen atom, an alkyl group, an acyloxy group, a silyl ether group, and an alkoxy group.

The following particular combinations of $R^{30}$, $R^{31}$, $R^{32}$, and $R^{33}$ are set forth to further illustrate certain embodiments of the present invention. In some embodiments, $R^{30}$ is an alkoxy group, $R^{31}$ is an alkoxy group, $R^{32}$ is an alkyl group, and $R^{33}$ is a hydrogen atom. In other embodiments, $R^{30}$ is a methoxy group, $R^{31}$ is a methoxy group, $R^{32}$ is a methyl group, and $R^{33}$ is a hydrogen atom. In still other embodiments, $R^{30}$ is an alkoxy group, $R^{31}$ is an alkoxy group, $R^{32}$ is an alkyl group, and $R^{33}$ is an alkoxy group. In yet other embodiments, $R^{30}$ is a methoxy group, $R^{31}$ is a methoxy group, $R^{32}$ is a methyl group, and $R^{33}$ is a methoxy group. In still other embodiments, $R^{30}$ is a hydrogen atom, $R^{31}$ is a hydrogen atom, $R^{32}$ is an alkyl group, and $R^{33}$ is a hydrogen atom. In yet other embodiments, $R^{30}$ is a hydrogen atom, $R^{31}$ is a hydrogen atom, $R^{32}$ is a methyl group, and $R^{33}$ is a hydrogen atom. In still other embodiments, $R^{30}$ is a protected hydroxy group, $R^{31}$ is an alkoxy group, $R^{32}$ is an alkyl group, and wherein $R^{33}$ is a hydroxy group. In yet other embodiments, $R^{30}$ is an acyloxy group, $R^{31}$ is a methoxy group, $R^{32}$ is a methyl group, and $R^{33}$ is an acyloxy group. In still other embodiments, $R^{30}$ is a silyl ether group, $R^{31}$ is a methoxy group, $R^{32}$ is a methyl group, and $R^{33}$ is a silyl ether group. Illustratively, in Formula XXIV and in each of the aforementioned embodiments, each of $R^{21}$ and $R^{23}$ can be an alkyl group, and each of $R^{22}$, $R^{24}$, and $R^{25}$ can be a hydrogen atom. As further illustration, in Formula XXIV and in each of the aforementioned embodiments, each of $R^{21}$ and $R^{23}$ can be a methyl group, and each of $R^{22}$, $R^{24}$, and $R^{25}$ can be a hydrogen atom.

The aforementioned compounds of the present invention can be prepared by the method described below, to which method the present invention also relates.

The present invention also relates to a method for preparing a compound having the formula:

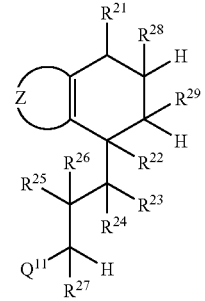

wherein $R^{21}$ is an alkyl group, an aryl group, an alkoxy group, a hydroxy group, an amino group, or a halogen atom; wherein $R^{22}$ is hydrogen atom, an alkyl group, an aryl group, an alkoxy group, or an amino group; wherein $R^{23}$ and $R^{24}$ are independently selected from a hydrogen atom, an alkyl group, an aryl group, an alkoxy group, a hydroxy group, an amino group, and a halogen atom or wherein $R^{23}$ and $R^{24}$, taken together with the carbon atom to which they are bound, form a ring; wherein $R^{25}$ is a hydrogen atom, an alkyl group, an aryl group, an alkoxy group, a hydroxy group, an O-silyl group, or a halogen atom; wherein Z, taken together with the carbons to which it is bonded, forms a 5-12 membered ring; wherein $Q^{11}$ is Y or an alkyl group; wherein each of $R^{26}$ and $R^{27}$ is a hydrogen atom or wherein $R^{26}$ and $R^{27}$, taken together, represent a second bond between the carbon atoms to which $R^{26}$ and $R^{27}$ are bonded; wherein each of $R^{28}$ and $R^{29}$ is a hydrogen atom or wherein $R^{28}$ and $R^{29}$, taken together, represent a second bond between the carbon atoms to which $R^{28}$ and $R^{29}$ are bonded; and wherein Y is an electron withdrawing group.

Specific examples of $R^{21}$, $R^{22}R^{23}R^{24}R^{25}$, Z, and Y include those discussed above in the context of the compounds of the present invention.

In certain embodiments, $R^{28}$ and $R^{29}$, taken together, represent a second bond between the carbon atoms to which $R^{28}$ and $R^{29}$ are bonded; $R^{26}$ and $R^{27}$, taken together, represent a second bond between the carbon atoms to which $R^{26}$ and $R^{27}$ are bonded; and $Q^{11}$ is Y. In such embodiments, the method of the present invention can be used to prepare compounds of Formula XXI. In other embodiments, $R^{28}$ and $R^{29}$ are hydrogen atoms, $R^{26}$ and $R^{27}$ are hydrogen atoms, and/or $Q^{11}$ an alkyl group (e.g., a hydroxymethyl group).

The method includes providing a cyclohexene compound; providing a vinyldiazo compound; and contacting the cyclohexene compound with a vinyldiazo compound in the presence of a dirhodium catalyst under conditions effective to produce a compound having Formula XXI. The method further includes optionally treating the compound of Formula XXI with a reducing agent under conditions effective to reduce the ring double bond between the carbons to which Z is not bonded, to reduce the double bond between the carbons to which $R^{25}$ and Y are bonded, and/or to reduce Y.

Suitable cyclohexene compounds that can be used in the practice of the method of the present invention include those having the formula:

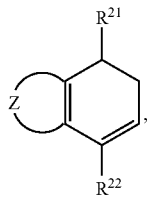

as in the case where the cyclohexene compound has either of the following formulae:

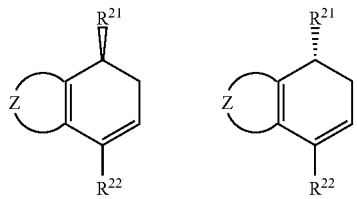

or is a mixture of cyclohexene compounds having such formulae. Illustratively, the cyclohexene compound used in the practice of the method of the present invention can be a racemic mixture having the formula:

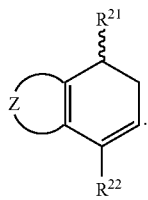

In each of the aforementioned cyclohexene compound formulae, suitable values for $R^{21}$, $R^{22}$, and Z include those set forth above. Illustratively, suitable cyclohexene compounds that can be used in the practice of the method of the present invention include those having the formula:

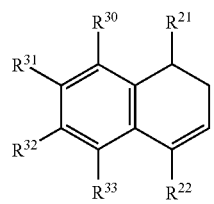

where each of $R^{30}$, $R^{31}$, $R^{32}$, and $R^{33}$ are as described above and where suitable particular combinations of $R^{21}$, $R^{22}$, $R^{30}$, $R^{31}$, $R^{32}$, and $R^{33}$ include those described above.

Suitable vinyldiazo compounds that can be used in the practice of the method of the present invention include those having the formula

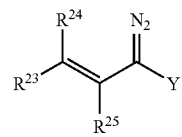

where each of $R^{23}$, $R^{24}$, and $R^{25}$ are as described above.

As discussed above, the method also includes contacting the cyclohexene compound with the vinyldiazo compound in the presence of a dirhodium catalyst under conditions effective to produce a compound having Formula XXI.

As used herein, "dirhodium catalyst" is meant to include any material which is or can be used as a catalyst which contains two rhodium atoms and/or ions that are bonded with one another. The nature of the bond is not limitative: it can be covalent, ionic, van der Walls, pi-pi, sigma-pi, etc., or combinations of these. Of course, the dirhodium catalyst can include other atoms or ions or groups of atoms (e.g., ligands). "Dirhodium catalyst" is also meant to include dirhodium or dirhodium-containing compounds that are attached to surfaces, such as dirhodium complexes which contain one or more ligands that is or are bonded (directly or indirectly) to a surface. Illustratively, each rhodium in the dirhodium catalyst can have a formal charge of +2, and the charge on the overall complex can be neutral.

Examples of suitable dirhodium catalysts include catalysts having the formula $L_4Rh$—$RhL_4$ where each of the L's is the same or different and represents a coordinating atom from one or more ligands.

For example, the dirhodium catalyst can be a dirhodium tetracarboxylate catalyst (i.e., a catalyst having the formula $L_4Rh$—$RhL_4$ where each of the L's represents a carboxylate oxygen from one of four carboxylate groups.

Examples of dirhodium tetracarboxylate catalysts include dirhodium acetate dimer, dirhodium propionate dimer, dirhodium butyrate dimer, dirhodium pentanoate dimer, dirhodium hexanoate dimer, dirhodium heptanoate dimer, dirhodium octanoate dimer, fluorinated analogs thereof (e.g. dirhodium heptafluorobutyrate dimer), and combinations thereof.

Other illustrative examples of dirhodium tetracarboxylate catalysts include those having the formula ("Formula I"):

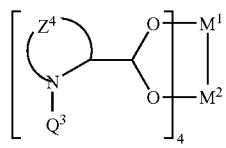

In Formula I, each of $M^1$ and $M^2$ is Rh. $Z^4$ represents the atoms necessary to complete a 3-12 membered heterocyclic ring, such as an alkylene moiety (e.g., a —$CH_2CH_2CH_2$-moiety). $Q^3$ is an electron withdrawing group, such as a group having the formulae —$C(O)R^9$, —$SO_2R^9$, or —$P(O)R^9R^{9'}$, where each of $R^9$ and $R^{9'}$ is independently selected from an alkyl group, an aryl group, and an alkoxy group.

As used herein, "electron withdrawing group" refers to those groups which are able to withdraw electron density from adjacent positions in a molecule, as determined, for example, by reference to the tables in the classical works which establish the classification of various substituents according to their electron withdrawing character. For example, reference may be made to the classification established by the Hammett scale, such as the one set forth in Gordon et al., *The Chemist's Companion*, New York: John Wiley & Sons, pp. 145-147 (1972) ("Gordon"), which is hereby incorporated by reference. Suitable electron-withdrawing groups include those having a para σ value higher than or equal to about 0.2 or higher than or equal to about 0.3, with reference to the Hammett scale. Illustratively, suitable electron withdrawing groups include esters, amides, ketones, phosphonates, sulfonates, sulfones, nitro, trifluoromethyl groups and other perfluorinated alkyl groups, and the like. Particular examples of electron withdrawing groups are moieties having the formulae —$C(O)R$, —$SO_2R$, and —$P(O)RR'$, where R and R' are independently selected from an alkyl group, an aryl group, and an alkoxy group.

As used herein, "alkylene" refers to a bivalent alkyl group, where alkyl has the meaning given above. Linear, branched, and cyclic alkylenes, as well as examples thereof, are defined in similar fashion with reference to their corresponding alkyl group. Examples of alkylenes include eth-1,1-diyl (i.e., —CH(CH₃)—), eth-1,2-diyl (i.e., —CH₂CH₂—), prop-1,1-diyl (i.e., —CH(CH₂CH₃)—), prop-1,2-diyl (i.e., —CH₂—CH(CH₃)—), prop-1,3-diyl (i.e., —CH₂CH₂CH₂—), prop-2,2-diyl (e.g. —C(CH₃)₂—), cycloprop-1,1-diyl, cycloprop-1,2-diyl, cyclopent-1,1-diyl, cyclopent-1,2-diyl, cyclopent-1,3-diyl, cyclohex-1,1-diyl, cyclohex-1,2-diyl, cyclohex-1,3-diyl, cyclohex-1,4-diyl, but-2-en-1,1-diyl, cyclohex-1,3-diyl, but-2-en-1,4-diyl, but-2-en-1,2-diyl, but-2-en-1,3-diyl, but-2-en-2,3-diyl. Also included in the meaning of the term "alkylene" are compounds having the formula —R'—R"—, where —R' represents a linear or branched alkyl group and R"— represents a cycloalkyl group, such as moieties having the formula:

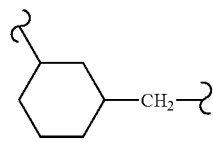

In Formula I and in all other formulae set forth in this document which contain one or more chiral centers and which do not specify the stereochemistry of a particular chiral center, such formulae are to be construed as encompassing all possible stereochemistries. Thus, for example, Formula I is meant to include (i) compounds in which the unspecified chiral center is entirely in the R configuration, (ii) compounds in which the unspecified chiral center is entirely in the S configuration, and (iii) racemic and other mixtures of (i) and (ii). Illustratively, dirhodium tetracarboxylate catalysts of Formula I are meant to include substantially chirally pure catalysts having one of the following formulae ("Formula II-A" and "Formula II-B", respectively):

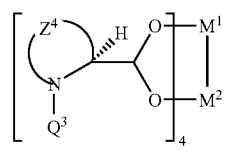 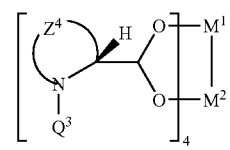

as well as dirhodium tetracarboxylate catalysts of Formula I having $D_2$ symmetry. Molecules having $D_2$ symmetry are molecules which have a vertical $C_2$ axis and a set of two $C_2$ axes perpendicular to the vertical $C_2$ axis. $D_2$ symmetry is further described in, for example, Cotton et al., *Advanced Inorganic Chemistry*, 4th ed., New York: John Wiley & Sons, pages 28-46 (1980), which is hereby incorporated by reference.

Specific examples of suitable catalysts having Formulae I and II include: $Rh_2(DOSP)_4$, $Rh_2(S\text{-}DOSP)_4$, and $Rh_2(R\text{-}DOSP)_4$, which are compounds having Formulae I, II-A, and II-B, respectively, in which each of $M^1$ and $M^2$ is Rh, $Z^4$ is a —$CH_2CH_2CH_2$— group, and $Q^3$ represents a 4-dodecylphenylsulfonyl moiety; and $Rh_2(TBSP)_4$, $Rh_2(S\text{-}TBSP)_4$, and $Rh_2(R\text{-}TBSP)_4$, which are compounds having Formulae I, II-A, and II-B, respectively, in which each of $M^1$ and $M^2$ is Rh, $Z^4$ is a —$CH_2CH_2CH_2$— group, and $Q^3$ represents a 4-t-butylphenylsulfonyl moiety. These and other illustrative compounds having Formulae I, II-A, and II-B are described in greater detail in Davies, "Rhodium-Stabilized Vinylcarbenoid Intermediates in Organic Synthesis," *Current Organic Chemistry*, 2:463-488 (1998), which is hereby incorporated by reference.

Other suitable dirhodium tetracarboxylate catalysts include those which contain two rhodium atoms or ions that are bonded to one another along an axis. This can be represented by the formula Rh—Rh, where the dash represents the bond and the bond axis. These catalysts also contain two carboxylate ligands. As used herein, "carboxylate ligands" means ligands which contain one or more carboxylate groups. As used herein, carboxylate groups mean groups having the formula:

which can be written with the following formula:

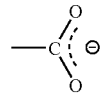

where the dashed line represents the delocalized electrons. Alternatively, the carboxylate group can be expressed without showing the delocalized electrons, as in the following formula:

Each of the two carboxylate ligands includes two carboxylate groups, and these two carboxylate groups are bonded to each other via a moiety having the formula ("Formula III"):

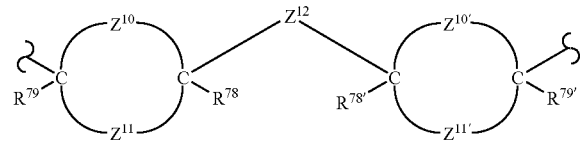

In Formula III, $Z^{10}$ and $Z^{11}$, together with the atoms to which they are bonded form a 3-12 membered ring, and $Z^{10'}$ and $Z^{11'}$, together with the atoms to which they are bonded form a 3-12 membered ring. $Z^{10}$ and $Z^{10'}$ can be the same, and each can contain a heteroatom, such as a nitrogen, oxygen, or sulfur. For example in one embodiment, $Z^{10}$ and $Z^{10'}$ are the same, and each represents a single heteroatom selected from the group consisting a sulfur atom, an oxygen atom, and an optionally substituted nitrogen atom. In another illustrative embodiment, at least one of $Z^{10}$ and $Z^{10'}$ has the formula —NQ-, at least one of $Z^{11}$ and $Z^{11'}$ is an arylene or alkylene group, and Q is an electron withdrawing group. In yet another illustrative embodiment, each of $Z^{10}$ and $Z^{10'}$ has the formula —NQ-, each of $Z^{11}$ and $Z^{11'}$ is an alkylene group, and Q is an electron withdrawing group. Although one of $Z^{10}$ and $Z^{11}$ and/or one of $Z^{11}$ and $Z^{11'}$ can represent a direct bond between the carbons to which they are attached, this need not be the case, for example as when only three, only two, only one, or none of $Z^{10}$, $Z^{11}$, $Z^{10'}$, and $Z^{11'}$ represents such a direct bond. $R^{78}$, $R^{78'}$, $R^{79}$, and $R^{79'}$ are independently selected from the group consisting of H, an alkyl group, and an aryl group, such as in the case where each of $R^{78}$, $R^{78'}$, $R^{79}$, and $R^{79'}$ represents a hydrogen. $Z^{12}$ represents an alkylene or arylene group, such as a substituted or unsubstituted 1,3-phenylene group.

As indicated in the formulae above, each of the two carboxylate groups includes a first carboxylate oxygen atom ("$O^1$"), a second carboxylate oxygen atom ("$O_2$"), and a carbon ("C") to which the $O^1$ and the $O^2$ are bonded thereby forming two $O^1$—C—$O^2$ moieties. $O^1$ of each of the two carboxylate groups of each of the two carboxylate ligands is bonded to the first rhodium ($Rh^1$); $O_2$ of each of the two carboxylate groups of each of the two carboxylate ligands is bonded to the second rhodium ($Rh^2$).

Each of the two carboxylate ligands further includes at least two stereocenters. These stereocenters, for example, can be included in one or more of $Z^{10}$, $Z^{11}$, $Z^{10'}$, and $Z^{11'}$, and/or they can be located at the carbon atoms to which $Z^{10}$, $Z^{11}$, $Z^{10'}$, and $Z^{11'}$ are bonded. The stereochemistry at these stereocenters are selected such that the catalyst, taken as a whole, has $D_2$ symmetry.

Illustrative examples of such dirhodium tetracarboxylate catalysts include those having the formula ("Formula IV"):

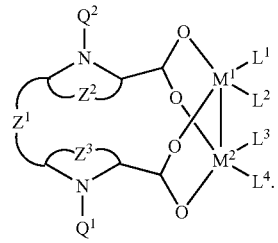

In Formula IV, $M^1$ and $M^2$ represent rhodium atoms or ions. $Z^2$ and $Z^3$, independently, are the atoms necessary to complete a 3-12 membered heterocyclic ring. Examples of such atoms include: substituted or unsubstituted alkylene moieties, such as those having the formula —$(CH_2)_i$—, where is an integer from 1 to 8; and moieties having the formula —$(CH_2)_i$—X—$(CH_2)_j$—, where i and j each independently represent integers from 0 to 4 and X is a heteroatom, such as O, S, and $NR^{70}$, where $R^{70}$ is a substituted or unsubstituted alkyl, aryl, or heteroaryl group. Illustratively, $Z^2$ and $Z^3$ can be the same, as in the case where each of $Z^2$ and $Z^3$ has the formula —$CH_2CH_2$—. $Z^1$ is an alkylene or arylene group. Illustratively, $Z^1$ can have the formula —$(CH_2)_i$—, where i is an integer from 1 to 8. Alternatively, $Z^1$ can have the formula —$(CH_2)_i$—X—$(CH_2)_j$—, where i and j each independently represent integers from 0 to 4 and X is a heteroatom, such as O, S, and $NR^{70}$, where $R^{70}$ is an alkyl or aryl group. Still alternatively, $Z^1$ can be a cycloalkyl moiety, such as cyclopent-1,3-diyl and cyclohex-1,3-diyl, which can be substituted or unsubstituted. Still alternatively, $Z^1$ can be an arylene moiety, such as a 1,3-phenylene or 1,3-naphthylene, or an heterocyclic moiety, such as a pyrid-3,5-diyl, pyrid-2,6-diyl, 2H-pyran-3,5-diyl, and tetrahydropyran-3,5-diyl moiety. $Q^1$ and $Q^2$ are the same or different and are electron withdrawing groups. Examples of $Q^1$ suitable for use in the practice of the present invention are moieties having the formulae —C(O)$R^1$, —$SO_2R^1$, and —P(O)$R^1R^{1'}$, and examples of suitable $Q^2$ include moieties having the formulae —C(O)$R^2$, —$SO_2R^2$, and —P(O)$R^2R^{2'}$. In these formulae, each of $R^1$, $R^{1'}$, $R^2$, and $R^{2'}$ is independently selected from an alkyl group, an aryl group, and an alkoxy group. In one illustrative embodiment, $Q^1$ has the formula —$SO_2R^1$; $Q^2$ has the formula —$SO_2R^2$; and $R^1$ and $R^2$ are the same or different and are substituted or unsubstituted alkyl or aryl groups, such as in the case where $Q^1$ has the formula —$SO_2R^1$; $Q^2$ has the formula —$SO_2R^2$; and each of $R^1$ and $R^2$ is independently selected from the group consisting of 4-(t-butyl)phenyl, 2,4,6-trimethylphenyl, and 2,4,6-triisopropylphenyl. In the above Formula IV, $L^1$ and $L^3$, taken together, represent a —O—$CR^{13}$—O— moiety, and $L^2$ and $L^4$, taken together, represent a —O—$CR^{14}$—O— moiety. In these moieties, $R^{13}$ and $R^{14}$ can be the same or they can be different, and each is independently selected from the group consisting of alkyl groups and aryl groups. Alternatively, $R^{13}$ and $R^{14}$ can represent alkylene or arylene groups that are directly or indirectly bonded to one another. In the latter case, the dirhodium tetracarboxylate catalysts of Formula IV can be expressed as the following formula ("Formula V"):

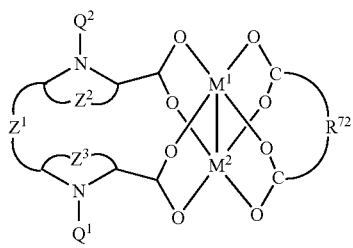

where $R^{72}$ represents an alkylene or arylene group. Illustratively, $R^{72}$ can be selected such that the dirhodium tetracarboxylate catalysts of Formula V have the following formula ("Formula VI"):

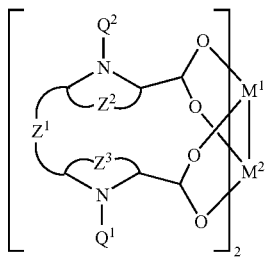

The dirhodium tetracarboxylate catalysts of Formulae IV, V, and VI have at least four stereocenters (i.e., at least the two carbons to which $Z^2$ is bonded and at least the two carbons to which $Z^3$ is bonded are stereocenters). Formulae IV, V, and VI are not meant to be limited to any particular set of configurations at the catalyst's stereocenters, and the structures given in these formulae are meant to be broadly read to include any and all possible collections of stereocenters. For example, catalysts of Formula VI are meant to include (i) compounds having the formula ("Formula VII"):

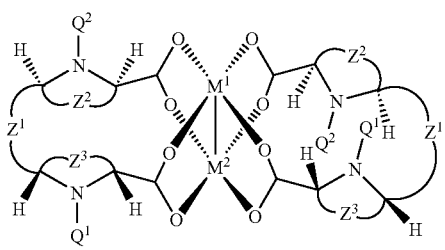

and (ii) compounds having the formula ("Formula VIII"):

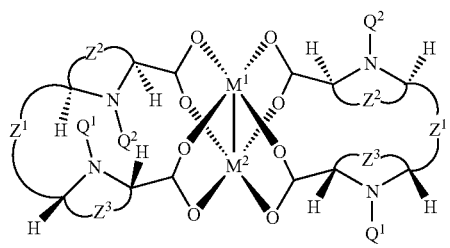

Each of the catalysts having Formulae VII and VIII can be present alone (i.e., as a pure diastereoisomer), or it can be present in a mixture with one or more different diastereoisomers. Alternatively, the catalysts having Formulae VII and VIII can be substantially free of other diastereoisomers. In this context, "substantially free of other disatereoisomers" means that the molar ratio of other diastereoisomers to the catalyst is less than 40%, such as less than 30%, less than 20%, less than 10%, less than 5%, less than 2%, and/or less than 1%.

Examples of catalysts having Formula VII and VIII, respectively, are those having the formula ("Formula IX")

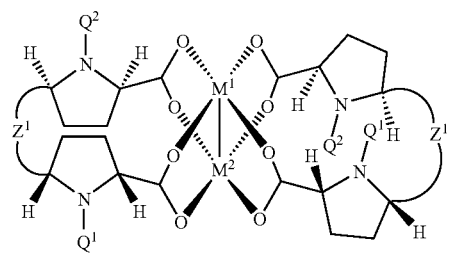

and those having the formula ("Formula X"):

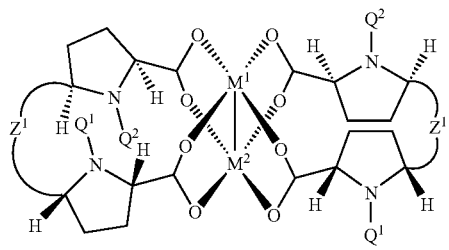

Still other examples of catalysts having Formula VII and VIII, respectively, are those having the formula ("Formula XI"):

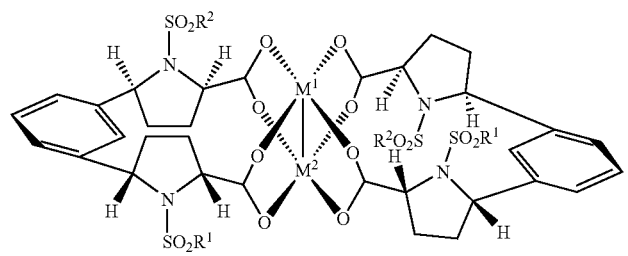

and those having the formula ("Formula XII"):

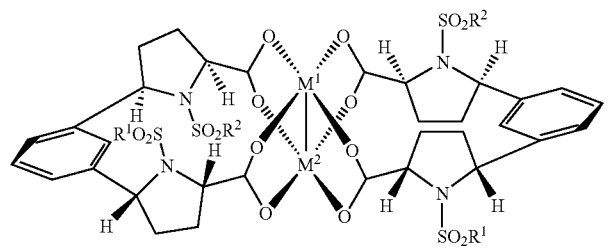

In Formula XI and Formula XII, $R^1$ and $R^2$ can be the same or different and each can be selected from, for example, alkyl groups and aryl groups.

As used in the above discussion and elsewhere herein, "arylene" is meant to include a bivalent aryl group in which both valencies are present on aromatic carbons. Examples of such groups include, for example, 1,3-phenylene, 1,4-phenylene, 5-methyl-1,3-phenylene, pyrid-2,3-diyl, pyrid-2,4-diyl, pyrid-2,5-diyl, pyrid-3,5-diyl, 1,3-naphthylene, 1,7-naphthylene, 1,8-naphthylene, 5,6,7,8-tetrahydro-1,3-naphthylene, thiophene-2,5-diyl, and furan-2,5-diyl. "Arylene", as used herein, is also meant to include a bivalent group having the formula —R—R'— where R is an alkyl group and R' is an aryl group. As the structure of —R—R'— indicates, one of the valencies is on the R (i.e., alkyl) portion of the —R—R'— moiety and the other of the valencies resides on the R' (i.e., aryl) portion of the —R—R'— moiety. Examples of this type of arylene moiety include moieties having the formulae:

and the like.

Other suitable dirhodium tetracarboxylate catalysts as well as methods for making various dirhodium tetracarboxylate catalysts are described in, for example, U.S. Pat. No. 6,410, 746 to Davies, International Publication No. WO 00/64583; and Davies et al., "Novel Dirhodium Tetraprolinate Catalysts Containing Bridging Prolinate Ligands For Asymmetric Carbenoid Reactions," *Tetrahedron Letters*, pages 5287-5290 (1999), each of which is hereby incorporated by reference.

Other suitable dirhodium catalysts include dirhodium tetracarboxamidate catalysts, such as those having the following formula ("Formula XIII"):

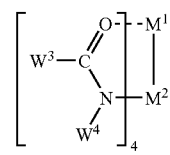

In Formula XIII, each of $M^1$ and $M^2$ is Rh. $W^3$ represents an alkyl group, an aryl group, an alkoxy group, or an amine group, and $W^4$ represents an alkyl group or an aryl group. Alternatively, $W^3$ and $W^4$, taken together with the atoms to which they are bonded, represent a 3-12 membered ring, for example, as shown in the following formula ("Formula XIV"):

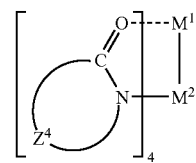

In Formula XIV, $Z^4$ represents the atoms necessary to complete a 3-12 membered ring. The ring can be substituted or unsubstituted; and it can include additional heteroatoms (i.e., in addition to the N to which $Z^4$ is bonded, or it can consist only of carbons (except for the N to which $Z^4$ is bonded). Illustratively, $Z^4$, together with the carbon and N atoms to which it is bonded, can represents a substituted or unsubstituted C3-C8 lactam ring, a substituted or unsubstituted oxazolidone ring, a substituted or unsubstituted pyrrolidone ring, or a substituted or unsubstituted imidazolidone ring. Specific examples of suitable catalysts of Formula XIV include: dirhodium(II) tetrakis(caprolactam); dirhodium(II) tetrakis[methyl 2-oxazolidone-4-carboxylate]; dirhodium(II) tetrakis[methyl 2-oxazolidone-4-(S)-carboxylate]; dirhodium(II) tetrakis[methyl 2-pyrrolidone-5-carboxylate]; dirhodium(II) tetrakis[methyl 2-pyrrolidone-5(R)-carboxylate]; dirhodium(II) tetrakis[methyl 2-pyrrolidone-5(S)-carboxylate]; dirhodium(II) tetrakis[methyl 1-(3-phenylpropanoyl)-2-imidazolidone-4-carboxylate; dirhodium(II) tetrakis[methyl 1-(3-phenylpropanoyl)-2-imidazolidone-4(S)-carboxylate; and adducts (e.g., acetonitrile and/or alcohol adducts) thereof. Methods for producing these and other dirhodium tetracarboxamidate catalysts can be found, for example, in U.S. Pat. No. 5,175,311 to Doyle, which is hereby incorporated by reference.

The aforementioned dirhodium catalysts can be tethered, for example as described in WO 03/018184, which is hereby incorporated by reference. Additionally or alternatively, the aforementioned dirhodium catalysts can be used in conjunction with an organic ester, as described in WO 03/018183, which is hereby incorporated by reference.

Contacting the cyclohexene compound and vinyldiazo compound in the presence of a dirhodium catalyst can be carried out under any conditions that are effective to produce a compound having Formula XXI. Illustratively, the cyclohexene compound can be contacted with the vinyldiazo compound in any suitable solvent, examples of which include alkane solvents (e.g., hexanes, 2,2-dimethylbutane, etc.), aromatic solvents (e.g., benzene, toluene, trifluorotoluene, etc.), and combinations thereof (e.g., a hexanes/toluene mixture). The cyclohexene compound and vinyldiazo compound can be reacted in any suitable mole ratio, such as cyclohexene compound:vinyldiazo compound mole ratios of from about 5:1 to about 1:5, such as from about 4:1 to about 1:4, from about 3:1 to about 1:3 from about 2:1 to about 1:2, from about 1.8:1 to about 1:1.8, from about 1.5:1 to about 1:1.5, from about 1.4:1 to about 1:1.4, from about 1.3:1 to about 1:1.3, from about 1.2:1 to about 1:1.2, from about 1.1:1 to about 1:1.1, from about 1.05:1 to about 1:1.05, and/or about 1:1. The reaction can be carried out at any suitable temperature, such from about 0° C. to about the boiling point of the solvent being employed, from about 0° C. to about room temperature, from about room temperature to about the boiling point of the solvent, from about 0° C. to about 100° C., from about 0° C. to about 80° C., from about 0° C. to about 70° C., from about 0° C. to about 60° C., from about 0° C. to about 50° C., and/or at about room temperature. The amount of dirhodium catalyst present can be from about 0.05 mol % to about 10 mol %, such as from about 0.1 mol % to about 5 mol %, from about 0.2 mol % to about 2 mol %, from about 0.25 mol % to about 0.1 mol %, from about 0.3 mol % to about 0.8 mol %, from about 0.4 mol % to about 0.6 mol %, and/or about 0.5 mol %, based, for example, on the number of moles of the limiting reactant present in the reaction.

As discussed above, the method can further include the optional steps of treating the compound of Formula XXI with a reducing agent under conditions effective to reduce the ring double bond between the carbons to which Z is not bonded, to reduce the double bond between the carbons to which $R^{25}$ and Y are bonded, and/or to reduce Y, for example, to produce a compound of Formula XXIV in which $R^{28}$ and $R^{29}$ are hydrogen atoms, $R^{26}$ and $R^{27}$ are hydrogen atoms, and/or $Q^{11}$ an alkyl group (e.g., a hydroxymethyl group). Illustratively, the ring double bond between the carbons to which Z is not bonded and the double bond between the carbons to which $R^{25}$ and Y are bonded can be reduced by catalytic hydrogenation, for example, with $H_2$ over a suitable catalyst (e.g., palladium on carbon). Additionally or alternatively, the Y can be reduced to a hydroxymethyl group, for example, with lithium aluminum hydride. The method of the present invention can further include other additional steps, for example, to convert the hydroxymethyl group formed by reduction of Y to another alkyl group (e.g., a methyl group or another alkyl group, a halomethyl group, an aldehyde group, etc.). As further illustration, the method of the present invention can further include other optional steps to manipulate other substituents (e.g., $R^{21}$, $R^{30}$, $R^{31}$, $R^{30}$, $R^{32}$, $R^{33}$ etc.).

The compounds of the present invention and compounds produced by the methods of the present invention can be used to make a variety of products, such as, for example, erogorgiaene congeners. "Erogorgiaene congener", as used herein, is meant to refer to naturally occurring and non-naturally occurring compounds which contain either (i) the

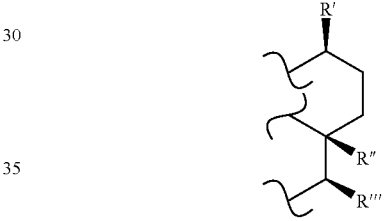

moiety, such as that found in (+)-erogorgiaene and in other marine diterpenes, such as pseudopterosin A, helioporin E, pseudopteroxazole, colombiasin A, elisapoterosin B, elisabethadione, p-benzoquinone natural products, ileabethin or (ii) the

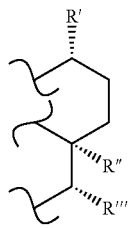

moiety, such as that found in (−)-erogorgiaene and in other marine diterpenes, such as the sinulobtains (e.g., sinulobtain B, sinulobtain C, and sinulobtain D). Illustrative examples of erogorgiaene congeners are set forth in FIG. 1. In the erogorgiaene congeners set forth in the last row of FIG. 1, R, $R^1$, $R^2$, $R^3$, $R^4$, and $R^5$ can be the same or different, and they can be independently selected from any of the groups recited hereinabove in the discussion relating to substituents on alkyl and aryl groups. Illustratively, R, $R^1$, $R^2$, $R^3$, $R^4$, and $R^5$ can be the same or different, and they can be selected from H; substituted or unsubstituted alkyl; substituted or unsubstituted aryl.

Still other illustrative examples of erogorgiaene congeners are set forth in Heckrodt et al., "Marine Natural Products from *Pseudopterogorgia elisabethae*: Structures, Biosynthesis, Pharmacology, and Total Synthesis," Topics in Current Chemistry, 244:1-41 (2005), which is hereby incorporated by reference.

The method for preparing erogorgiaene congeners according to the present invention includes providing a compound having Formula XXI and converting the compound to the erogorgiaene congener. Examples of erogorgiaene congeners that can be prepared by this method include erogorgiaene, pseudopterosin A, helioporin E, pseudoperoxazole, colombiasin A, elisapoterosin B, elisabethadione, p-benzoquinone natural products, ileabethin, sinulobtain B, sinulobtain C, and sinulobtain D.

Illustratively, in the case where the desired erogorgiaene congener is erogorgiaene, the method involves providing a compound having Formula XXIV, wherein each of $R^{21}$, $R^{23}$, and $R^{32}$ is a methyl group; wherein each of $R^{22}$, $R^{24}$, $R^2$, $R^{30}$, $R^{31}$, and $R^{33}$ is a hydrogen atom; and wherein Y is an ester group (e.g., by using a method of the present invention as discussed above). The compound is then converted to erogorgiaene, for example, by treating the compound with a reducing agent under conditions effective to reduce the ring double bond between the carbons to which Z is not bonded and to reduce the double bond between the carbons to which $R^{25}$ and Y are bonded; and treating the compound with a reducing agent under conditions effective to reduce Y. Illustratively, reduction of the ring double bond between the carbons to which Z is not bonded can be carried out by catalytic hydrogenation, for example, with $H_2$ over a suitable catalyst (e.g., palladium on carbon); and Y can be reduced to a hydroxymethyl group, for example, with lithium aluminum hydride. In the case where Y is reduced to a —$CH_2OH$ group, the method can further include oxidizing the Y —$CH_2OH$ group (i.e., the —$CH_2OH$ group formed by reduction of Y) to a —CHO group to produce an oxidized compound. The oxidized compound can then converted to erogorgiaene by a process that includes reacting the oxidized compound with a compound having the formula $R_3P=C(CH_3)_2$ wherein each R independently represents the same or a different aryl group, such as the same or a different substituted or unsubstituted phenyl group (e.g., as in the case where each R represents an unsubstituted phenyl group). Further details with regard to the conversion of a compound having Formula XXIV to erogorgiaene can be found in the Examples section of the present application.

As further illustration, in the case where the desired erogorgiaene congener is colombiasin A or elisapterosin B, the method involves providing a compound having Formula XXIV, wherein each of $R^{21}$, $R^{23}$, and $R^{32}$ is a methyl group; wherein $R^{31}$ is a methoxy group; wherein each of $R^{22}$, $R^{24}$, and $R^{25}$ is a hydrogen atom; wherein $R^{30}$ and $R^{33}$ is a protected hydroxy group; and wherein Y is an ester group (e.g., by using a method of the present invention as discussed above). The compound is then converted to colombiasin A or elisapterosin B, for example, by treating the compound with a reducing agent under conditions effective to reduce the ring double bond between the carbons to which Z is not bonded and to reduce the double bond between the carbons to which $R^{25}$ and Y are bonded; and treating the compound with a reducing agent under conditions effective to reduce Y to a —$CH_2OH$ group to produce a reduced compound having the formula ("Formula XXV"):

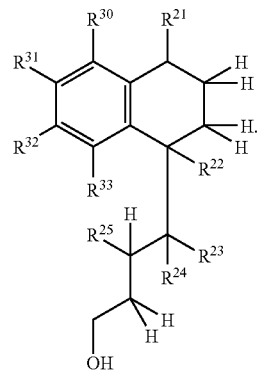

Illustratively, reduction of the ring double bond between the carbons to which Z is not bonded can be carried out by catalytic hydrogenation, for example, with $H_2$ over a suitable catalyst (e.g., palladium on carbon); and Y can be reduced to a —$CH_2OH$ group, for example, with lithium aluminum hydride. The reduced compound (Formula XXV) can then be treated with an alkylating agent under conditions effective to produce a diene compound having the formula ("Formula XXVI"):

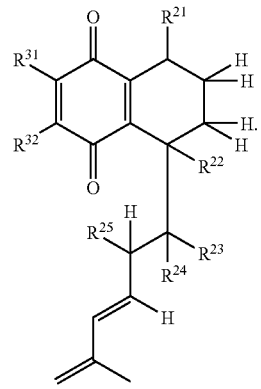

For example, alkylation can be carried out by oxidation of the reduced compound to the aldehyde (e.g., using pyridinium chlorochromate ("PCC")) followed by Grignard addition using, for example, a Grignard agent having the formula:

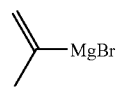

Where the desired erogorgiaene congener is colombiasin A, the method can further include treating the diene compound under conditions effective to convert the diene compound to colombiasin A via an intramolecular Diels-Alder reaction and demethylation. Illustratively, the intramolecular Diels-Alder reaction can be carried out by heating the diene in a suitable solvent (e.g., toluene or another aromatic solvent) at, for example, from about 100° C. to the boiling point of the solvent employed (e.g., at from about 150° C. to about 200° C., such as at about 180° C.). Demethylation can be readily carried out by conventional chemistry, such as by treatment with aluminum chloride in an organic amine, such as dimethylphenylamine. Where the desired erogorgiaene congener is elisapterosin B, the method can further include treating the diene compound with boron trifluoride under conditions effective to convert the diene compound to elisapterosin B via a [5+2] cycloaddition reaction. This reaction can be carried out using boron trifluoride etherate, and is typically carried out cold (e.g., at −78° C.) for a period of time (e.g., from about 30 minutes to about 3 hours, from about 30 minutes to about 2 hours, and/or for about 1 hour). Further details with regard to the conversion of a compound having Formula XXIV to colombiasin A and to elisapterosin B can be found in the Examples section of the present application.

As further illustration, in the case where the desired erogorgiaene congener is elisabethadione or a p-benzoquinone natural product, the method involves providing a compound having Formula XXIV, wherein each of $R^{21}$, $R^{23}$, and $R^{32}$ is a methyl group; wherein each of $R^{30}$, $R^{31}$, and $R^{33}$ is a methoxy group; wherein each of $R^{22}$, $R^{24}$, and $R^2$ is a hydrogen atom; and wherein Y is an ester group (e.g., by using a method of the present invention as discussed above). by treating the compound with a reducing agent under conditions effective to reduce the ring double bond between the carbons to which Z is not bonded and to reduce the double bond between the carbons to which $R^{25}$ and Y are bonded; and treating the compound with a reducing agent under conditions effective to reduce Y to a —CH$_2$OH group to produce a reduced compound having the formula ("Formula XXVII"):

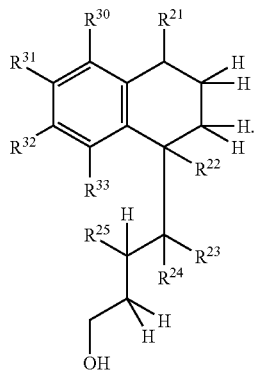

Illustratively, reduction of the ring double bond between the carbons to which Z is not bonded can be carried out by catalytic hydrogenation, for example, with H$_2$ over a suitable catalyst (e.g., palladium on carbon); and Y can be reduced to a —CH$_2$OH group, for example, with lithium aluminum hydride. Where the desired erogorgiaene congener is elisabethadione, the Y —CH$_2$OH group of the reduced compound (Formula XXVII) can then be oxidized to an aldehyde group (e.g., using pyridinium chlorochromate ("PCC")), and the resulting oxidized compound can be converted to elisabethadione, for example, by reacting the oxidized compound with a compound having the formula R$_3$P═C(CH$_3$)$_2$ wherein each R independently represents the same or a different aryl group, such as the same or a different substituted or unsubstituted phenyl group (e.g., as in the case where each R represents an unsubstituted phenyl group. Conversion of the oxidized compound to elisabethadione can further include demethylation with lithium ethanethiolate and oxidation with cerium ammonium nitrate. Lithium ethanethiolate demethylation is suitably carried out by heating (e.g., at from about 130° C. to about 230° C., such as at from about 150° C. to about 210° C., at from about 170° C. to about 190° C., and/or at about 180° C.) for from about 1 to about 12 hours (such as for from about 1 to about 8 hours, for from about 2 to about 6 hours, for from about 2 to about 4 hours, and/or for about 3 hours) in a suitable solvent (e.g., DMF). Oxidation with cerium ammonium nitrate can be readily carried out, for example, in an ice bath (e.g., at about 0° C.) for a brief period of time (e.g., from about 5 minutes to about 30 minutes, such as for about 10 minutes). Where the desired erogorgiaene congener is a p-benzoquinone natural product, the reduced compound can be converted to an alkene compound having the formula ("Formula XXVIII"):

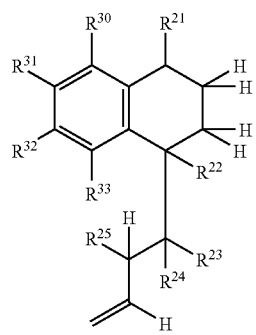

by elimination of water, for example, by application of Grieco's selenoxide introduction/elimination procedure using, for example, ortho (O$_2$N)C$_6$H$_4$SeCN in the presence of a trialkylphosphine (e.g., P(Bu)$_3$) in a suitable solvent (e.g., an ether solvent, such as tetrahydrofuran) at about room temperature followed by treatment with an oxidizing agent, such as a peroxide oxidizing agent (e.g., hydrogen peroxide) in a suitable solvent (e.g., an ether solvent, such as tetrahydrofuran) at about room temperature. Conversion of the oxidized compound to a p-benzoquinone natural product can further include demethylation of the alkene compound (Formula XXVIII) with lithium ethanethiolate and oxidation with cerium ammonium nitrate, for example, as described above in the context of preparing elisabethadione, followed by reaction with an allylic alcohol having the formula:

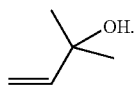

Installation of the allylic alcohol can be carried out, for example, by a cross-metathesis reaction catalyzed by a ruthenium catalyst (e.g. a Grubbs second-generation ruthenium catalyst) using, for example, Jacobsen's strategy (described, for example, in Boezio et al., *Angew. Chem. Int. Ed.,* 44:6046-6050 (2005), which is hereby incorporated by reference). Further details with regard to the conversion of a compound having Formula XXIV to elisabethadione or a p-benzoquinone natural product can be found in the Examples section of the present application.

The present invention is further illustrated by the following non-limiting examples.

EXAMPLES

Example 1

Enantioselective Synthesis of (+)-Erogorgiaene

Figure 2:
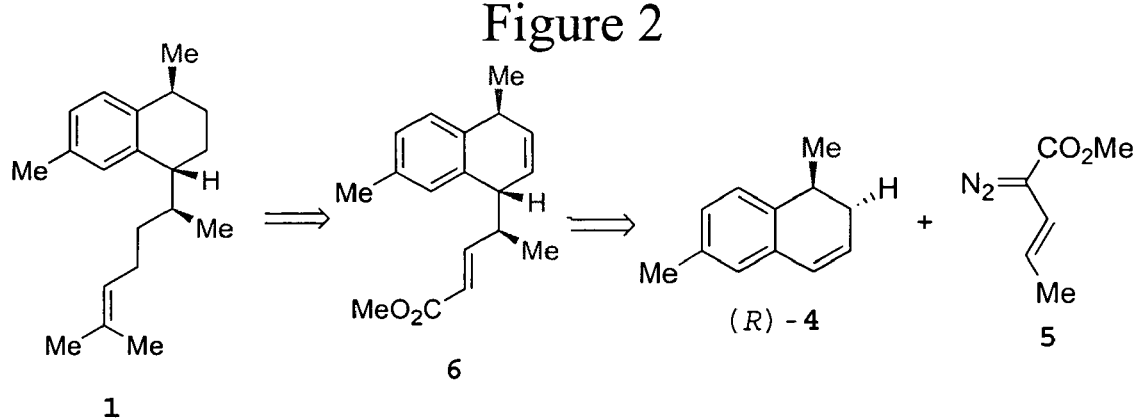
FIG. 2 is a retrosynthetic analysis of erogorgiaene showing the use of compounds and methods of the present invention.

In this example, we illustrate, through the enantioselective synthesis of (+)-erogorgiaene (1), set forth in FIG. 2, a general strategy to the synthesis of a general class of diterpenes. An important step in this synthesis is our recently-discovered dirhodium tetraprolinate ($Rh_2(DOSP)_4$) catalyzed combined C—H activation/Cope rearrangement, a reaction that is notable for its very high diastereoselectivty and enantioselectivity (Davies et al., *Proc. Natl. Acad. Sci. USA,* 101:5472-5475 (2004) and Davies et al., *J. Am. Chem. Soc.,* 126:10862-10863 (2004) ("Davies"), which are hereby incorporated by reference). Application of this methodology to the retrosynthetic analysis of (+)-erogorgiaene revealed that the unsaturated ester 6 would be a very desirable precursor to 1. Reaction of the vinyldiazoacetate 5 with the dihydronaphtalene (R)-4 would be expected to readily form 6 with the desired relative stereochemistry, as illustrated in FIG. 2.

Figure 3:
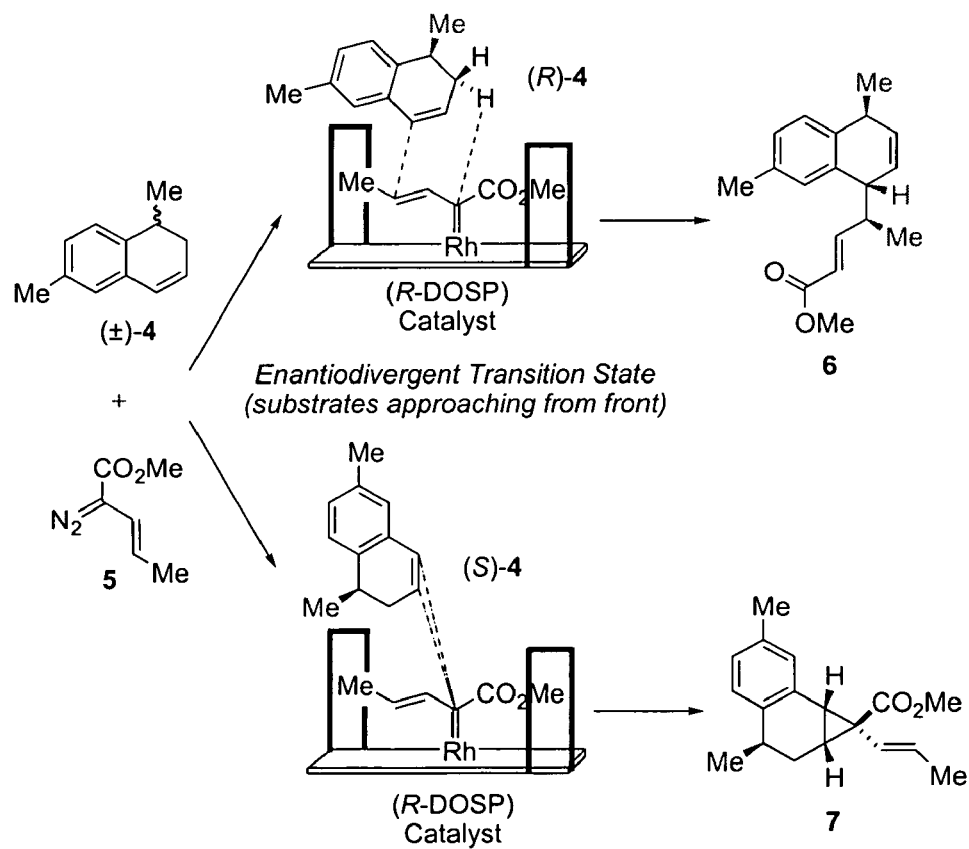
FIG. 3 is a stereochemical analysis for combined C—H activation/Cope rearrangement strategy employed in a method of the present invention.

During the analysis of this synthetic problem, we recognized that the synthesis offered a very exciting opportunity for enantiomer differentiation, such that the racemic dihydronaphthalene (±)-4 could be used as starting material. Even though the exact mechanism of these carbenoid reactions is not known, we have developed models, which are excellent at predicting the stereochemical outcome of this chemistry (Davies; Nowlan et al., *J. Am. Chem. Soc.,* 125:15902-15911 (2003); and Davies et al., J. Chem. Rev., 103:2861-2904 (2003), which are hereby incorporated by reference). Applying these models to the $Rh_2(R-DOSP)_4$ catalyzed reaction of (±)-4 with 5, revealed that only the (R)-3 would be capable of a matched combined C—H activation/Cope rearrangement to form 6 while (S)-4 would be matched for a cyclopropanation to form 7, as illustrated in FIG. 3.

This would be a very exciting outcome because the dihydronaphthalene (±)-4 could potentially be used as the limiting agent as both enantiomers would be consumed but will form different products.

Figure 4:
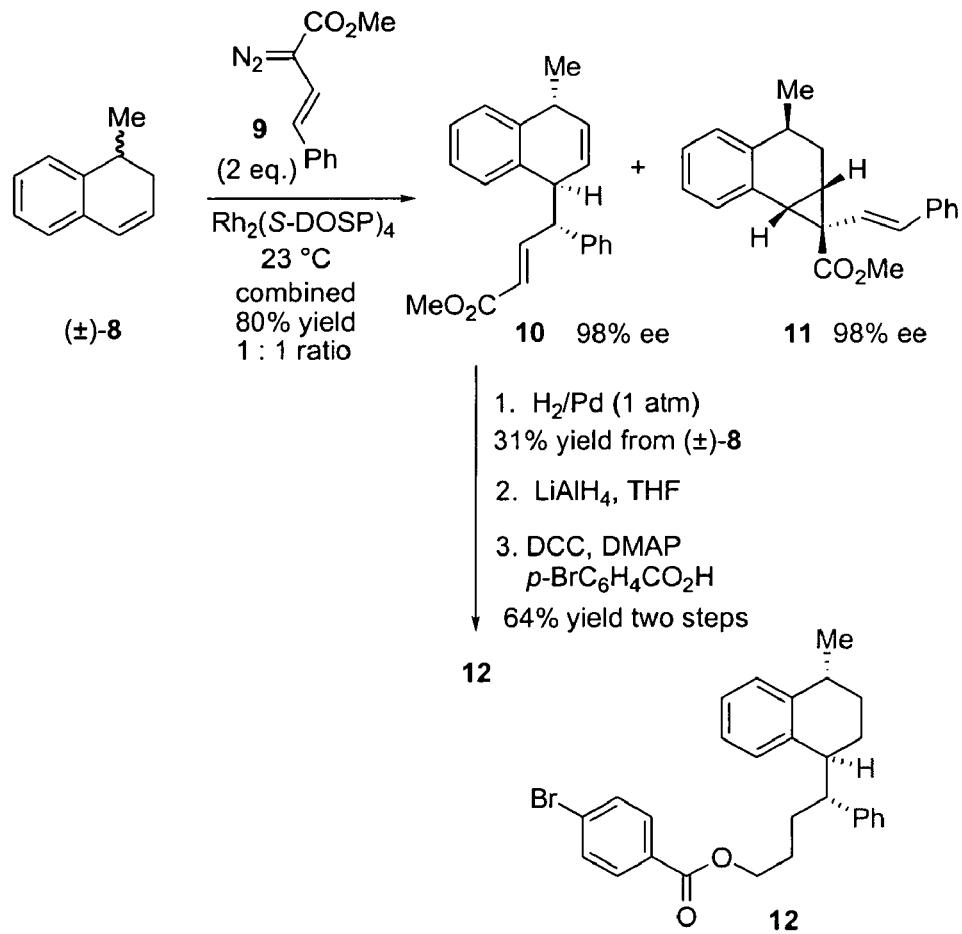
FIG. 4 is a reaction scheme in accordance with a method of the present invention.

In order to test this possibility the reaction of dihydronaphthalene 8 with the phenylvinyldiazoacetate 9 was used as a model reaction, as illustrated in FIG. 4. We were delighted to find that the $Rh_2(S-DOSP)_4$ catalyzed reaction gave a 1:1 mixture of the combined C—H activation/Cope rearrangement product 10 and the cyclopropane 11 in a combined yield of 80%. Remarkably, both products were produced in 98% ee and as essentially single diastereomers. Confirmation of the relative and absolute stereochemistry of 10 was achieved by conversion of 10 to the crystalline p-bromobenzoate 12 whose configuration was confirmed by X-ray crystallography (Gerlits et al., *Private Communication* CCDC 242585 (2004), which is hereby incorporated by reference).

Figure 5:
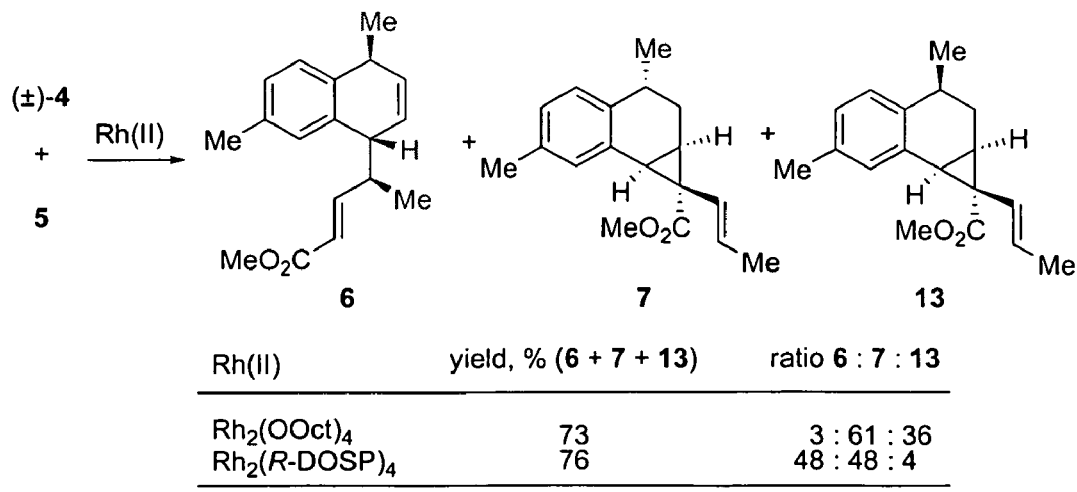
FIG. 5 is a reaction scheme in accordance with a method of the present invention showing the effect of various catalysts on product distribution.

Having successfully completed the model studies, attention was then directed towards the total synthesis of ergorgiaene. The step of rhodium catalyzed reaction between the vinyldiazoacetate 5 and the dihydronaphthalene (±)-4 is set forth in FIG. 5. The comparison between the reaction of 5 with (±)-4 catalyzed by rhodium octanoate and $Rh_2(R-DOSP)_4$ is very informative because it demonstrates the important role of $Rh_2(R-DOSP)_4$ not only to induce the enantioselectvity but also to achieve an effective C—H transformation. The rhodium(II) octanoate catalyzed reaction between 5 with (±)-4 results in the formation of only a trace of the combined C—H activation/Cope rearrangement product 6. The major products are the diastereomeric cyclopropanes 7 and 13 (as racemic mixtures). In contrast, the $Rh_2(R-DOSP)_4$ catalyzed reaction is truly exceptional, resulting in a 1:1 mixture of the combined C—H activation product 6 and the cyclopropane 7 with just a trace of the diastereomer 13. Furthermore, 6 was formed in 90% ee.

Figure 6:
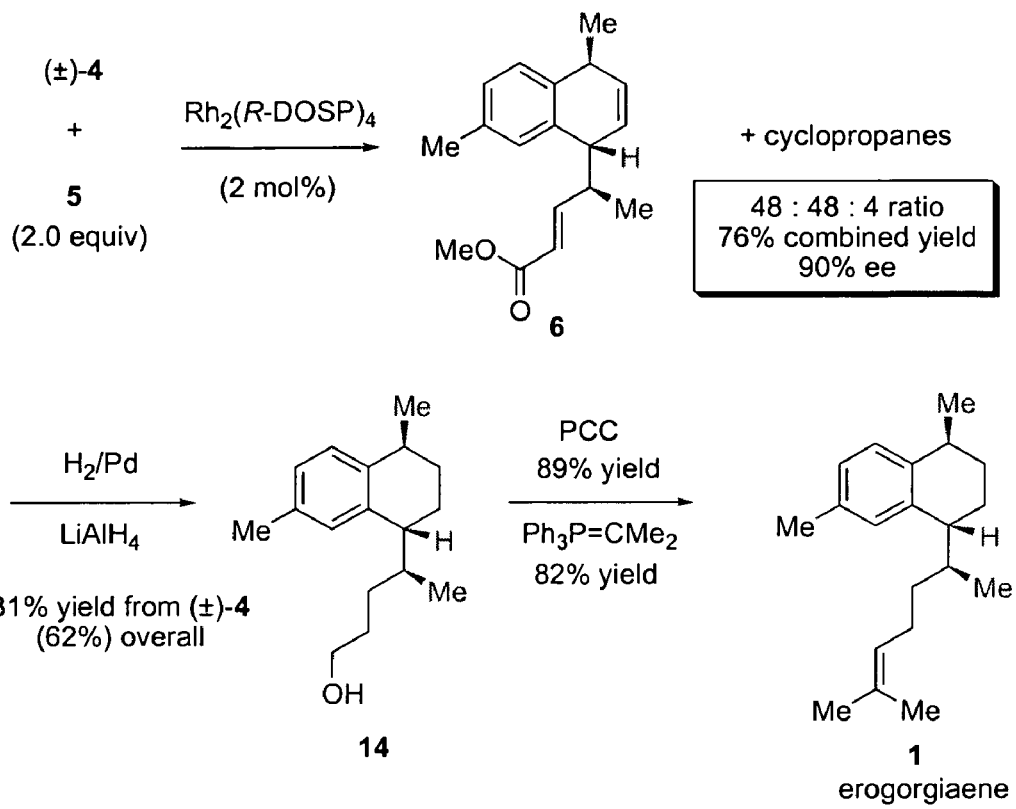
FIG. 6 is a reaction scheme for the preparation of erogorgiaene showing the use of compounds and methods of the present invention.

The completion of the synthesis of (+)-erogorgiaene (1) was readily achieved, as illustrated in FIG. 6. Due to the tendency of 6 to undergo a retro-Cope rearrangement, the combined mixture of 6 and 7 was globally hydrogenated and the ester was reduced to the alcohol 14, which was isolated in 31% overall yield from the dihydronapthalene (±)-4 (62% yield from the matched enantiomer (R)-4). PCC oxidation of 14 to the aldehyde followed by a Wittig reaction completed the total synthesis of (+)-erogorgiaene (1), as illustrated in FIG. 6.

In summary, Example 1 demonstrates that the combined C—H activation/Cope rearrangement protocol is an exceptional method for the construction of the three stereogenic centers common to the numerous diterpenes isolated from *Pseudopterogorgia elisabethae* and other erogorgiaene congeners. Experimental details for the reactions described in this Example 1 are set forth in Example 2.

Example 2

Experimental Details for Enantioselective Synthesis of (+)-Erogorgiaene

This Example 2 sets forth the experimental details for the reactions described in Example 1.

Commercial reagents from Aldrich Chemical Company and Acros Organics were purchased at the highest commercial purity and used without further purification unless otherwise stated. All moisture sensitive reactions were performed using glassware that was oven dried overnight (60° C.) and then flame dried under vacuum prior to use. Tetrahydrofuran ("THF"), hexanes, dichloromethane ("DCM"), acetonitrile, and toluene were used either directly from the solvent purification system (solvent was passed through two columns with activated alumina) purchased from MBRAUN, or distilled following the procedures of Perrin and Armarego (Perrin et al., Purification of Laboratory Chemicals, 3rd ed., Oxford, England:Pergamon (1988), which is hereby incorporated by reference). 2,2-dimethylbutane ("2,2-DMB") was purchased from Lancaster Synthesis, passed through activated silica gel (heated to 120° C. overnight), and distilled from sodium under argon. All other solvents were of reagent grade. Hydrogenations were carried out using a Parr hydrogenator at the specified $H_2$ pressure or using hydrogen filled balloons. Reaction solvents used in rhodium carbenoid transformations were degassed by bubbling argon gas through for 15 to 20 minutes prior to use. Organic reaction mixtures were concentrated using a Buchi rotary evaporator. Optical rotations were measured using a Jasco DIP-370 digital polarimeter. Analytical TLC was performed on 250 mm Whatman silica gel (Aluminum backing, UV 254 nm) plates using UV light and phosphomolybdic acid (10% in ethanol) as visualizing agents. Column chromatography was carried out using E. Merck silica 60 (230-400 mesh) or ICN 60 (32-64 mesh) following the method of Still (Still et al., *J. Org. Chem.,* 43:2923ff (1978), which is hereby incorporated by reference).

$^1$H NMR spectra were recorded on a Varian Nuclear Magnetic Resonance spectrometer at 300, 400, or 500 MHz and $^{13}$C spectra were recorded at 75 or 125 MHz, with the sample solvent being CDCl$_3$, unless otherwise noted. Infrared spectra were obtained on a Nicolet Impact 420 FT-IR spectrometer. High-resolution mass spectra were obtained from the Mass Spectroscopy Facility at the University at Buffalo, The State University of New York. Diastereomeric ratios were determined by values derived from the 500 MHz $^1$H NMR spectra of the crude reaction. Enantiomeric excess was determined by high performance liquid chromatography ("HPLC") using chiral analytical columns (specified for each compound) with 2-propanol (ipa) in hexane as the eluent (% ipa specified for each compound).

Figure 7A:
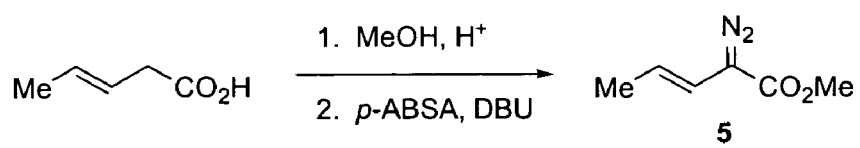
FIGS. 7A and 7B are reaction schemes for the preparation of various vinyldiazo compound that can be used in a method of the present invention.

Methyl (E)-2-diazo-3-pentenoate (5) was prepared using the scheme set forth in FIG. 7A. To a stirred solution of trans-pent-3-enoic acid (3.0 g, 30.0 mmol) in methanol (20 mL) was added concentrated H$_2$SO$_4$ (1 mL). The reaction mixture was stirred for 12 h at room temperature and then slowly neutralized with saturated sodium bicarbonate (Na$_H$CO$_3$). The aqueous layer was extracted with dichloromethane, and the combined organic layers were washed with brine and dried (Na$_2$SO$_4$). The solvent was removed under reduced pressure, and the remaining clear oil (3.30 g, 96% yield) was used for the next step, without further purification. To a stirred solution of methyl trans-pent-3-enoate (1.0 g, 8.77 mmol) and p-ABSA (3.15 g, 13.1 mmol) in CH$_3$CN (20 mL) cooled to 0° C., was added DBU (2.66 g, 17.5 mmol) in one portion. p-ABSA (p-acetamidobenzenesulfonyl azide) was prepared using the procedure outlined in Baum et al., *Synth. Commun.*, 17:1709ff (1987), which is hereby incorporated by reference. The reaction mixture was allowed to warm to room temperature over 7 h then quenched with saturated ammonium chloride (NH$_4$Cl). The aqueous layer was extracted with diethyl ether, and the combined organic layers were washed with brine and dried (Na$_2$SO$_4$). The solvent was removed under reduced pressure and the residue was purified by flash chromatography (SiO$_2$, pentane) to give methyl (E)-2-diazo-3-pentenoate (5) (0.80 g, 65% yield) as an orange oil, which was stored in pentane below −10° C. until ready for use. The spectroscopic data are consistent with previously reported data (Davies et al., *J. Org. Chem.*, 57:3186ff (1992), which is hereby incorporated by reference).

Figure 7B:
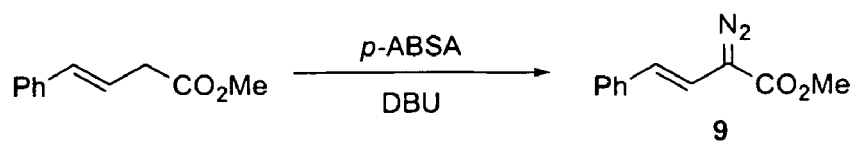

Methyl (E)-2-diazo-4-phenyl-3-butenoate (9) was prepared according to the procedure described in Davies, et al., *J. Org. Chem.*, 56:3817 (1997) ("Davies II"), which is hereby incorporated by reference. The scheme is set forth in FIG. 7B. Briefly, to a stirred solution of methyl trans-4-phenylbut-3-enoate (1.0 g, 5.68 mmol) and p-ABSA (1.64 g, 6.82 mmol) in CH$_3$CN (150 mL) cooled to 0° C., was added DBU (0.95 g, 6.25 mmol) in one portion. The reaction mixture was allowed to warm to room temperature over 7 h then quenched with saturated ammonium chloride (NH$_4$Cl). The aqueous layer was extracted with diethyl ether, and the combined organic layers were washed with brine and dried (Na$_2$SO$_4$). The solvent was removed under reduced pressure, and the residue was triturated with a solution of pentane/diethyl:ether (1:1). The solid was filtered off, and the solvent was removed under reduced pressure. The residue was purified by flash chromatography (SiO$_2$, pentane/diethyl:ether (15:1)) to give methyl (E)-2-diazo-4-phenyl-3-butenoate (9) (0.92 g, 80% yield) as an orange oil, which was stored neat at −10° C. until ready for use. The spectroscopic data are consistent with previously reported data ((Davies II, which is hereby incorporated by reference).

Figure 7C:
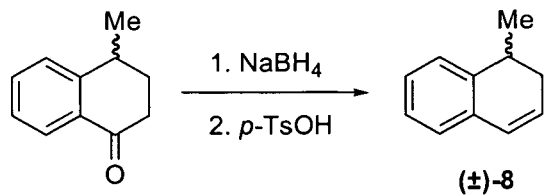
FIGS. 7C and 7D are reaction schemes for the preparation of various cyclohexene compound that can be used in a method of the present invention.

1,2-Dihydro-1-methylnaphthalene ((±)-8) was prepared using a similar procedure to that reported in Ferraz et al., *Tetrahedron*, 57:1709ff (2001) ("Ferraz") which is hereby incorporated by reference). The scheme is set forth in FIG. 7C. To a stirred solution of commercially available 4-methyl-α-tetralone (0.50 g, 3.12 mmol) in methanol (50 mL) was added NaBH$_4$ (0.35 g, 9.36 mmol) portionwise. The reaction mixture was followed by TLC and, after complete consumption of the starting material (approx. 2 h), was quenched with saturated NaHCO$_3$. The aqueous layer was extracted with diethyl ether, dried with magnesium sulfate (MgSO$_4$), filtered, and the solvent was removed under reduced pressure. The crude alcohol was dissolved in toluene (15 mL), and a few crystals of p-TsOH were added. The reaction mixture was stirred overnight, then neutralized by slow addition of saturated sodium bicarbonate (NaHCO$_3$) and extracted with diethyl ether. The combined organic layers where washed with brine, dried with magnesium sulfate (MgSO$_4$), filtered, and the solvent was removed under reduced pressure. The product was purified by flash chromatography (SiO$_2$, hexanes) to give 1,2-dihydro-1-methylnaphthalene ((±)-8) as a clear oil (0.35 g, 78% yield). The compound is volatile and cannot be dried for long periods (>30 min) under high vacuum. The spectroscopic data are consistent with previously reported data (Ferraz, which is hereby incorporated by reference).

Figure 7D:
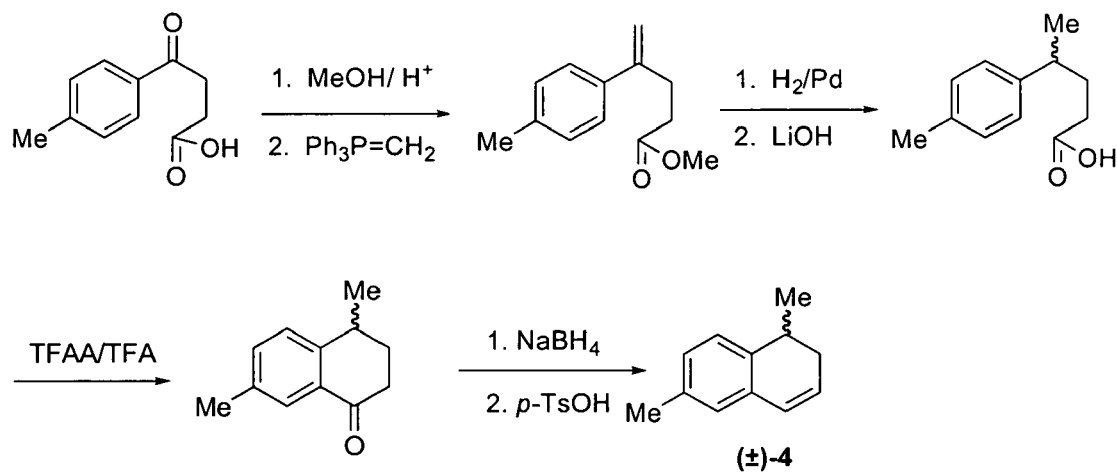

1,2-Dihydro-1,6-dimethylnaphthalene ((±)-4) was prepared using the scheme set forth in FIG. 7D.

To a stirring solution of commercially available 4-oxo-4-p-tolylbutanoic acid (1.0 g, 5.20 mmol) in methanol (20 mL) was added concentrated H$_2$SO$_4$ (1 mL) The reaction mixture was stirred for 12 h at room temperature and then slowly neutralized with saturated sodium bicarbonate (NaHCO$_3$). The aqueous layer was extracted with diethyl ether, and the combined organic layers were washed with brine and dried (Na$_2$SO$_4$). The solvent was removed under reduced pressure, and the remaining white solid (0.99 g, 92% yield) was used for the next step, without further purification. The spectroscopic data are consistent with previously reported data (Xu et al., *J. Org. Chem.*, 60:3039ff (1995) ("Xu"), which is hereby incorporated by reference).

To a cloudy white suspension of methyl triphenylphosphonium bromide (7.14 g, 19.9 mmol) in THF (35 mL) at room temperature was added KOtBu (2.02 g, 17.9 mmol). The reaction changed color to yellow upon addition of base and was allowed to stir for 15 min before addition of a THF solution (20 mL) of the ester (2.06 g, 10.0 mmol). The yellow color of the reaction mixture dissipated over 2 hours, and, after complete consumption of the ester (followed by TLC), the reaction was quenched with water. The aqueous layer was extracted with diethyl ether, and the combined organic layers were washed with brine and dried (MgSO$_4$). The solvent was removed under reduced pressure, and the residue was purified using flash chromatography (SiO$_2$, pentane:diethyl:ether (9:1 to 5:1)) to give the alkene (1.66 g, 81% yield). The spectroscopic data are consistent with previously reported data (Xu, which is hereby incorporated by reference).

To a solution of the alkene (1.66 g, 8.13 mmol) in ethanol (45 mL) was added palladium on carbon (10 mol %) and pressurized to 30 psi of hydrogen for 3 h. The reaction mixture was then filtered through a pad of celite, washed with diethyl ether, and concentrated under reduced pressure to give a clear oil (1.65 g, 98% yield), which required no further purification. The spectroscopic data are consistent with previously reported data (Ono et al., *Bull. Chem. Soc. Jpn.*, 49:1581ff (2001), which is hereby incorporated by reference).

A solution of the ester (1.65 g, 8.00 mmol) was prepared in a mixture of THF:MeOH:H2O (2:1:1), to which was added LiOH (1.34 g, 32.0 mmol). The reaction mixture was heated to 50° C. for 3 hours and then allowed to cool to room temperature. 10% aqueous hydrochloric acid was added dropwise to the reaction mixture until the pH of the solution reached pH 3. The aqueous layer was then extracted with diethyl ether, dried using MgSO$_4$, and filtered to give the carboxylic acid as an oil (1.50 g, 98% yield) which was used immediately for the next step.

Following the procedure reported in Zubaidha et al., *Tetrahedron*, 47:5759ff (1991), which is hereby incorporated by reference, a solution of trifluoroacetic anhydride (6.55 g, 31.2 mmol) in trifluoroacetic acid (1.5 mL) was prepared and added to the carboxylic acid (1.50 g, 7.80 mmol) which was cooled to 0° C. The reaction mixture was allowed to stir overnight. Water (3 mL) was added to the reaction mixture while the reaction mixture was stirring, and the acid was neutralized by the portionwise addition of solid NaHCO$_3$. After all the acid was neutralized, concentrated sodium hydroxide was added until the pH reached pH 10, and the reaction mixture was allowed to stir for 2 hours. The orange aqueous mixture was extracted diethyl ether, dried with MgSO$_4$, and concentrated under reduced pressure to give the tetralone as a pale yellow oil (0.867 g, 64% yield), which did not require further purification. The spectroscopic data are consistent with previously reported data (Chavan et al., *Tetrahedron:Asymmetry*, 8:2517ff (1997), which is hereby incorporated by reference).

Following a similar procedure to that reported in Ferraz, which is hereby incorporated by reference, to a stirred solution of 4-methyl-α-tetralone (0.867 g, 4.98 mmol) in methanol (20 mL) was added NaBH$_4$ (0.56 g, 14.9 mmol) portionwise. The reaction mixture was followed by TLC and, after complete consumption of the starting material (about 2 h), was quenched with saturated NaHCO$_3$. The aqueous layer was extracted with diethyl ether, dried with magnesium sulfate (MgSO$_4$), and filtered; and the solvent was removed under reduced pressure. The crude alcohol was dissolved in toluene (25 mL) and a few crystals of p-TsOH were added. The reaction mixture was stirred overnight, then neutralized by slow addition of saturated sodium bicarbonate (NaHCO$_3$) and extracted with diethyl ether. The combined organic layers where washed with brine, dried with magnesium sulfate (MgSO$_4$), and filtered; and the solvent was removed under reduced pressure. The product was purified by flash chromatography (SiO$_2$, hexanes) to give 1,2-dihydro-1,6-dimethyl-naphthalene ((±)-4) as a clear oil (0.479 g, 61% yield). This compound is volatile and cannot be dried for long periods (>30 min) under high vacuum. The spectroscopic data are consistent with previously reported data (Adachi et al., *Bull. Chem. Soc. Jpn.*, 56:651ff (1983), which is hereby incorporated by reference).

Figure 8:
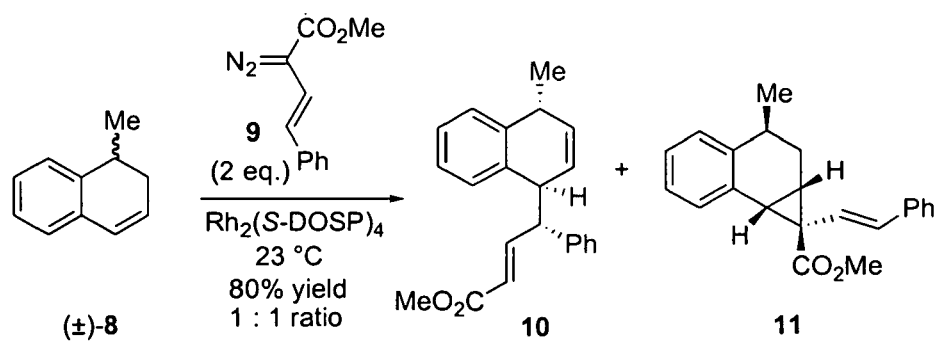
FIG. 8 is a reaction scheme in accordance with a method of the present invention.

(R,2E)-methyl 4-((1R,4S)-1,4-dihydro-1-methylnaphthalen-4-yl)-4-phenylbut-2-enoate (10) and (1R,1aS,3S,7bS)-methyl-1a,2,3,7b-tetrahydro-3-methyl-1-styryl-1H-cyclopropa[a]naphthalene-1-carboxylate (11) were prepared using the scheme set forth in FIG. 8.

To a flame dried 25 mL round bottom flask with a magnetic stir bar was added 1,2-dihydro-1-methylnaphthalene ((±)-8) (51 mg, 0.354 mmol) and Rh$_2$(S-DOSP)$_4$ (13.3 mg, 7×10$^{-3}$ mmol), dissolved in 2,2-DMB (2 mL) under argon at room temperature. In a 10 mL syringe, a solution of methyl E-2-diazo-4-phenyl-3-butenoate 9 (143 mg, 0.707 mmol) was prepared in 2,2-DMB (5 mL). The solution of diazo compound was added via syringe pump at a rate of 2.4 mL/h (~2 h addition time). After the diazo addition was complete, the reaction mixture was allowed to stir for an additional 0.5 h, and the solvent was removed under reduced pressure. Crude $^1$H NMR showed a 1:1 ratio of products 10:11, >98% de for both products. Purification by column chromatography (SiO$_2$, pentane:ether (17:1)) gave a combined mass of 90.1 mg (80% yield) in three fractions (39 mg of 10, 42 mg of 11, and 9.1 mg as a mixture of 10 and 11).

The 39 mg (35% yield) of 10 was obtained as a clear oil. R$_f$=0.51 (6:1 pentane:ether) 98% ee by HPLC using Chiralcel OD-H, 0.7 mL/min., 1.0% 2-propanol in hexane, t$_R$=9.4 (minor) and 10.7 (major) min, UV 254 nm. $^1$H NMR was consistent with the proposed structure. This material was directly submitted to the hydrogenation step because it had a tendency to undergo a retro-Cope rearrangement. All other spectroscopic data was obtained on hydrogenated compound 15.

The 42 mg (37% yield) of 11 was obtained as a clear oil. R$_f$=0.55 (6:1 pentane:ether) (>98% de by $^1$H NMR), 98% ee by HPLC using Chiralcel OD-H, 0.7 mL/min., 1.0% 2-propanol in hexane, t$_R$=9.4 (minor) and 10.4 (major) min, UV 254 nm. [α]$_D^{25}$=−1.60° (c=1.0, CHCl$_3$) $^1$H NMR, $^{13}$C NMR, and FTIR were consistent with the proposed structure. HRMS (EI) m/z calcd for [M]$^+$ (C$_{22}$H$_{22}$O$_2$)$^+$: 318.1614 found: 318.1602.

Figure 9:
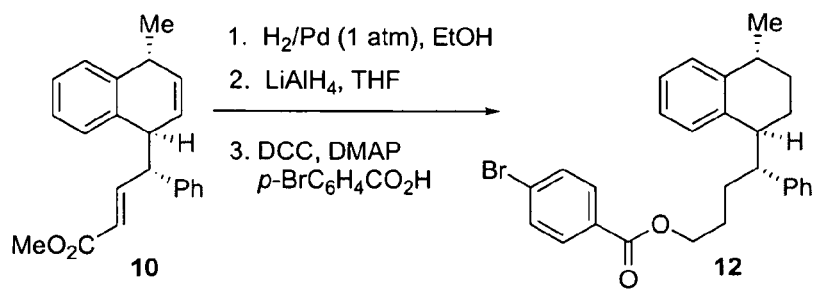
FIG. 9 is a reaction scheme for converting a compounds of the present invention to another compound of the present invention.

(R)-4-((1R,4S)-1,2,3,4-tetrahydro-1-methylnaphthalen-4-yl)-4-phenylbutyl-4-bromobenzoate (12) was prepared using the scheme set forth in FIG. 9.

Due to the tendency of product 10 to readily undergo the retro-Cope rearrangement, (R)-methyl-4-((1R,4S)-1,2,3,4-tetrahydro-1-methylnaphthalen-4-yl)-4-phenylbutanoate (15) was isolated by conducting a 2-step 1-pot procedure (rhodium(II) mediated C—H/Cope rearrangement followed by global hydrogenation). The 2-step 1-pot procedure also produced (1R,1aS,3S,7bS)-methyl-1a,2,3,7b-tetrahydro-3-methyl-1-phenethyl-1H-cyclopropa-[a]naphthalene-1-carboxylate (18).

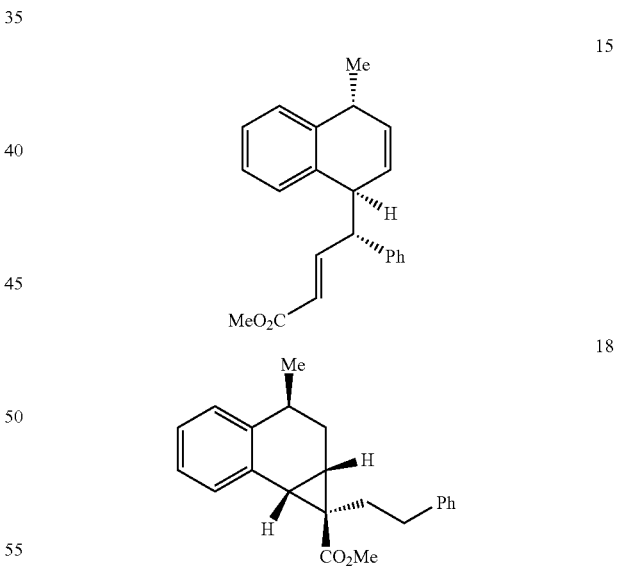

To a flame dried 25 mL round bottom flask with a magnetic stir bar was added 1,2-dihydro-1-methylnaphthalene ((±)-8) (72 mg, 0.50 mmol) and Rh$_2$(S-DOSP)$_4$ (13 mg, 6.9×10$^{-3}$ mmol), dissolved in 2,2-DMB (2 mL) under argon at room temperature. In a 10 mL syringe a solution of methyl E-2-diazo-4-phenyl-3-butenoate 9 (120 mg, 0.59 mmol) was prepared in 2,2-DMB (5 mL). The solution of diazo compound was added via syringe pump at a rate of 2.4 mL/h (~2 h addition time). After the diazo addition was complete, the reaction mixture was allowed to stir for an additional 0.5 h, and the solvent was removed under reduced pressure. Crude $^1$H NMR showed a 1:1 ratio of products 10:11, >98% de for both products.

The crude reaction mixture was taken up in ethanol (20 mL) and palladium on carbon (Pd/C) (0.10 g, 10% Pd) was added. The reaction mixture was purged with $H_2$ gas using a water aspirator and a balloon filled with hydrogen gas. The reaction mixture was kept under a $H_2$ atmosphere (1 atm) for 5 hours before it was passed through a pad of celite. The celite pad was further washed with diethyl ether, and the combined solutions were concentrated in vacuo. Purification by column chromatography ($SiO_2$, pentane:ether, 17:1) gave a combined mass of 125 mg (78% yield).

50 mg (31% yield) of 15 was obtained as a clear oil $R_f$=0.55 (6:1 pentane:ether) (>98% de) $[\alpha]_D^{25}$=−2.50° (c=0.4, $CHCl_3$). $^1$H NMR, $^{13}$C NMR, and FTIR were consistent with the proposed structure. HRMS (EI) m/z calcd for $[M+Na]^+$ $(C_{22}H_{26}O_2Na)^+$: 345.1825 found: 345.1825.

65 mg (40% yield) of 18 was obtained as a clear oil. $R_f$=0.57 (6:1 pentane:ether) $[\alpha]_D^{25}$=−12.4° (c=1.0, $CHCl_3$); $^1$H NMR, $^{13}$C NMR, and FTIR were consistent with the proposed structure. HRMS (EI) m/z calcd for $[M]^+$ $(C_{22}H_{24}O_2)$—: 320.1771 found: 320.1773.

(R)-methyl-4-((1R,4S)-1,2,3,4-tetrahydro-1-methylnaphthalen-4-yl)-4-phenylbutanoate (15), isolated by the above 2-step 1-pot procedure, was converted to compound 12 using the following procedure. To a cooled (0° C.) solution of 15 (40 mg, 0.12 mmol) in THF (20 mL) was added a solution lithium aluminum hydride (0.40 mL, 0.37 mmol, 1.6M in THF) dropwise over 10 mins. The reaction mixture was quenched after 2 hours by adding a few drops of water (dropwise over 15 min). After the effervescence ceased, 10% HCl was added to dissolve the aluminum salts. The reaction mixture was then extracted with diethyl ether, dried with magnesium sulfate, filtered, and concentrated in vacuo. Crude $^1$H NMR showed complete conversion to the alcohol. The crude alcohol was taken up in DCM (25 mL) cooled to 0° C., to which was added 4-bromo-phenylacetic acid (49.8 mg, 0.25 mmol) and DMAP (1.5 mg, 12.4 mmol). The reaction mixture was allowed to stir for 5 min. Then dicyclohexylcarbodiimide (0.30 mL, 0.25 mmol, 11.0M in DCM) was added dropwise, and the reaction mixture was allowed to stir overnight. A white solid formed overnight, and the slurry was filtered and washed with diethyl ether. The filterate was washed with brine, dried with magnesium sulfate, filtered and concentrated in vacuo. The crude product was purified by column chromatography ($SiO_2$, pentane:ether, 5:1) to give compound 12 (37.8 mg, 64% yield) as a white solid. The solid was recrystallized from hexanes to give white needle-like crystals suitable for X-ray analysis. $R_f$=0.74 (6:1 pentane:ether) $[[\alpha]_D^{25}$=+20.0° (c=0.4, $CHCl_3$) $^1$H NMR, $^{13}$C NMR, and FTIR were consistent with the proposed structure. HRMS (EI) m/z calcd for $[M]^+$ $(C_{21}H_{29}O_2{}^{81}Br)^+$: 478.1325 found: 478.1324.

Figure 10:
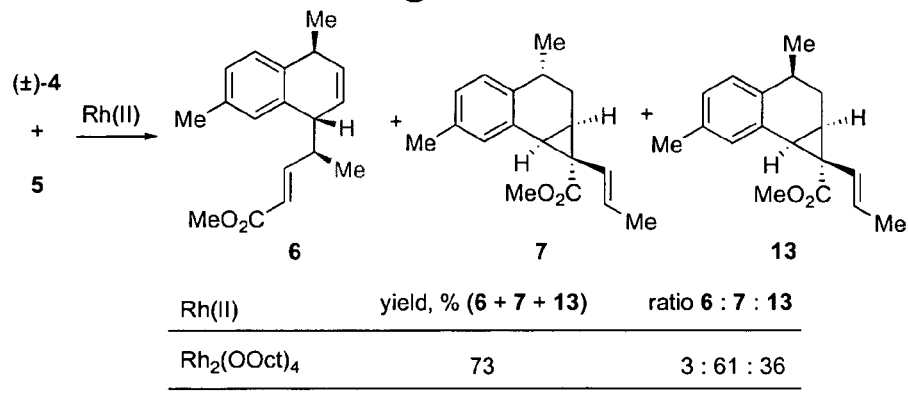
FIG. 10 is a reaction scheme in accordance with a method of the present invention showing the effect of catalyst on product distribution.

A rhodium(II) octanoate-catalyzed reaction of (+)-4 and 5 was carried out, and this reaction is described in FIG. 10.

To a flame dried 25 mL round bottom flask with a magnetic stir bar was added 1,2-dihydro-1,6-dimethylnaphthalene ((±)-4) (50.0 mg, 0.316 mmol) and $Rh_2(Oct)_4$ (9.9 mg, 0.013 mmol), dissolved in 2,2-DMB (5 mL) under argon at room temperature. In a 10 mL syringe, a solution of methyl (E)-2-diazo-4-methyl-3-butenoate (5) (88.6 mg, 0.632 mmol) was prepared in 2,2-DMB (8 mL). The solution of diazo compound was added via syringe pump at a rate of 3.9 mL/h (~2 h addition time). After the diazo addition was complete, the reaction mixture was allowed to stir for an additional 0.5 h; and the solvent was removed under reduced pressure. Crude $^1$H NMR showed a 3:61:36 ratio of products 6:7:13. Purification using column chromatography ($SiO_2$, pentane:ether, 9:1) gave an inseparable mixture of 7 and 13 (62.3 mg, 73% yield). Major diastereomer 7 and minor diastereomer 13 were characterized by $^1$H NMR. Relative configuration of minor diastereomer 13 was confirmed by nOe studies.

Figure 11:
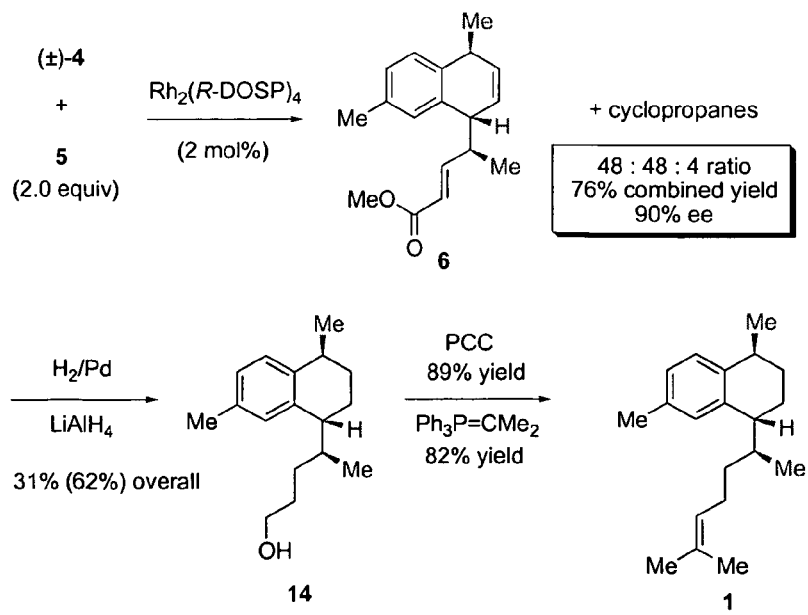
FIG. 11 is a reaction scheme for the preparation of erogorgiaene showing the use of compounds and methods of the present invention.

Erogorgiaene (1) was prepared using the procedure described in FIG. 11.

To a flame dried 25 mL round bottom flask with a magnetic stir bar was added 1,2-dihydro-1,6-dimethylnaphthalene ((±)-4) (0.20 g, 1.26 mmol) and $Rh_2(R$-$DOSP)_4$ (95.0 mg, 0.050 mmol), dissolved in 2,2-DMB (5 mL) under argon at room temperature. In a 10 mL syringe a solution of methyl (E)-2-diazo-4-methyl-3-butenoate (5) (354 mg, 2.53 mmol) was prepared in 2,2-DMB (8 mL). The solution of diazo compound was added via syringe pump at a rate of 3.9 mL/h (~2 h addition time). After the diazo addition was complete, the reaction mixture was allowed to stir for an additional 0.5 h; and the solvent was removed under reduced pressure. Crude $^1$H NMR showed a 48:48:4 ratio of products 6:7:13, >98% de for both products. To determine the yield a separate reaction was purified by column chromatography ($SiO_2$, pentane ether (9:1)) to give a mixture of 6 and 7 in 76% yield (0.234 mg) (using 0.18 mg (1.13 mmol) of 4, 0.318 mg (2.27 mmol) of 5, and 86 mg (0.046 mmol) of $Rh_2(R$-$DOSP)_4$).

The crude reaction mixture was taken up in ethanol (20 mL), and palladium on carbon (Pd/C) (0.10 g, 10% Pd) was added. The reaction mixture was pressurized with $H_2$ gas at 30 psi and allowed to shake for 4 h. The crude mixture was passed through a pad of celite and washed with diethyl ether and concentrated under reduced pressure.

The residue was dissolved in THF (15 mL) and cooled to 0° C. Lithium aluminum hydride (2.37 mL, 3.79 mmol, 1.6M in THF) was added dropwise over 5 min, and the reaction mixture was allowed to warm to room temperature over 2 h. Excess reducing agent was quenched by slow addition (dropwise) of water, and the reaction mixture was then washed with 10% aqueous hydrochloric acid. The aqueous layer was extracted with diethyl ether, and the combined organic extracts were dried using $MgSO_4$ and concentrated under reduced pressure.

Purification by column chromatography ($SiO_2$, pentane:ether (3:1)) gave a combined mass of 192.2 mg (62% yield).

96.5 mg (31% yield, from reaction enantiomer of 4; 62% yield from 4) of 14 was obtained as a clear oil. $R_f$=0.22 (3:1 pentane:ether) 90% ee by HPLC using Chiralcel OD-H, 0.7 mL/min., 1.0% 2-propanol in hexane, $t_R$=23.7 (minor) and 25.4 (major) min, UV 254 nm. $[\alpha]_D^{25}$=+36.5° (c=0.81, $CHCl_3$). $^1$H NMR, $^{13}$C NMR, and FTIR were consistent with the proposed structure. HRMS (EI) m/z calcd for $[M]^+$ $(C_{17}H_{26}O)^+$: 246.1982 found: 246.1978.

95.7 mg (31% yield) of ((1S,1aR,3R,7bR)-1a,2,3,7b-tetrahydro-3,6-dimethyl-1-propyl-1H-cyclopropa[a]naphthalen-1-yl)methanol (17)

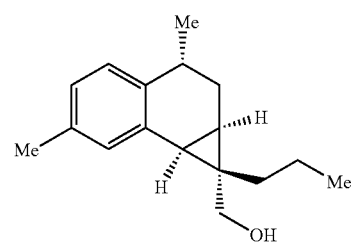

17 was obtained as a clear oil. $R_f$=0.25 (3:1, pentane:ether) $[\alpha]_D^{25}$=−87.3° (c=3.0, CHCl$_3$). $^1$H NMR, $^{13}$C NMR, and FTIR were consistent with the proposed structure. HRMS (EI) m/z calcd for [M]$^+$ (C$_{11}$H$_{24}$O)$^+$: 244.1822 found: 244.1821.

To a stirring solution of 14 (34 mg, 0.138 mmol) in DCM (15 mL) was added pyridinium chlorochromate (0.119 g, 0.552 mmol), and the reaction mixture was allowed to stir for 12 h. Celite was then added; and the reaction mixture was passed through a pad of celite/silica gel (mixture of 3:2), washed with DCM, and concentrated under reduced pressure. The residue was purified using flash chromatography (SiO$_2$, pentane:diethyl:ether (7:1)) to give (S)-4-((1S,4R)-1,2,3,4-tetrahydro-1,6-dimethylnaphthalen-4-yl)pentanal (16) (30 mg, 89% yield) as a clear oil. $R_f$=0.50 (9:1 pentane:ether) $[\alpha]_D^{25}$=+52.6° (c=0.81, CHCl$_3$). $^1$H NMR, $^{13}$C NMR, and FTIR were consistent with the proposed structure. HRMS (EI) m/z calcd for [M]$^+$ (C$_{17}$H$_{24}$O)$^+$: 244.1821 found: 244.1822.

To a yellow suspension of diisopropyltriphenylphosphonium iodide (0.212 g, 0.491 mmol) in THF (10 mL) cooled to 0° C. was added NaHMDS (0.24 mL, 0.47 mmol, 2.0 M in THF). After 5 min, a THF solution (7 mL) of aldehyde 16 (30.0 mg, 0.122 mmol) was added, and the reaction mixture was allowed to stir overnight. The reaction mixture was concentrated under reduced pressure and purified using column chromatography (SiO$_2$, hexane) to give erogorgiaene (1) (27.2 mg, 82% yield) as a clear oil. $R_f$=0.63 (pentane) $[\alpha]_D^{25}$=+21.4° (c=0.14, CHCl$_3$) ref. (Rodriguez et al., *J. Nat. Prod.*, 64:100-102 (2001), which is hereby incorporated by reference) lit. $[\alpha]_D^{25}$=+24.4° (c=3.2, CHCl$_3$) ref. (Cesati et al., *J. Am. Chem. Soc.*, 126:96-101 (2004), which is hereby incorporated by reference) $[\alpha]_D^{25}$=+40.6° (c=0.14, CHCl$_3$). $^1$H NMR and $^{13}$C NMR were consistent with the proposed structure.

Example 3

Enantioselective Syntheses of (−)-Colombiasin A and (−)-Elisapterosin B

Figure 12:
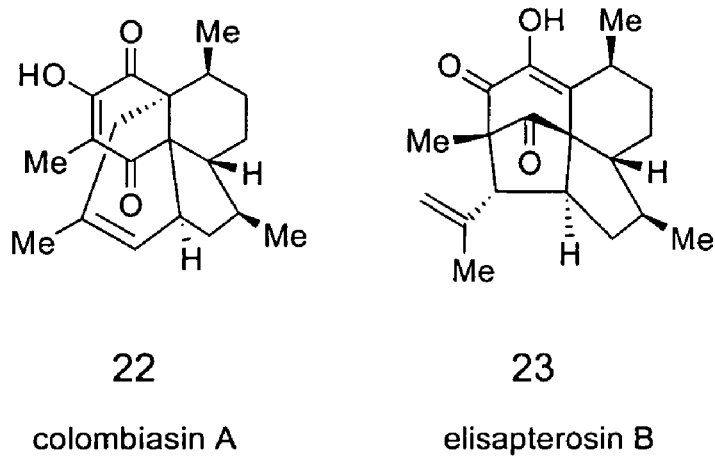
FIG. 12 is drawing showing chemical formulae of two erogorgiaene congeners that can be prepared using compounds and methods of the present invention.

In this example, we further illustrate, through the enantioselective synthesis of (−)-colombiasin A (22) and (−)-elisapterosin B (23), a general strategy for preparing erogorgiaene congeners. The structures of (−)-colombiasin A (22) and (−)-elisapterosin B (23) are set forth in FIG. 12.

Figure 13:
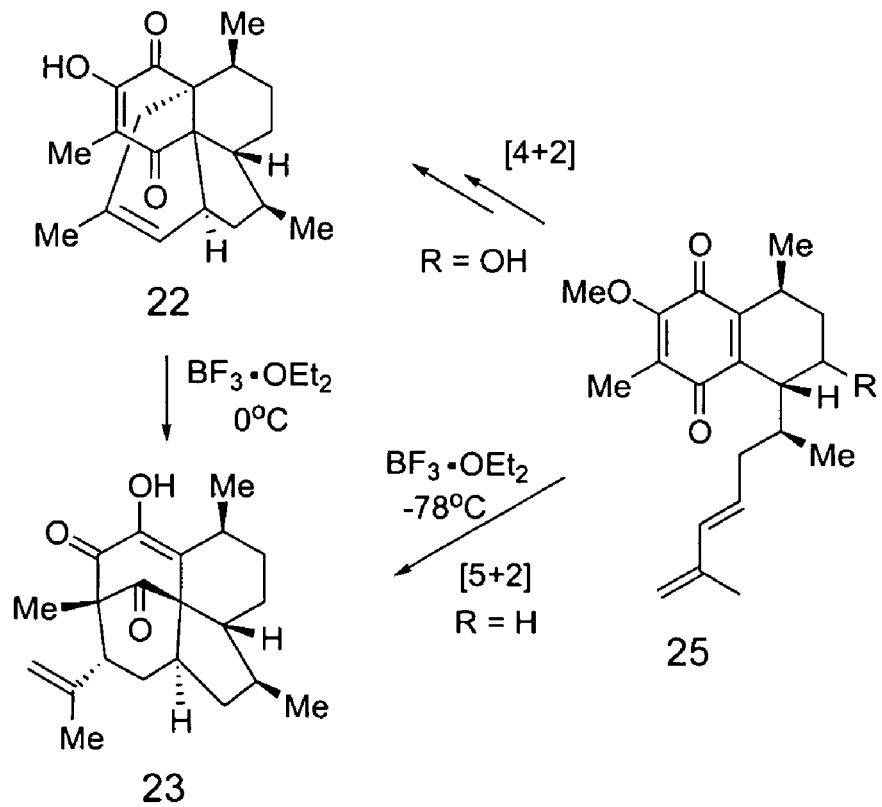
FIG. 13 is a reaction scheme showing certain prior art methodologies for the preparation of colombiasin A and elisapoterosin B.

The considerable synthetic challenges presented by the three stereocenters contained in erogorgiaene and erogorgiaene congeners have been discussed above. The problems associated with the stereochemical issues of these natural products can be readily seen in the published syntheses of (−)-colombiasin A (22) and (−)-elisapterosin B (23) (Johnson et al., *J. Am. Chem. Soc.*, 123:4475-4479 (2001); Davidson et al., *J. Am. Chem. Soc.*, 125:13486-13489 (2003); Harmata et al., *Org. Lett.*, 6:2201-2203 (2004); Harmata et al., *Org. Lett.*, 7:3581-3583 (2005); Rodriguez et al., *J. Nat. Prod.*, 67:1672-1680 (2004); Corey et al., *J. Am. Chem. Soc.*, 120:12777-12782 (1998); Davies et al., *J. Chem. Rev.*, 103:2861-2903 (2003); Davies et al., *Synthesis*, 16:2595-2608 (2004); Davies et al., *J. Org. Chem.*, 68:6126-6132 (2003); Davies et al., *Org. Lett.*, 2:4153-4156 (2000); Davies et al., *J. Am. Chem. Soc.*, 121:6509-6510 (1999); Davies et al., *Org. Lett.*, 3:1773-1775 (2001); Davies et al., *Angew. Chem. Int. Ed. Engl.*, 41:2197-2199 (2002); and Davies et al., *Org. Lett.*, 6:1769-1772 (2004), which are hereby incorporated by reference). The end game in the syntheses of these compounds has been elegantly achieved by means of cycloaddition approaches, for example, as illustrated in FIG. 13. Nicolaou demonstrated that (−)-colombiasin A could be readily prepared by an intramolecular [4+2]cycloaddition from the diene 25 (Nicolaou et al., *Angew. Chem. Int. Ed.*, 40:2482-2486 (2001); Nicolaou et al., *Chem. Eur. J.*, 7:5359-5371 (2001), which are hereby incorporated by reference), while Rychnovsky developed a rapid entry into (−)-elisapterosin B by a Lewis acid catalyzed [5+2] cycloaddition from 25 (Kim et al., *Angew. Chem. Int. Ed.*, 42:1267-1270 (2003), which is hereby incorporated by reference). Recently, Jacobsen has shown that (−)-colombiasin A can be converted into (−)-elisapterosin B by a Lewis acid catalyzed reaction, possibly occurring by a retro [4+2] cycloaddition followed by a [5+2] cycloaddition (Boezio et al., *Angew. Chem., Int. Ed.*, 44:6046-6050 (2005), which is hereby incorporated by reference).

Figure 14:
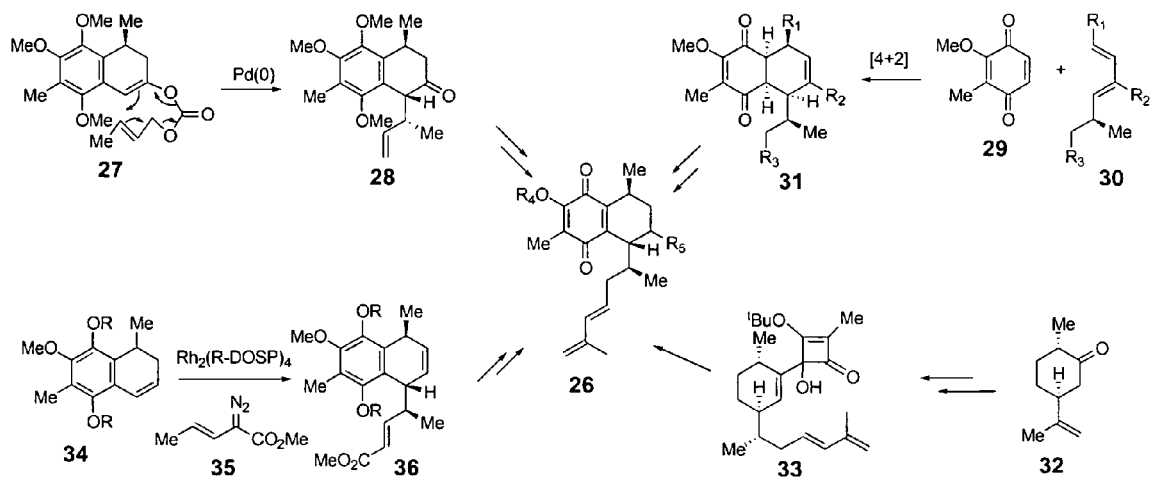
FIG. 14 is a reaction scheme showing a method of the present invention as well as certain prior art methods for generating stereocenters found in erogorgiaene congeners.

Even though the end game solution for the synthesis of (−)-colombiasin A and (−)-elisapterosin B is very elegant and efficient, the stereoselective synthesis of the three distinctive stereogenic centers has been much more challenging, as illustrated in FIG. 14. In the synthesis related to (−)-colombiasin A, three main retrosynthetic strategies have been developed. The first approach employed a Tsuji allylation from 27, but this suffered from poor regiocontrol producing a 1:2.4 mixture of the 1,3- and a 3,3-rearrangement (28) products (Nicolaou et al., *Angew. Chem. Int. Ed.*, 40:2482-2486 (2001); Nicolaou et al., *Chem. Eur. J.*, 7:5359-5371 (2001), which are hereby incorporated by reference). Furthermore, 28 is formed as the wrong diastereomer, and several additional steps were required to achieve the necessary epimerization. An alternative strategy has been an intermolecular Diels-Alder reaction of benzoquinone 29 with a diene 30. Due to the lack of stereocontrol, the exocyclic stereocenter in the diene needed to be stereospecifically introduced prior to the cycloaddition. In the initial process reported by Rychnovsky, the diastereoselectivity in the cycloaddition was low (1:1.7) (Kim et al., *Angew. Chem., Int. Ed.*, 42:1267-1270 (2003), which is hereby incorporated by reference), but, recently, Jacobsen has greatly improved this process by using chiral Lewis acids to influence the diastereoselectivity of this cycloaddition (Boezio et al., *Angew. Chem. Int. Ed.*, 44:6046-6050 (2005), which is hereby incorporated by reference). Due to the stereochemical challenges of these natural products, many groups have avoided the problem by starting their syntheses with commercially available monoterpenes (Johnson et al., *J. Am. Chem. Soc.*, 123:4475-4479 (2001); Davidson et al., *J. Am. Chem. Soc.*, 125:13486-13489 (2003); and Corey et al., *J. Am. Chem. Soc.*, 120:12777-12782 (1998), which are hereby incorporated by reference). This strategy has been recently used by Harrowven starting from the monoterpene 32 which is converted to 33 and includes a nice cascade to complete the total synthesis of (−)-colombiasin A (Harrowven et al., *Tetrahedron Lett.*, 42:8709-8711 (2001), which is hereby incorporated by reference). This approach is effective, but it does have the drawback that a different annulation strategy would have to be designed for each natural product synthesis. In this Example 3, we describe a very different approach to control the three stereocenters in these natural products. The approach is based on a "combined C—H activation/Cope rearrangement" between the vinyldiazoacetate 35 and dihydronaphthalenes 34, which, as discussed in Examples 1 and 2, generates the three stereocenters in one step.

Figure 15:
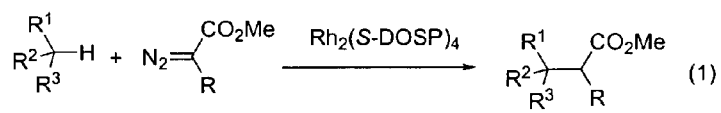
FIG. 15 is a set of two equations describing approaches to achieving the C—H functionalization by means of intermolecular C—H insertions of rhodium carbenoids.
Figure 15:
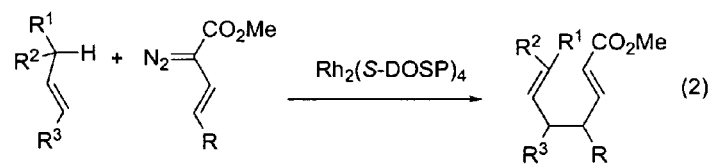

Our group has been developing new strategic reactions for organic synthesis, which are based on regioselective intermolecular C—H functionalization processes (Davies et al., *J. Chem. Rev.*, 103:2861-2903 (2003); and Davies et al., *Synthesis*, 16:2595-2608 (2004), which are hereby incorporated by reference). Our approach to achieve the C—H functionalization is by means of intermolecular C—H insertions of rhodium carbenoids. Two major variants of this theme have been discovered. The first is the direct C—H insertion which can be conducted in a highly enantioselective manner using the dirhodium tetraprolinate complex $Rh_2(S\text{-}DOSP)_4$ as catalyst (FIG. 15, equation 1). Using this reaction, equivalent transformations have been achieved to several of the classic reactions of organic synthesis, such as the aldol reaction, Mannich reaction, Michael addition, and the Claisen rearrangement. The second is the "combined C—H activation Cope rearrangement," a transformation that often occurs in >98% ee and >98% de (FIG. 15, equation 2) (Davies et al., *Proc. Natl. Acad. Sci. USA*, 101:5472-5475 (2004); and Davies et al., *J. Am. Chem. Soc.*, 126:10862-10863 (2004), which are hereby incorporated by reference). This reaction occurs during allylic C—H functionalization by vinyldiazoacetates.

Figure 16:
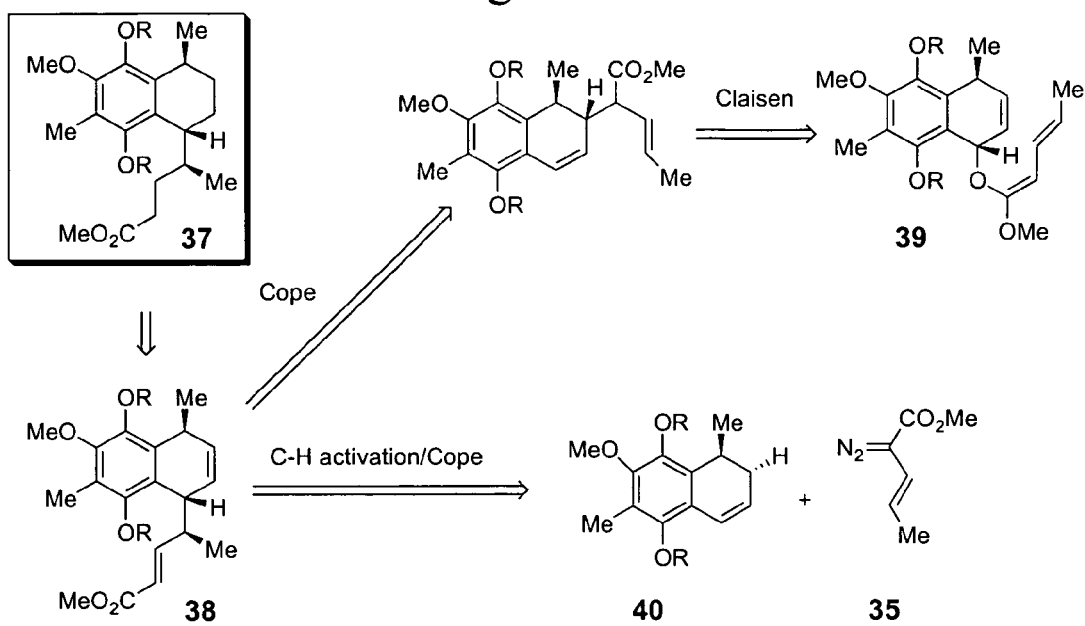
FIG. 16 is a retrosynthetic scheme showing possible ways for preparing compounds of the present invention.

The combined C—H activation/Cope rearrangement also has the potential of being a surrogate of some of the classic reactions of organic synthesis (Davies et al., *J. Org. Chem.*, 69:9241-9247 (2004), which is hereby incorporated by reference). This can be illustrated by considering a hypothetical approach, shown in FIG. 16, for the synthesis of (−)-colombiasin A that would in principle be applicable to many other members of these diterpenes. A flexible precursor to (−)-colombiasin A would be the ester 37. If 37 is derived from the diene 38, a hypothetical approach to generate 38 with controlled stereochemistry would be a tandem Clasien rearrangement/Cope rearrangement from 39. Both reactions would be expected to proceed through a chair transition state where the ester stereogenic center in 39 would dictate the stereochemistry in the formation of the two new stereogenic centers in 38. This scheme has to be considered hypothetical because there would be no driving force for the Cope rearrangement (Davies et al., *Proc. Natl. Acad. Sci. USA*, 101:5472-5475 (2004), which is hereby incorporated by reference). The "combined C—H activation/Cope rearrangement" would be an equivalent of this hypothetical reaction, as illustrated in the conversion of 40 to 38.

In Examples 1 and 2, we demonstrated that the combined C—H activation/Cope rearrangement can be effectively applied to the rapid construction of (+)-erogorgiaene. The C—H functionalization with the vinyldiazoacetate is especially impressive because it is an enantiodivergent step. One enantiomer of the dihydronaphthalene undergoes the C—H activation/Cope rearrangement while the other enantiomer undergoes a cyclopropanation. Completion of the synthesis of (+)-erogorgiaene was readily achieved in four additional steps from the product of the C—H activation/Cope rearrangement. As the C—H functionalization begins at a site well away from the aromatic ring, we made the hypothesis that this reaction would be little influenced by the aromatic ring functionality. In this Example 3, we demonstrate that a highly oxygenated aromatic ring is equally compatible with this carbenoid chemistry, leading to a very direct access to (−)-colombiasin A and (−)-elisapterosin B.

Figure 17:
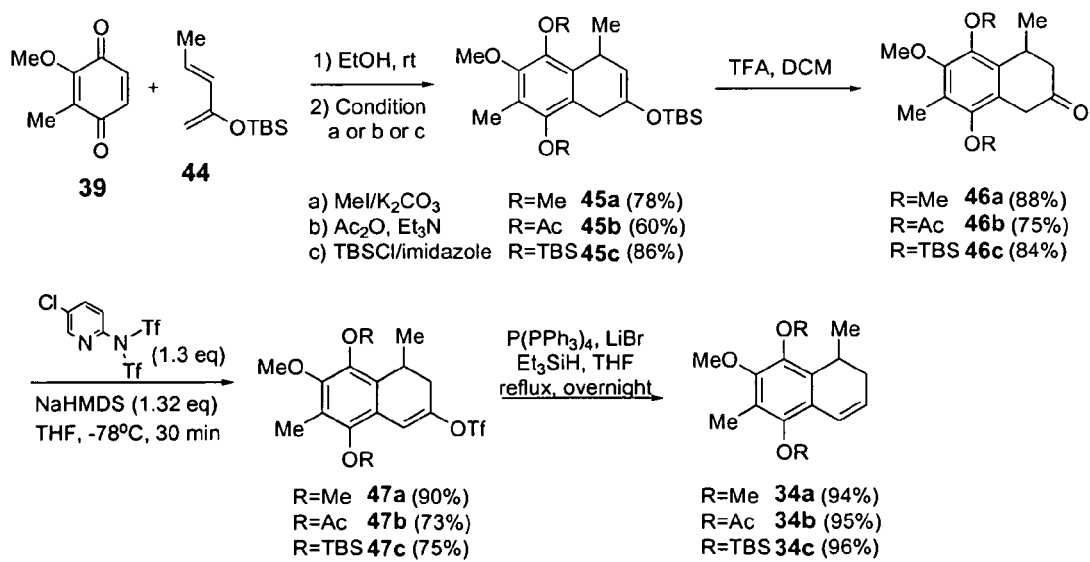
FIG. 17 is a reaction scheme for the preparation of various cyclohexene compounds that can be used in a method of the present invention.

As shown in FIG. 17, three dihydronaphthalenes with different protecting groups, methyl (34a), acetyl (34b) and t-butyldimethylsilyl (34c) were chosen as appropriate substrates for the combined C—H activation/Cope rearrangement. The synthesis of 34 started from the p-quinone 29 following a [4+2]cycloaddition sequence described by Nicolaou (Nicolaou et al., *Angew. Chem., Int. Ed.*, 40:2482-2486 (2001); Nicolaou et al., *Chem. Eur. J.*, 7:5359-5371 (2001), which are hereby incorporated by reference). Reaction of the quinone 29 with the diene 44 generated the cycloadduct which on isomerization to the corresponding quinol could be trapped under different conditions to afford the dimethyl derivative ether 45a, the diacetyl derivative 45b, and the disilyl derivative 45c. Acidic hydrolysis of the resulting TBS-enol ether in 45 gave rise to the ketone 46 in good yields. Initially, we investigated utilizing a reduction/elimination strategy to form the C=C double bond of 34 from the β-tetralone 46, but this gave a mixture of double bond isomers. The overall transformation could be achieved through initially converting the b-tetralone 46 to the corresponding vinyl triflate 47 using Comins' reagent (Comins et al., *Tetrahedron Lett.*, 33(42), 6299-6302 (1992), which is hereby incorporated by reference), before carrying out a palladium catalyzed reductive coupling (Scott et al., *J. Am. Chem. Soc.*, 108:3033-3040 (1986), which is hereby incorporated by reference).

Figure 18:
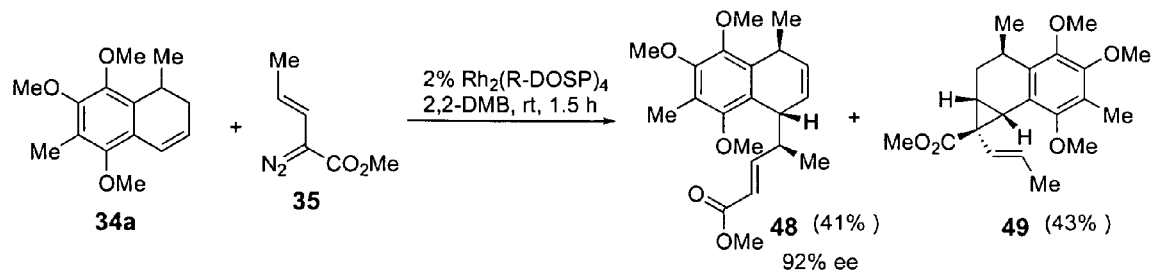
FIG. 18 is a reaction scheme in accordance with a method of the present invention.

With quantities of the three dihydronaphthalenes 34 in hand, the key rhodium carbenoid step was examined, as shown in FIG. 18. From the conception of the project, it was proposed that the functionality on the aromatic ring would not interfere with the combined C—H activation step. This was definitely the case with the dimethoxy derivative 34a as the $Rh_2(R\text{-}DOSP)_4$ catalyzed reaction of 34a with the vinyldiazoacetate 35 gave a 1:1 mixture of the C—H functionalization product 48 and the cyclopropane 49 as single diastereomers. Furthermore, the C—H functionalization product 48 was formed with the correct relative stereochemistry for the natural products and in 92% ee.

Figure 19:
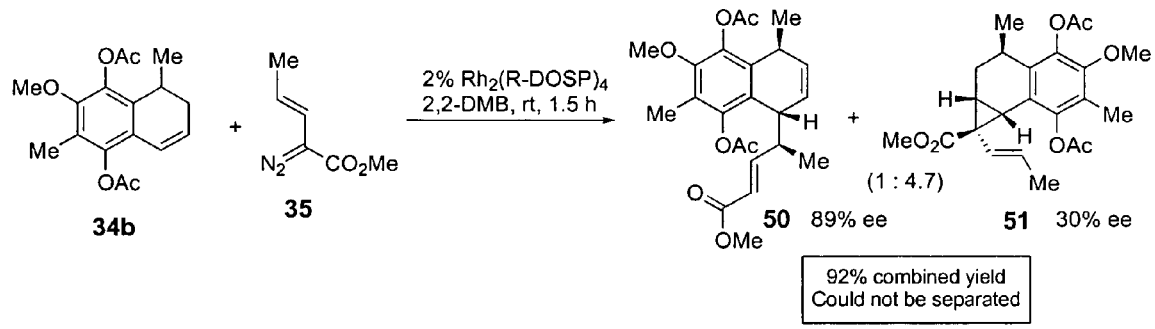
FIG. 19 is a reaction scheme in accordance with a method of the present invention.

As shown in FIG. 19, the C—H functionalization chemistry of the diacetyl derivative 34b gave a surprising result. The $Rh_2(R\text{-}DOSP)_4$ catalyzed reaction between 35 and 34b proceeded in high yield (92%) but the 1:4.7 ratio of the C—H functionalization product 50 to the cyclopropane 51 was much different to the 1:1 ratio of the reaction with 34a. Even so, both 50 and 51 were produced with very high diastereoselectivity (>95% de), but the enantioselectivity for the C—H functionalization product 50 was 89% ee, while the cyclopropane 51 was formed in only 30% ee. This result is not consistent with our previous observations and is indicative that the acetoxy groups interferes with the chiral discrimination by the prolinate catalyst on the cyclopropanation although the C—H functionalization selectivity is not markedly changed. A possible explanation for this strange effect is that the acetoxy group coordinates to the carbenoid prior to the cyclopropanation event, and this interferes with the chiral influence of the catalyst. Ester coordination to a carbenoid has been implicated in asymmetric cyclopropanations with chiral ester auxiliaries (Davies et al., *Org. Lett.*, 5:1403-1406 (2003), which is hereby incorporated by reference), and the presence of methyl benzoate as an additive greatly enhances the turnover numbers of rhodium catalyzed cyclopropanations (Davies et al., *J. Am. Chem. Soc.*, 115:9468-9479 (1993), which is hereby incorporated by reference).

Figure 20:
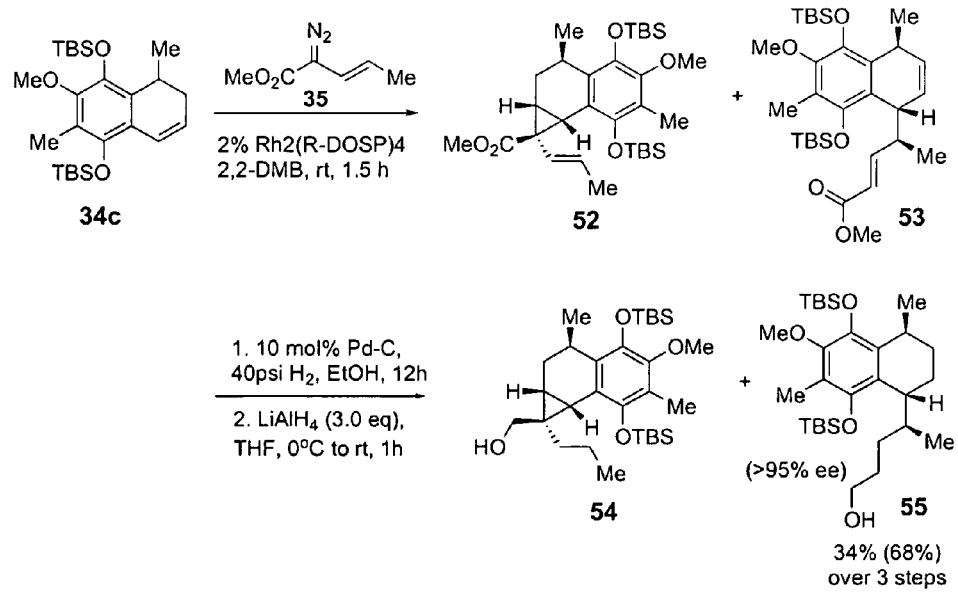
FIG. 20 is a reaction scheme in accordance with a method of the present invention.

In contrast to the diacetoxy system, the disilyl derivative 34c was an exceptional substrate for the combined C—H activation/Cope rearrangement, as shown in FIG. 20. The $Rh_2(R\text{-}DOSP)_4$ catalyzed reaction of 35 with 34c gave a 1:1 mixture of the C—H functionalization product 52 and the cyclopropane 53. Since the two products could not be separated at this stage, the mixture was hydrogenated and then reduced to the alcohols 54 and 55. The desired C—H functionalization product 55 was isolated in 34% yield (68% in theory) as a single diastereomer in >95% ee over three steps.

Figure 21:
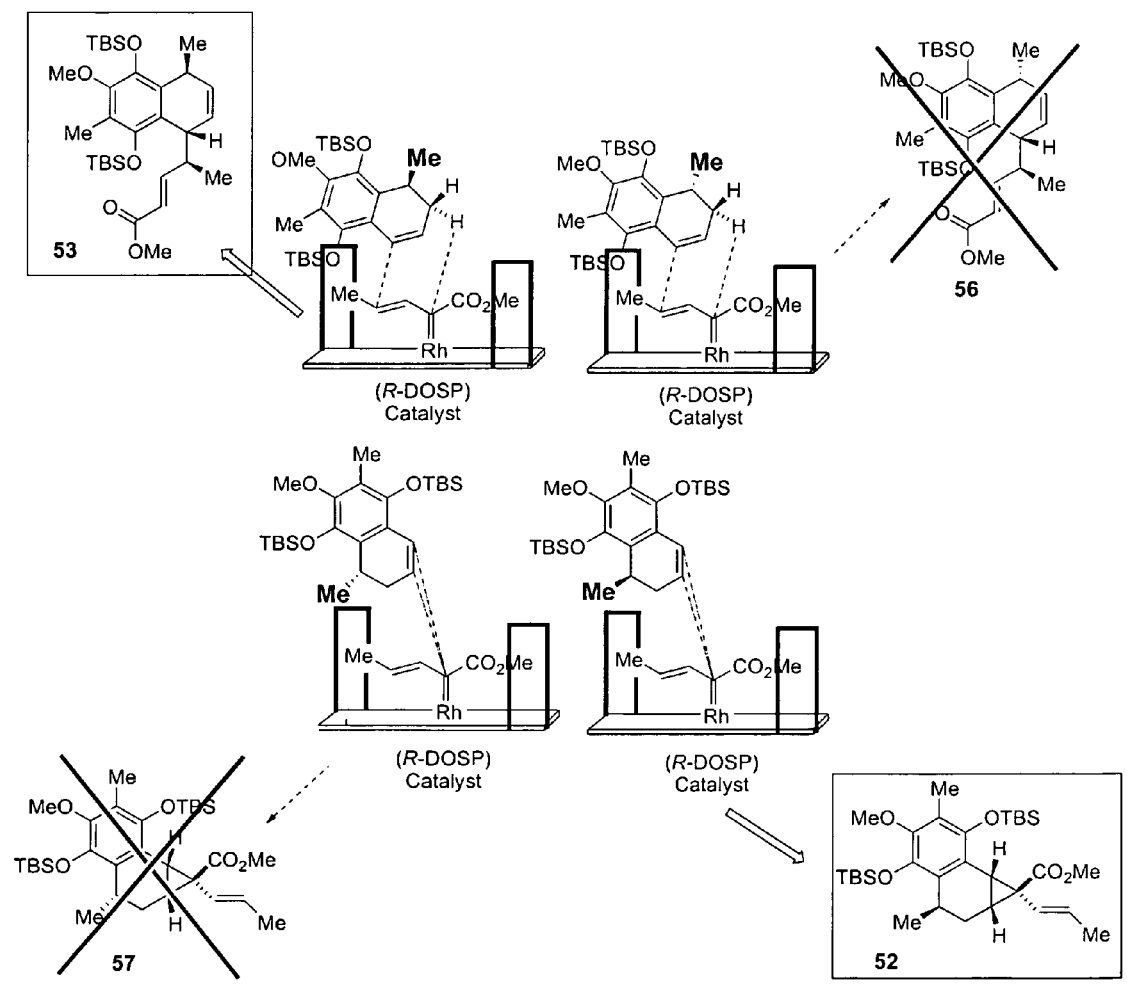
FIG. 21 is a stereochemical analysis for combined C—H activation/Cope rearrangement strategy employed in a method of the present invention.

The enantiomer differentiation in these reactions can be rationalized as illustrated in FIG. 21. Excellent predictive models have been developed for both the rhodium prolinate catalyzed C—H activation/Cope rearrangement (Davies et al., *J. Am. Chem. Soc.*, 126:10862-10863 (2004), which is hereby incorporated by reference) and the cyclopropanation (Nowlan et al., *J. Am. Chem. Soc.*, 125:15902-15911 (2003), which is hereby incorporated by reference). The chiral catalysts are considered to adopt a $D_2$ symmetric arrangement and can be viewed simply with a blocking group in the front and another in the back. Applying these models to the 4-methyl-1,2-dihydronaphthalenes as substrates leads to an interesting prediction. The matched enantiomer for the C—H activation/Cope rearrangement is opposite to the matched enantiomer for the cyclopropanation. Consequently, a situation exists for enantiomer differentiation, in which one enantiomer preferentially undergoes the C—H activation/Cope rearrangement, while the other undergoes cyclopropanation. From a practical perspective, this is even better than kinetic resolution because the complex dihydronaphthalene can be used as the limiting agent.

Figure 22:
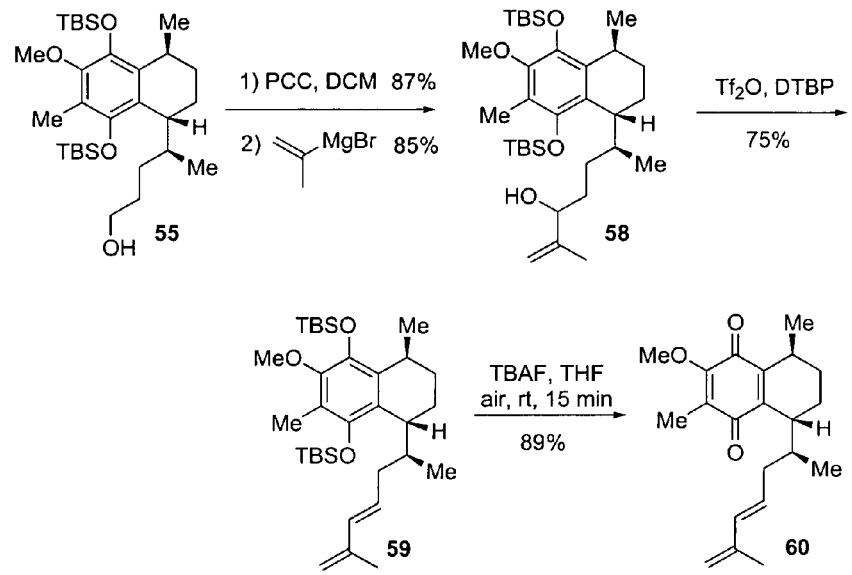
FIG. 22 is a reaction scheme showing the conversion of a compound of the present invention to other compounds that can be used in the preparation of erogorgiaene congeners.

Although both dihydronaphthalene 34a and 34c gave excellent results in the C—H activation/Cope rearrangement, 34c was used to complete the total synthesis since it would be easier to unveil the quinone moiety by deprotection of TBS ethers rather than methyl ethers. Thus, conversion of the alcohol 55 to the key diene 60 was achieved using very standard steps, as illustrated in FIG. 22. PCC oxidation of 55 followed by a Grignard addition generated the allylic alcohol 58. Conversion of 58 to the triflate followed by elimination generated the diene 59, which was readily desilylated and air oxidized to the quinone 60.

Figure 23:
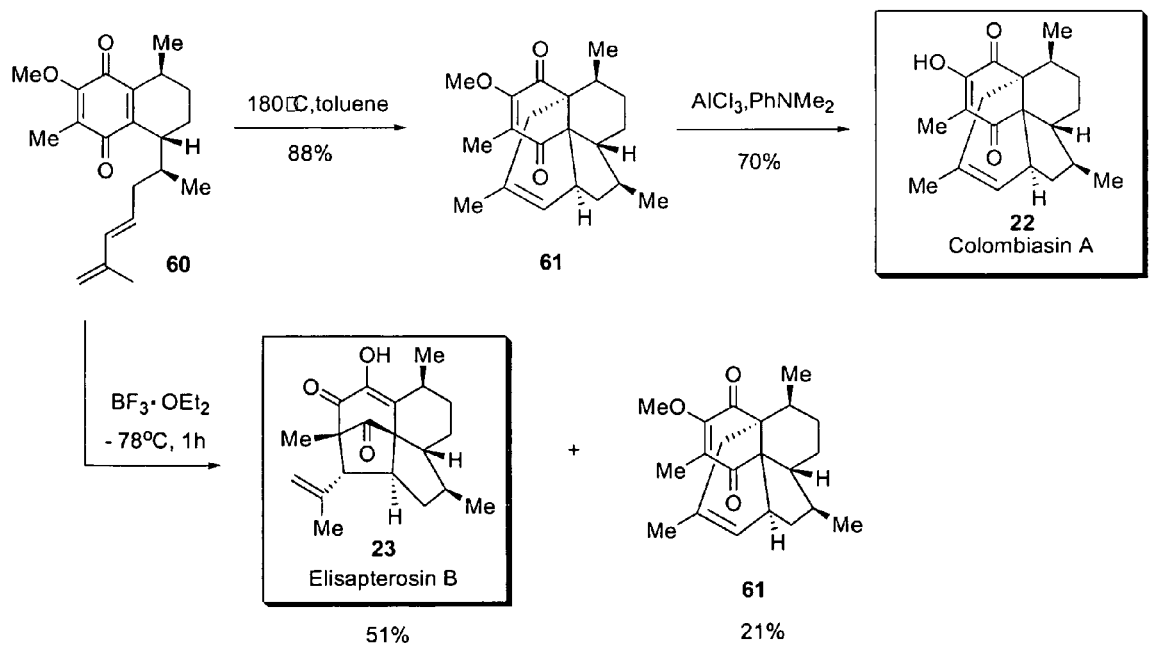
FIG. 23 is a reaction scheme showing further steps which can be employed to produce erogorgiaene congeners.

Kim and Rychnovsky have previously shown that the diene 60 can be converted to (−)-colombiasin A by an intramolecular Diels-Alder reaction, while treatment of 60 with boron trifluoride etherate generates (−)-elisapterosin B by means of a [5+2] cycloaddition (Kim et al., *Angew. Chem., Int. Ed.*, 42:1267-1270 (2003), which is hereby incorporated by reference). Thus, when diene 60 was heated at 180° C. in toluene, (−)-colombiasin A methyl ether (61) was isolated in 88% yield, as illustrated in FIG. 23 (Nicolaou et al., *Angew. Chem., Int. Ed.*, 40:2482-2486 (2001); and Nicolaou et al., *Chem. Eur. J.*, 7:5359-5371 (2001), which are hereby incorporated by reference). The total synthesis of (−)-colombiasin A (22) was completed by demethylation of 61 with $AlCl_3$ (Kim et al., *Angew. Chem., Int. Ed.*, 42:1267-1270 (2003), which is hereby incorporated by reference). Exposing diene 60 to boron trifluoride etherate at −78° C. for 1 h resulted in a [5+2] cycloaddition to give (−)-elisapterosin B in 51% yield. Under these conditions (−)-colombiasin A methyl ether 61 was generated as a side product in 21% yield. The spectral data for (−)-colombiasin A and (−)-elisapterosin B were in full agreement with the literature data.

Example 4

Figure 24:
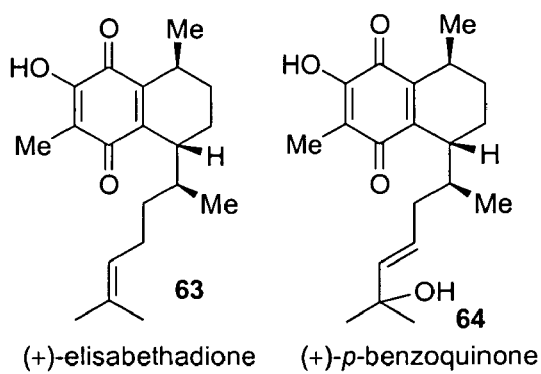
FIG. 24 is drawing showing chemical formulae of two erogorgiaene congeners that can be prepared using compounds and methods of the present invention.

Enantioselective Syntheses of the Reported Structure of (+)-Elisabethadione and a (+)-p-Benzoquinone Natural Product In this example, we further illustrate, through the enantioselective syntheses of reported structure of (+)-elisabethadione (63) and a (+)-p-benzoquinone natural product (64), the methods of the present invention for preparing erogorgiaene congeners. The structures of (+)-elisabethadione (63) and a (+)-p-benzoquinone natural product (64) are set forth in FIG. 24.

(+)-Elisabethadione (63) was isolated from the marine organism *P. elisabetha*, collected from the Florida Keys, by Kerr and co-workers (Ata et al., *Tetrahedron*, 59:4215-4222 (2003), which is hereby incorporated by reference). Its gross structure was assigned on the basis of detailed NMR analysis, but its stereochemistry was assumed by analogy to other members of this class of biogenetically related natural products (Ata et al., *Tetrahedron Lett.*, 41:5821-5825 (2000), which is hereby incorporated by reference). Anti-inflammatory assays indicate that elisabethadione is more potent than the related and commercially used natural products, the pseudopterosins (Look et al., *J. Org. Chem.*, 51:5140-5145 (1986); Look et al., *J. Proc. Natl. Acad. Sci. USA*, 83:6238-6240 (1986); and Roussis et al., *J. Org. Chem.*, 55:4916 (1990), which are hereby incorporated by reference).

Figure 25:
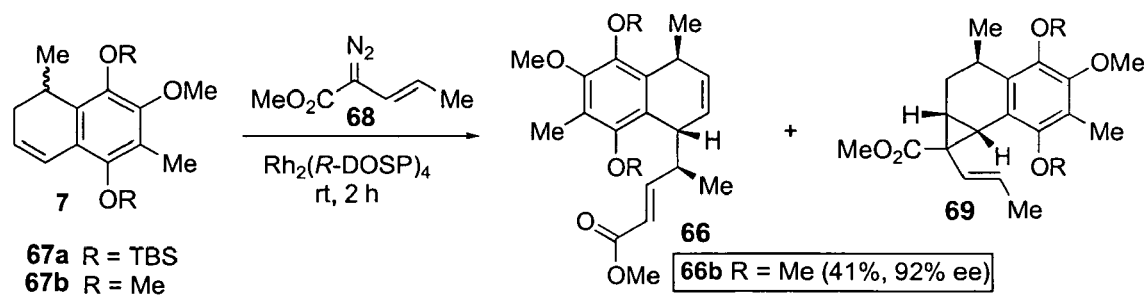
FIG. 25 is a reaction scheme in accordance with a method of the present invention.

Our synthesis of the assigned structure of elisabethadione (63) began with the previously described combined C—H activation/Cope rearrangement of the dihydronaphthalene 67b with the vinyldiazoacetate 68, as shown in FIG. 25. The $Rh_2(R$-$DOSP)_4$ catalyzed reaction of 67b and 68 gave a 1:1 mixture of the C—H functionalization product 66b (41% yield, 92% ee, enantiomeric excess was determined from the alcohol 65b) and the cyclopropane 69b (43% yield) as single diastereomers. In this key step, the correct configuration of the three stereocenters in 63 was prepared.

Figure 26:
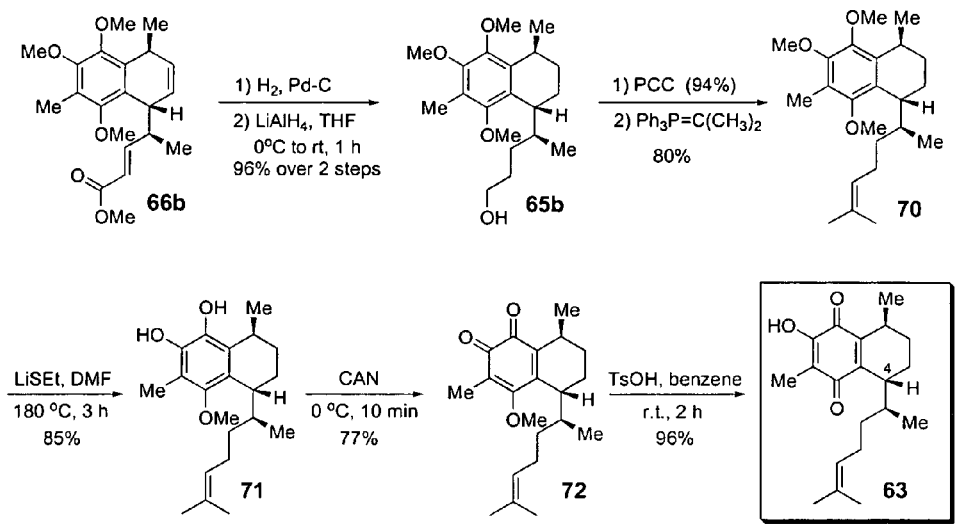
FIG. 26 is a reaction scheme showing the conversion of a compound of the present invention to an erogorgiaene congener.

The C—H functionalization product 66b is well suited for further elaboration to 63, as illustrated in FIG. 26. The 1,5-diene in 66b was hydrogenated, and then the ester group was reduced to the alcohol 65b in 96% yield over two steps. Oxidation of 65b with PCC followed by a Wittig reaction on the resultant aldehyde furnished the alkene 70. Having installed the side chain, the next operation was the oxidation of the aromatic ring to the quinone. Several initial attempts for the demethylation ($BBr_3$) and the oxidative demethylation ($(PhI(OAc))_2$ (Tohma et al., *Tetrahedron Lett.*, 42:6899-6902 (2001), which is hereby incorporated by reference); AgO/$HNO_3$ (Snyder et al., J. Am. Chem. Soc., 94:227-231 (1972); Nicolaou et al., *Angew. Chem., Int. Ed.*, 40:2482-2486 (2001); and Nicolaou et al., *Chem. Eur. J.*, 7:5359-5371 (2001), which are hereby incorporated by reference)) of 70 failed. Fortunately, heating the compound 70 with lithium ethanethiolate in DMF at 180° C. for 3 h resulted in the formation of the bisphenol 71 in 85% yield (Dehmel et al., *Org. Lett.*, 3:3579-3582 (2001), which is hereby incorporated by reference). Oxidation of 71 with cerium ammonium nitrate followed by demethylation and bond reorganization of the resultant red ortho-quinone 72 under acidic conditions gave 63, the assigned structure of elisabethadione, in 96% yield as a yellow oil.

Figure 27:
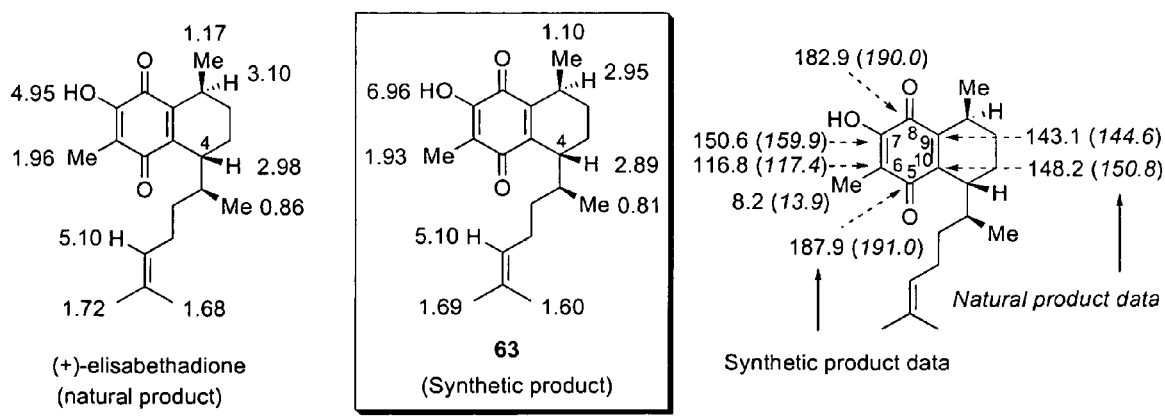
FIG. 27 is a compilation of NMR data obtained from an erogorgiaene congener produced using a method of the present invention and from a naturally-occurring erogorgiaene congener.

Contrary to our expectations, the reported $^1H$ NMR and $^{13}C$ NMR data for the natural product (+)-elisabethadione, while similar, were different from our synthetic compound 63, as summarized in FIG. 27. The NMR, IR, and HRMS data indicated that the synthetic material had the same number of protons, carbons, and molecular weight as the natural material. The specific rotation of the synthetic material (+278, c=0.58, $CHCl_3$) was quite different from the natural product (+93). On the basis of this data, either the assigned structure of the natural material or our synthetic material is incorrect. Another possibility could be errors in the reported data for the natural material. Unfortunately, it was not possible to evaluate this possibility because neither an authentic sample nor the original NMR spectra of the natural product are available.

The most convincing method to determine whether the synthetic material had the assigned structure would be X-ray crystallographic analysis. Unfortunately, we were unable to prepare a crystal suitable for X-ray analysis. The nOe studies also proved inconclusive. Therefore, a re-analysis was made of the synthetic scheme to 63 to determine if at any stage, an unexpected diastereomer could conceivably be formed. Five steps in the procedure set forth in FIG. 26 were identified to have the potential for the introduction of the wrong stereochemistry. The first was the combined C—H activation/

Cope rearrangement to form 66b. This was unlikely to be a problem because the enantiodivergent step to form 66b has been reliable with a range of substrates (Davies et al., *J. Am. Chem. Soc.*, 128:2485-2490 (2006); and Davies et al., *Angew. Chem., Int. Ed.*, 44:1733-1735 (2005), which are hereby incorporated by reference). This included the generation of the siloxy derivative, which has been successfully converted to (−)-colombiasin A and (−)-elisapterosin B, as reported in Example 3. The unsaturated ester in 66b has a potentially epimerizable center at the γ position, and so isomerization might have occurred under the hydrogenation conditions. The harsh conditions of the demethylation of 70 to 71 (LiSEt, 180° C.) could have caused an isomerization to occur, although no obvious pathway is apparent. Finally, the formation of the ortho-quinone 72 and its conversion to the para-quinone 63 could have caused isomerization because the quinones 72 and 73 do have potentially epimerizable centers. None of these potential epimerizations, however, is likely because there does not appear to be a driving force for a complete isomerization, especially as the tetrahydronaphtha-lene is already trans disubstituted.

Figure 28:
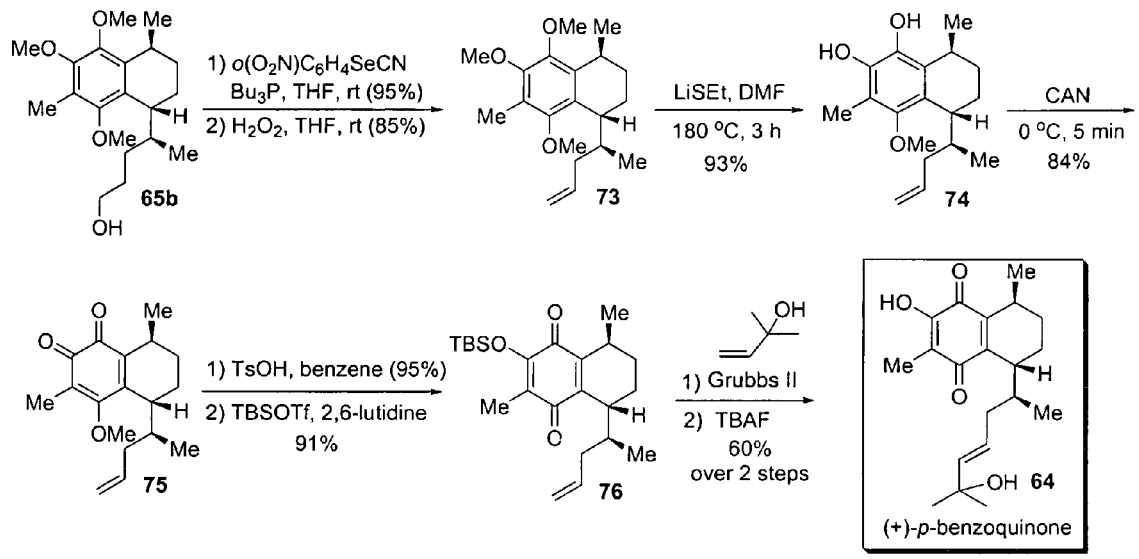
FIG. 28 is a reaction scheme showing the conversion of a compound of the present invention to an erogorgiaene congener.
Figure 29:
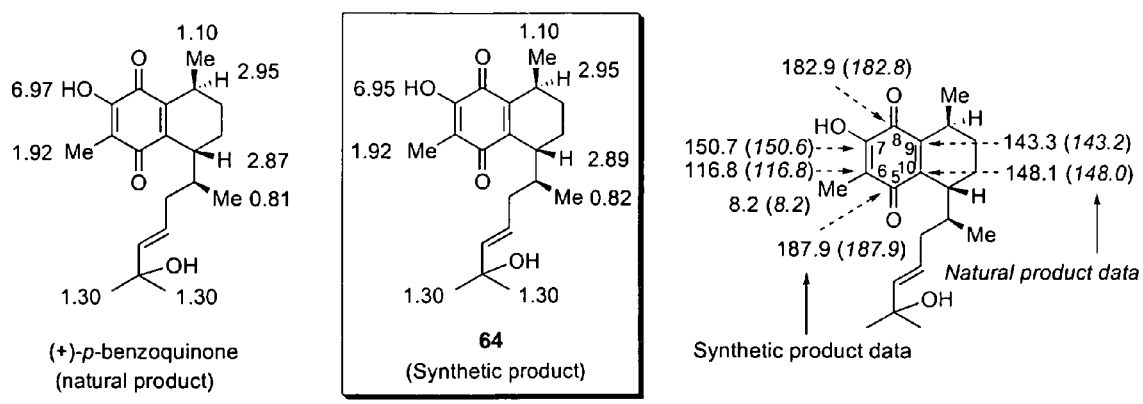
FIG. 29 is a compilation of NMR data obtained from an erogorgiaene congener produced using a method of the present invention and from a naturally-occurring erogorgiaene congener.

In order to confirm the proposed configuration of the synthetic material as 63, the total synthesis of a second related natural product, the (+)-p-benzoquinone 64, was conducted using all of the potentially epimerizable steps that has been used in the synthesis of 63. The general outline of the synthesis is shown in FIG. 28. The synthesis started from the primary alcohol 65b, the same intermediate used in the synthesis of compound 63. The terminal alkene 73 was generated by application of Grieco's selenoxide introduction/elimination procedure (Grieco et al., *J. Org. Chem.*, 41:1485-1486 (1976), which are hereby incorporated by reference). Then performing a similar sequence as was used in the synthesis of 63, 73 was converted to the quinone 76. Selective demethylation of 73 to form the bisphenol 74, followed by oxidation with ceric ammonium nitrate gave the ortho quinone 75 in 84% yield. The subsequent isomerization of the ortho quinone 75 gave the para quinone, which was then protected by a TBS group to form 76 in 91% yield. Completion of the synthesis proceeded in a straightforward fashion. Installation of the allylic alcohol by a cross-metathesis reaction catalyzed by the Grubbs second-generation ruthenium catalyst, using Jacobsen's strategy (Boezio et al., *Angew. Chem. Int. Ed.*, 44:6046-6050 (2005), which is hereby incorporated by reference), followed by deprotection of the siloxy group afforded the natural product 64 in 60% yield over two steps. The spectral data of synthetic and natural (+)-p-benzoquinone 64 were in complete accord, as shown in FIG. 29 (Rodriguez et al., *Tetrahedron*, 56:9015-9023 (2000), which is hereby incorporated by reference). Furthermore, there was excellent agreement in the $^1$H NMR and $^{13}$C NMR data for the bicyclic portion of the synthetic material of 63, the synthetic material of 64, and the natural material of 64. Assuming that the natural product 64 is correctly assigned, these results imply that the assigned structure of (+)-elisabthadione is incorrect or the reported spectral data for elisabethadione contain errors. Experimental details for the reactions described in this Example 4 are set forth in Example 5.

Example 5

Experimental Details for Enantioselective Synthesis of the Reported Structure of (+)-Elisabethadione and a (+)-D-Benzoquinone Natural Product This Example 5 sets forth the experimental details for the reactions described in Example 4.

All reactions were carried out under an atmosphere of argon in oven-dried glassware with magnetic stirring. Low temperature (−78° C.) was maintained using dry ice/acetone. Hexanes, THF, DCM, $CH_3CN$ and $Et_2O$ were purified by passage through a bed of activated alumina. Purification of reaction products was carried out by flash chromatography using silica gel 60 (230-400 mesh). $^1$H NMR spectra were measured at 300, 400, or 500 MHz spectrometers and are reported in ppm using TMS as an internal standard (TMS at 0.00 ppm). Data reported as (s=singlet, d=doublet, t=triplet, q=quartet, m=multiplet, br=broad; coupling constant(s) in Hz; integration). $^{13}$C NMR spectra were recorded at 75 or 125 MHz spectrometer and reported in ppm using solvent as an internal standard ($CDCl_3$ at 77.0 ppm).

(S,2E)-methyl 4-((1S,4R)-1,4-dihydro-5,7,8-trimethoxy-1,6-dimethylnaphthalen-4-yl)pent-2-enoate (66b) was prepared using the following procedure. A solution of methyl vinyl diazoacetate 68 (3.40 g, 24.2 mmol, 3.0 equiv) in dry degassed 2,2-dimethylbutane (20 mL) was added by syringe pump over a 1 h period at room temperature to a solution of dihydronaphthalene 67b (2.00 g, 8.1 mmol) and $Rh_2(R$-DOSP$)_4$ (306 mg, 0.16 mmol, 0.02 equiv.) in dry degassed 2,2-dimethylbutane (30 mL). Once the addition had finished, the brown solution was stirred at room temperature for an additional 30 min. The solvent was removed under vacuum to give a brown gum. Purification by column chromatography on silica gel (eluting with 7% to 10% ether/pentane) gave 66b (1.19 g, 41%) along with cyclopropane 69b (1.27 g, 43%). $R_f$ 0.36 (7:1 pentane/ether); $^1$H NMR (500 MHz, $CDCl_3$): δ 7.20 (dd, J=16.0, 6.0 Hz, 1H), 5.85 (dd, J=16.0, 2.0 Hz, 1H), 5.84 (m, 1H), 5.49 (ddd, J=10.0, 4.0, 2.0 Hz, 1H), 3.83 (s, 3H), 3.82 (s, 3H), 3.76 (s, 3H), 3.72 (s, 3H), 3.71 (m, 1H), 3.45 (m, 1H), 3.12 (m, 1H), 2.19 (s, 3H), 1.27 (d, J=7.0 Hz, 3H), 0.55 (d, J=7.0 Hz, 3H); $^{13}$C NMR (75 MHz, $CDCl_3$): δ 167.5, 154.3, 152.2, 150.4, 147.4, 133.0, 132.9, 124.9, 123.3, 121.2, 119.7, 60.7, 60.3, 60.0, 51.4, 40.6, 39.3, 30.4, 23.9, 12.0, 9.3; IR (neat) 2953, 1723, 1651, 1462, 1318, 1079, 1015 cm$^{-1}$; HRMS m/z (EI) calculated for $C_{21}H_{28}O_5Na$ 383.1829 found 383.1837.

(S)-4-((1S,4R)-1,2,3,4-tetrahydro-5,7,8-trimethoxy-1,6-dimethylnaphthalen-4-yl)pentan-1-ol (65b) was prepared using the following procedure. To a solution of ester 66b (944 mg, 2.62 mmol) in ethanol (50 mL) was added 5% palladium on carbon (about 50 mg). The suspension was placed on a Parr Hydrogenator at 45 psi for 3 h. The reaction mixture was filtered through a pad of Celite™ on silica gel. The filtrate was concentrated in vacuo to give a clear gum which was used without further purification for the next step. The crude product was dissolved in dry tetrahydrofuran (60 mL) and cooled to 0° C. Lithium aluminium hydride (5.24 mL, 1.0 M in THF, 5.24 mmol, 2.0 equiv) was added, and the mixture stirred at room temperature for 1 h. Water (20 mL) was added dropwise followed by ether (40 mL). The organic layer was separated, and the aqueous layer was extracted with ether (20×4 mL). The combined organic layers were dried over $Na_2SO_4$ and concentrated in vacuo. The residue was purified by column chromatography on silica gel (eluent 20% to 33% ether/pentane) to give 65b as a clear gum (847 mg, 94% over two steps, 92% ee). The enantiomeric excess of 65b was determined by HPLC (Daicel Chiralcel OD-H, hexanes/i-PrOH=99:1, flow rate=0.7 mL/min) $t_r$=21.3 min (major), $t_r$=23.3 min (minor). $[\alpha]^{25}_D$=6.4° (c=1.4, $CHCl_3$); $^1$H NMR (500 MHz, $CDCl_3$): δ 3.85 (s, 3H), 3.80 (s, 3H), 3.64 (s, 3H), 3.61 (m, 2H), 3.16 (m, 1H), 2.85 (m, 1H), 2.17 (s, 3H), 1.92-2.03 (m, 2H), 1.75-1.79 (m, 2H), 1.66 (m, 1H), 1.58 (m, 1H), 1.45 (m, 1H), 1.35 (m, 2H), 1.14 (d, J=7.0 Hz, 3H), 0.75 (d, J=7.0 Hz, 3H), OH signal was not observed; $^{13}$C NMR (125 MHz, CDCl$_3$): δ 152.7, 149.5, 147.1, 134.8, 128.6, 122.2, 63.3, 60.5, 60.2, 59.9, 37.4, 35.4, 31.2, 30.6, 27.0, 26.4, 23.2, 18.5, 18.1, 9.4; IR (neat) 2932, 1403, 1071, 731 cm$^{-1}$; HRMS (EI) calcd for C$_{20}$H$_{32}$O$_4$Na [M]$^+$, required m/z: 359.2193, found m/z: 359.2197.

(S)-4-((1S,4R)-1,2,3,4-tetrahydro-5,7,8-trimethoxy-1,6-dimethylnaphthalen-4-yl)pentanal was prepared using the following procedure. To a solution of 65b (210 mg, 0.62 mmol) in dry DCM (20 mL), pyridinium chlorochromate (202 mg, 0.94 mmol, 1.5 equiv) was added in one portion at 0° C. The reaction mixture was stirred at room temperature for 1.5 h and then was diluted with ether (100 mL). The crude reaction mixture was filtered through a plug of celite on silica gel. The filtrate was concentrated in vacuo to give a yellow oil. Purification by column chromatography on silica gel (eluting with 13% ether/pentane) gave (S)-4-((1S,4R)-1,2,3,4-tetrahydro-5,7,8-trimethoxy-1,6-dimethylnaphthalen-4-yl)pentanal as a clear gum (194 mg, 94%). $^1$H NMR (500 MHz, CDCl$_3$) δ 9.74 (br s, 1H), 3.85 (s, 3H), 3.80 (s, 3H), 3.64 (s, 3H), 3.16 (m, 1H), 2.83 (m, 1H), 2.32-2.50 (m, 2H), 2.17 (s, 3H), 1.90-2.01 (m, 2H), 1.78 (m, 2H), 1.56-1.69 (m, 2H), 1.48 (m, 1H), 1.40 (d, J=7.0 Hz, 3H), 0.78 (d, J=7.0 Hz, 3H); $^{13}$C NMR (75 MHz, CDCl$_3$) δ 203.3, 152.9, 149.7, 147.1, 134.7, 127.9, 122.3, 60.5, 60.1, 59.9, 42.4, 37.5, 35.6, 27.4, 27.0, 26.4, 23.2, 18.8, 18.1, 9.4; IR (neat) 2933, 1724(C═O), 1457, 1403, 1072 cm$^{-1}$; HRMS (EI) calcd for C$_{20}$H$_{30}$O$_4$Na [M]$^+$, required m/z: 357.2036, found m/z: 357.2033.

(1R,4S)-1,2,3,4-tetrahydro-5,6,8-trimethoxy-4,7-dimethyl-1-((S)-6-methylhept-5-en-2-yl)naphthalene (70) was prepared using the following procedure. n-BuLi (n-hexane solution, 0.54 mL, 0.87 mmol, 2.90 equiv) was added dropwise to a solution of isopropyltriphenylphosphonium iodide (389 mg, 0.90 mmol, 3.0 equiv) in dry THF (15 mL) at 0° C. under argon. The mixture was stirred for 1 h at the same temperature. A solution of aldehyde 77 (100 mg, 0.29 mmol) in dry THF (20 mL) was charged into the solution at 0° C., and the resulting solution was stirred for an additional 30 min at the same temperature. The reaction was allowed warm to room temperature for 30 min, and then was refluxed under argon for another 2 h. After cooled down, the reaction mixture was quenched with saturated aqueous NH$_4$Cl and extracted with ether. The organic layer was washed with brine and dried over Na$_2$SO$_4$, and concentrated in vacuo. Purification by column chromatography on silica gel (eluting with 2% ether/pentane) gave 70 (86 mg, 80%). [α]$^{25}_D$=6.4° (c=1.0, CHCl$_3$); $^1$H NMR (500 MHz, CDCl$_3$) δ 5.13 (t, J=7.0 Hz, 1H), 3.85 (s, 3H), 3.81 (s, 3H), 3.65 (s, 3H), 3.15 (m, 1H), 2.88 (m, 1H), 2.18 (s, 3H), 1.91-2.07 (m, 4H), 1.79 (m, 2H), 1.69 (s, 3H), 1.60 (s, 3H), 1.45 (m, 1H), 1.22-1.38 (m, 2H), 1.14 (d, J=7.5 Hz, 3H), 0.72 (d, J=7.0 Hz, 3H); $^{13}$C NMR (75 MHz, CDCl$_3$) δ 153.0, 149.5, 147.0, 134.9, 130.8, 128.7, 125.3, 122.2, 60.5, 60.1, 59.9, 37.5, 35.74, 35.71, 27.0, 26.7, 26.4, 25.7, 23.2, 18.6, 18.3, 17.6, 9.5; IR (neat) 2930, 1458, 1404, 1074, 1030 cm$^{-1}$; HRMS m/z (EI) calculated for C$_{23}$H$_{36}$O$_3$Na [M]$^+$, required m/z: 383.2557, found 383.2562.

(5R,8S)-5,6,7,8-tetrahydro-4-methoxy-3,8-dimethyl-5-((S)-6-methylhept-5-en-2-yl)naphthalene-1,2-diol (71) was prepared using the following procedure. To a solution of ethanethiol (2.07 g, 33.31 mmol) in dry hexanes (15 mL) at 0° C. under argon was added n-butyllithium (5.20 mL, 8.33 mmol, 1.6 M in hexanes). The mixture was stirred at room temperature for 30 min. Then the mixture was concentrated in vacuo and gave a white powder. The white powder and 70 (100 mg, 0.23 mmol) were dissolved in dry DMF (15 mL) at room temperature and the mixture was heated to reflux (180° C. oil bath) for 3 h. The reaction mixture was allowed to cool down to room temperature, acidified with 5% hydrochloric acid, and extracted with Et$_2$O (2×50 mL). The combined extracts were washed with water and brine, dried over Na$_2$SO$_{41}$ and concentrated. Purification by column chromatography on silica gel (eluting with 13% ether/pentane) gave 71 (76 mg, 85%) as a yellow oil. [α]$^{25}_D$=13.0° (c=0.94, CHCl$_3$) $^1$H NMR (500 MHz, CDCl$_3$) δ 5.13 (t, J=7.0 Hz, 1H), 4.92 (s, 1H), 4.78 (s, 1H), 3.63 (s, 3H), 3.05 (m, 1H), 2.86 (m, 1H), 2.18 (s, 3H), 2.00 (m, 4H), 1.80 (m, 2H), 1.69 (s, 3H), 1.60 (s, 3H), 1.50 (m, 1H), 1.30 (m, 2H), 1.18 (d, J=7.0 Hz, 3H), 0.74 (d, J=7.0 Hz, 3H); $^{13}$C NMR (75 MHz, CDCl$_3$) δ 150.7, 140.1, 136.9, 130.8, 127.3, 125.3, 124.7, 114.9, 60.5 37.6, 35.7, 35.5, 26.7, 26.5 (2C), 25.7, 21.6, 18.8, 18.2, 17.6, 9.2; IR (neat) 3419, 2957, 2927, 1450, 1292, 1093, 1008 cm$^{-1}$; HRMS m/z (EI) calculated for C$_{21}$H$_{32}$O$_3$ [M]$^+$, required m/z: 332.2346, found 332.2346.

(5R,8S)-5,6,7,8-tetrahydro-4-methoxy-3,8-dimethyl-5-((S)-6-methylhept-5-en-2-yl)naphthalene-1,2-dione (72) was prepared using the following procedure. To a solution of diol 71 (76 mg, 0.228 mmol) in 8 mL CH$_3$CN, a solution of cerium ammonium nitrate (376 mg, 0.686 mmol, 3.0 equiv) in distilled waster (8 mL) was added by syringe at 0° C. The resulting red solution was stirred at 0° C. for 10 min. The reaction was quenched with water (10 mL) and extracted with Et$_2$O (2×40 mL). The combined extracts were washed with water and brine, dried over Na$_2$SO$_4$ and concentrated. Purification by column chromatography on silica gel (eluting with 20% ether/pentane) gave 72 (58 mg, 77%) as an orange red oil. [α]$^{25}_D$=271.0° (c=0.0317, CHCl$_3$); $^1$H NMR (500 MHz, CDCl$_3$) δ 5.11 (br t, J=7.0 Hz, 1H), 3.92 (s, 3H), 2.89 (m, 1H), 2.65 (m, 1H), 2.06-1.98 (m, 2H), 1.98 (s, 3H), 1.93-1.88 (m, 1H), 1.86-1.73 (m, 2H), 1.70 (s, 3H), 1.67 (m, 1H), 1.62 (s, 3H), 1.44-1.34 (m, 3H), 1.08 (d, J=7.0 Hz, 3H), 0.85 (d, J=7.0 Hz, 3H); $^{13}$C NMR (125 MHz, CDCl$_3$) δ 181.1, 179.4, 167.7, 150.6, 140.2, 131.5, 124.3, 119.6, 61.2, 37.1, 36.4, 35.6, 26.2, 26.1, 25.8, 25.7, 21.3, 18.5, 17.7, 17.5, 9.7; IR (neat) 2924, 1732, 1673, 1657, 1454, 1376, 1234 cm$^{-1}$; HRMS m/z (EI) calculated for C$_{21}$H$_{30}$O$_3$Na [M]$^+$, required m/z: 353.2078, found 353.2097.

Elisabethadione (63) was prepared using the following procedure. To a solution of ortho quinone 72 (20 mg, 0.06 mmol) in benzene (5 mL) at room temperature under argon was added 4-methylbenzenesulfonic acid monohydrate (23.0 mg, 0.12 mmol, 2.0 equiv). The mixture was stirred at room temperature for 2 h. The reaction was diluted with ether (50 mL), washed with water and brine, dried over Na$_2$SO$_4$, and concentrated. Purification by column chromatography on silica gel (eluting with 2% to 7% ether/pentane) gave elisabethadione (63) (18 mg, 96%) as a yellow oil. [α]$^{25}_D$=278.0° (c=0.58, CHCl$_3$); $^1$H NMR (500 MHz, CDCl$_3$) δ 6.97 (s, OH, 1H), 5.10 (br t, J=7.0 Hz, 1H), 2.95 (m, 1H), 2.89 (m, 1H), 2.10-1.94 (m, 2H), 1.93 (s, 3H), 1.88-1.74 (m, 3H), 1.69 (s, 3H), 1.63 (m, 1H), 1.60 (s, 3H), 1.49-1.43 (m, 1H), 1.35-1.21 (m, 2H), 1.10 (d, J=7.0 Hz, 3H), 0.81 (d, J=7.0 Hz, 3H); $^{13}$C NMR (125 MHz, CDCl$_3$) δ 187.9, 182.9, 150.6, 148.2, 143.1, 131.3, 124.5, 116.8, 36.9, 36.0, 35.7, 26.3, 26.1, 26.0, 25.7, 20.8, 18.1, 17.7, 17.6, 8.2; IR (neat) 3675, 2970, 2920, 1738, 1714, 1406, 1242, 1067 cm$^{-1}$; HRMS m/z (EI) calculated for C$_{20}$H$_{28}$O$_3$ [M]$^+$, required m/z: 316.2033, found 316.2026. $^1$H NMR (500 MHz, benzene) δ 6.73 (s, OH, 1H), 5.25 (m, 1H), 2.93 (m, 1H), 2.83 (m, 1H), 2.20-1.95 (m, 3H), 1.92 (s, 3H), 1.68 (s, 3H), 1.57 (s, 3H), 1.55 (m, 2H), 1.42-1.26 (m, 3H), 1.51 (m, 1H), 0.97 (d, J=7.0 Hz, 3H), 0.71 (d, J=7.0 Hz, 3H).

(1R,4S)-1,2,3,4-tetrahydro-5,6,8-trimethoxy-4,7-dimethyl-1-((S)-pent-4-en-2-yl)naphthalene (73) was prepared using the following procedure (Grieco et al., J. Org. Chem., 41:1485-1486, which is hereby incorporated by reference). To a stirring solution of 65b (95 mg, 0.28 mmol) and o-nitrophenyl selenocyanate (192 mg, 0.85 mmol) in dry THF (7 mL) under argon at room temperature was added tri-n-butylphosphine (212 μL, 0.85 mmol). After stirring for 3 h, the reaction was quenched with ethanol (4 mL) and concentrated. The crude product was used directly for the next step. $^1$H NMR (400 MHz, CDCl$_3$) δ 8.28 (d, J=8.0 Hz, 1H), 7.52 (m, 2H), 7.30 (m, 1H), 3.84 (s, 3H), 3.80 (s, 3H), 3.62 (s, 3H), 3.16 (m, 1H), 2.98-2.83 (m, 3H), 2.17 (s, 3H), 2.10-1.65 (m, 6H), 1.54-1.40 (m, 3H), 1.14 (d, J=6.8 Hz, 3H), 0.76 (d, J=6.8 Hz, 3H) $^{13}$C NMR (75 MHz, CDCl$_3$) δ 152.8, 149.6, 147.1, 146.9, 134.8, 134.1, 133.4, 129.2, 128.2, 126.4, 125.1, 122.2, 60.5, 60.2, 59.9, 37.3, 35.8, 35.5, 27.0, 26.6, 26.5 (2C), 23.2, 18.7, 18.4, 9.4; IR (neat) 2931, 1513, 1330, 1071, 729 cm$^{-1}$; HRMS m/z (EI) calculated for C$_{26}$H$_{35}$NO$_5$Se [M]$^+$, required m/z: 521.1675, found 521.1675.

To a solution of the above crude product in THF (7 mL) was slowly added 30% aqueous hydrogen peroxide (0.35 mL) at 0° C. Stirring was maintained for 1 day at room temperature. Water was added, extracted with ether (twice). The combined organic extracts were washed with water, dried over Na$_2$SO$_4$, and concentrated. The residue was purified by column chromatography on silica gel (eluting with 2% to 5% ether/pentane) to give 73 (80 mg, 90% yield) as colorless oil. $^1$H NMR (500 MHz, CDCl$_3$) δ 5.80 (m, 1H), 5.02-4.95 (m, 2H), 3.85 (s, 3H), 3.80 (s, 3H), 3.63 (s, 3H), 3.16 (m, 1H), 2.86 (m, 1H), 2.17 (s, 3H), 2.10-1.92 (m, 4H), 1.80-1.75 (m, 2H), 1.49-1.45 (m, 1H), 1.14 (d, J=7.0 Hz, 3H), 0.76 (d, J=7.0 Hz, 3H); $^{13}$C NMR (75 MHz, CDCl$_3$) δ 153.0, 149.5, 147.0, 138.9, 134.8, 128.5, 122.2, 114.9, 60.5, 60.1, 59.9, 40.0, 37.8, 35.2, 27.0, 26.5, 23.2, 18.6, 18.1, 9.4; IR (neat) 2956, 1458, 1404, 1072 cm$^{-1}$; HRMS m/z (EI) calculated for C$_{20}$H$_{30}$O$_3$ [M]$^+$, required m/z: 318.2189, found 318.2200.

(5R,8S)-5,6,7,8-tetrahydro-4-methoxy-3,8-dimethyl-5-((S)-pent-4-en-2-yl)naphthalene-1,2-diol (74) was prepared using the following procedure. To a solution of alcohol ethanethiol (0.47 g, 7.54 mmol) in dry hexanes (10 mL) at 0° C. under argon was added n-butyllithium (2.36 mL, 3.77 mmol, 1.6 M in hexanes). The mixture was stirred at room temperature for 30 min. Then the mixture was concentrated in vacuo and gave white powder. The white powder and 73 (60 mg, 0.18 mmol) were dissolved in dry DMF (10 mL) at room temperature, and the mix was heated to reflux (180° C. oil bath) for 3 h. The red brown reaction mixture was allowed to cool down to room temperature, acidified with 5% hydrochloric acid, and extracted with Et$_2$O (2×50 mL). The combined extracts were washed with water and brine, dried over Na$_2$SO$_4$, and concentrated. Purification by column chromatography on silica gel (eluting with 7% to 13% ether/pentane) gave 74 (50 mg, 93%) as a yellow oil. $^1$H NMR (500 MHz, CDCl$_3$) δ 5.80 (m, 1H), 5.02-4.95 (m, 2H), 3.61 (s, 3H), 3.07 (m, 1H), 2.84 (m, 1H), 2.17 (s, 3H), 2.08-1.90 (m, 4H), 1.85-1.72 (m, 2H), 1.51-1.46 (m, 1H), 1.18 (d, J=7.0 Hz, 3H), 0.77 (d, J=7.0 Hz, 3H), OH signals were not observed; $^{13}$C NMR (75 MHz, CDCl$_3$) δ 150.6, 140.2, 139.0, 137.1, 127.3, 124.6, 115.0, 114.9, 60.5, 39.9, 37.8, 35.0, 26.7, 26.2, 21.6, 18.7, 18.0, 9.2; IR (neat) 3437, 2932, 1451, 1294, 1097, 1006, 907 cm$^{-1}$; HRMS m/z (ESI) calculated for C$_{18}$H$_{26}$O$_3$ [M+1]$^+$, required m/z: 291.1955, found 291.1949.

(5R,8S)-5,6,7,8-tetrahydro-4-methoxy-3,8-dimethyl-5-((S)-6-methylhept-5-en-2-yl)naphthalene-1,2-dione (75) was prepared using the following procedure. A solution of diol 14 (50 mg, 0.17 mmol) in 5 mL CH$_3$CN was cooled to 0° C. A solution of cerium ammonium nitrate (254 mg, 0.46 mmol, 2.7 equiv) in distilled water (4 mL) was added by syringe. The reaction mixture was stirred at 0° C. for 5 min. The red reaction mixture was quenched with water (10 mL) and extracted with Et$_2$O (2×40 mL). The combined extracts were washed with water and brine, dried over Na$_2$SO$_4$, and concentrated. Purification by column chromatography on silica gel (eluting 13% ether/pentane) gave 75 (41 mg, 84%) as an orange red oil. $^1$H NMR (500 MHz, benzene-d$_6$) δ 5.68 (m, 1H), 5.02-4.98 (m, 2H), 3.03 (s, 3H), 2.91 (m, 1H), 2.41 (m, 1H), 2.02-1.81 (m, 3H), 1.69 (s, 3H), 1.57-1.48 (m, 1H), 1.44-1.33 (m, 2H), 1.12 (m, 1H), 1.08 (d, J=7.0 Hz, 3H), 0.65 (d, J=7.0 Hz, 3H); $^{13}$C NMR (75 MHz, benzene-d$_6$) δ 180.9, 179.5, 166.4, 149.2, 140.5, 138.0, 121.0, 116.0, 60.2, 40.2, 36.8, 36.4, 26.6, 26.1, 21.4, 18.4, 17.4, 9.5; IR (neat) 2959, 1657, 1643, 1578, 1322, 1232, 983 cm$^{-1}$; HRMS m/z (EI) calculated for C$_{18}$H$_{24}$O$_3$Na [M]$^+$, required m/z: 311.1618, found 311.1614.

(5S,8R)-5,6,7,8-tetrahydro-3-hydroxy-2,5-dimethyl-8-((S)-pent-4-en-2-yl)naphthalene-1,4-dione was prepared using the following procedure. To a solution of ortho quinone 75 (41 mg, 0.14 mmol) in benzene (8 mL) at room temperature under argon was added 4-methylbenzene-sulfonic acid monohydrate (54 mg, 0.28 mmol, 2.0 equiv). The mixture was stirred at room temperature for 2 h. The reaction was diluted with ether (50 mL), washed with water and brine, dried over Na$_2$SO$_4$, and concentrated. Purification by column chromatography on silica gel (eluting with 2% to 5% ether/pentane) gave the title compound (37 mg, 95%) as yellow oil. [α]$^{25}_D$=312° (c=0.64, CHCl$_3$); $^1$H NMR (500 MHz, CDCl$_3$) δ 6.94 (s, OH, 1H) 5.80 (m, 1H), 5.04-4.98 (m, 2H), 2.95 (m, 1H), 2.89 (m, 1H), 2.09-1.89 (m, 3H), 1.93 (s, 3H), 1.88-1.74 (m, 2H), 1.65-1.57 (m, 1H), 1.51-1.45 (m, 1H), 1.10 (d, J=7.0 Hz, 3H), 0.83 (d, J=7.0 Hz, 3H); $^{13}$C NMR (75 MHz, CDCl$_3$) δ 187.9, 182.9, 150.6, 148.1, 143.3, 137.8, 116.9, 115.9, 40.3, 37.0, 35.2, 26.2, 26.0, 20.8, 18.0, 17.6, 8.2; IR (neat) 3383, 2961, 1636, 1340, 1235, 912 cm$^{-1}$; HRMS m/z (EI) calculated for C$_{17}$H$_{22}$O$_3$ [M]$^+$, required m/z: 274.1563, found 274.1564.

Dione (76) was prepared using the following procedure. To a solution of the above para quinone (22 mg, 0.076 mmol) in DCM (3 mL) at 0° C. under argon was added 2,6-lutidine (25 mg, 0.229 mmol, 3.0 equiv) and TBSOTf (24 mg, 0.092 mmol, 1.2 equiv) successively. The mixture was stirred at 0° C. for 30 min. The reaction was quenched with saturated NaHCO$_3$ (4 mL) and extracted with Et$_2$O (2×30 mL). The combined extracts were washed with water and brine, dried over Na$_2$SO$_4$, and concentrated. Purification by column chromatography on silica gel (eluting with pure pentane to 1% ether/pentane) gave 76 (26 mg, 91%) as a yellow oil. $^1$H NMR (500 MHz, CDCl$_3$) δ 5.80 (m, 1H), 5.04-4.97 (m, 2H), 2.94 (m, 1H), 2.84 (m, 1H), 2.09-1.90 (m, 3H), 1.93 (s, 3H), 1.87-1.79 (m, 1H), 1.77-1.71 (m, 1H), 1.63-1.58 (m, 1H), 1.48-1.43 (m, 1H), 1.05 (d, J=7.0 Hz, 3H), 0.97 (s, 9H), 0.82 (d, J=7.0 Hz, 3H), 0.30 (s, 3H), 0.23 (s, 3H); $^{13}$C NMR (75 MHz, CDCl$_3$) δ 188.8, 183.2, 152.3, 145.5, 144.7, 138.0, 124.4, 115.8, 40.3, 36.7, 34.9, 26.2, 26.1, 25.8 (3C), 20.9, 19.0, 18.0, 17.5, 9.0, −3.9, −4.0; IR (neat) 2956, 1658, 1234, 1165, 836 cm$^{-1}$; HRMS m/z (ESI) calculated for C$_{23}$H$_{36}$O$_3$Si [M+1]$^+$, required m/z: 389.2506, found 389.2506.

(+)-p-benzoquinone (64) was prepared using the following procedure. To a solution of terminal olefin 76 (15 mg, 0.038 mmol) in DCM (2 mL) was added 2-methyl-3-buten-2-ol (20 mL, 0.193 mmol, 5.00 equiv.) and Grubbs' second generation catalyst (3.3 mg, 0.0038 mmol, 0.10 equiv.). The red reaction mixture was reflux for 12 h then directly filtered through a pipette column, eluting with 13% ether/pentane to give a yellow oil.

To a solution of the above crude product in THF (4 mL) at 0° C. under argon was added TBAF (38 mL, 0.038 mmol, 1.0 M solution in THF, 1.0 equiv). The yellow solution was turned out to purple immediately. After one minute, the reaction was quenched with saturated H₂O (4 mL) and extracted with Et₂O (2×30 mL). The combined extracts were washed with water and brine, dried over Na₂SO₄, and concentrated. Purification by column chromatography on silica gel (eluting with 13% to 25% ether/pentane) gave 64 (7.7 mg, 60% over two steps) as a yellow oil. $[\alpha]^{25}_D$=270° (c=0.40, CHCl₃); ¹H NMR (500 MHz, CDCl₃) δ 6.95 (s, OH, 1H), 5.62 (m, 2H), 2.95 (br q, J=7.0 Hz, 1H), 2.89 (br t, J=4.5 Hz, 1H), 2.04-1.91 (m, 2H), 1.92 (s, 3H), 1.91-1.79 (m, 2H), 1.78-1.73 (m, 1H), 1.65-1.57 (m, 1H), 1.50-1.45 (m, 1H), 1.30 (s, 6H), 1.10 (d, J=7.0 Hz, 3H), 0.82 (d, J=7.0 Hz, 3H); ¹³C NMR (75 MHz, CDCl₃) δ 187.9, 182.9, 150.7, 148.1, 143.3, 139.6, 126.2, 116.8, 70.6, 38.5, 37.4, 35.3, 29.8, 29.7, 26.2, 26.0, 20.8, 18.2, 17.6, 8.2; HRMS m/z (EI) calculated for $C_{20}H_{28}O_4$ [M]⁺, required m/z: 332.1982, found 332.1982.

Although the invention has been described in detail for the purpose of illustration, it is understood that such detail is solely for that purpose, and variations can be made therein by those skilled in the art without departing from the spirit and scope of the invention which is defined by the claims that are set forth below.

What is claimed is:

1. A method for preparing a compound having the formula:

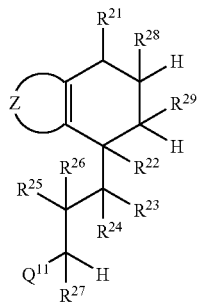

wherein $R^{21}$ is an alkyl group, an aryl group, an alkoxy group, a hydroxy group, an amino group, or a halogen atom; wherein $R^{22}$ is hydrogen atom, an alkyl group, an aryl group, an alkoxy group, or an amino group; wherein $R^{23}$ and $R^{24}$ are independently selected from a hydrogen atom, an alkyl group, an aryl group, an alkoxy group, a hydroxy group, an amino group, and a halogen atom or wherein $R^{23}$ and $R^{24}$, taken together with the carbon atom to which they are bound, form a ring; wherein $R^{25}$ is a hydrogen atom, an alkyl group, an aryl group, an alkoxy group, a hydroxy group, an O-silyl group, or a halogen atom; wherein Z, taken together with the carbons to which it is bonded, forms a six-membered carbon ring; wherein $Q^{11}$ is Y or an alkyl group; wherein each of $R^{26}$ and $R^{27}$ is a hydrogen atom or wherein $R^{26}$ and $R^{27}$, taken together, represent a second bond between the carbon atoms to which $R^{26}$ and $R^{27}$ are bonded; wherein each of $R^{28}$ and $R^{29}$ is a hydrogen atom or wherein $R^{28}$ and $R^{29}$, taken together, represent a second bond between the carbon atoms to which $R^{28}$ and $R^{29}$ are bonded; and wherein Y is an electron withdrawing group, said method comprising:

providing a cyclohexene compound;
providing a vinyldiazo compound; and
contacting the cyclohexene compound with a vinyldiazo compound in the presence of a dirhodium catalyst under conditions effective to produce a compound having the following Formula XXI:

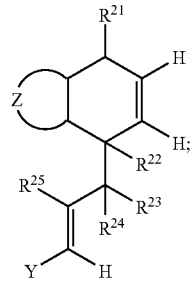

and
optionally treating the compound of Formula XXI with a reducing agent under conditions effective to reduce the ring double bond between the carbons to which Z is not bonded, to reduce the double bond between the carbons to which $R^{25}$ and Y are bonded, and/or to reduce Y.

2. A method according to claim 1, wherein the compound of Formula XXI has the formula:

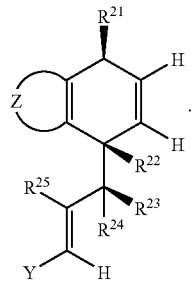

3. A method according to claim 1, wherein the compound of Formula XXI has the formula:

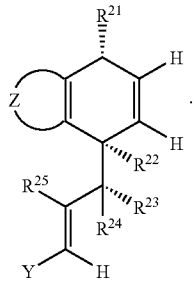

4. A method according to claim 1, wherein $R^{21}$ is a methyl group.

5. A method according to claim 1, wherein $R^{22}$ is a hydrogen atom.

6. A method according to claim 1, wherein $R^{23}$ is a methyl group and wherein $R^{24}$ is a hydrogen atom.

7. A method according to claim 1, wherein $R^{21}$ is a methyl group, wherein $R^{22}$ is a hydrogen atom, wherein $R^{23}$ is a methyl group, and wherein $R^{24}$ is a hydrogen atom.

8. A method according to claim 1, wherein Z, taken together with the carbons to which it is bonded, forms a C6, substituted or unsubstituted, aromatic ring.

9. A method according to claim 8, wherein the compound of Formula XXI has the formula:

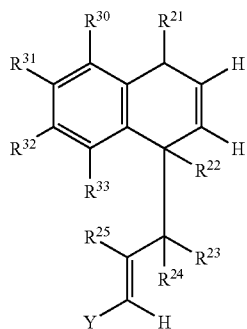

wherein $R^{30}$, $R^{31}$, $R^{32}$, and $R^{33}$ are independently selected from a hydrogen atom, an alkyl group, an aryl group, an alkoxy group, a hydroxy group, a protected hydroxy group; an amino group, a halogen atom, a carboxylic acid group, a carboxylic amide group, carboxylic ester group, a nitro group, a sulfonic acid group, a sulfonamide group, a sulfonic ester group, a keto group, and an aldehyde group; or wherein two of $R^{30}$, $R^{31}$, $R^{32}$ and $R^{33}$, taken together with the carbon atoms to which they are bonded, form a 5-12 membered ring.

10. A method according to claim 9, wherein $R^{30}$, $R^{31}$, $R^{32}$, and $R^{33}$ are independently selected from a hydrogen atom, an alkyl group, an aryl group, and an alkoxy group.

11. A method according to claim 9, wherein $R^{30}$, $R^{31}$, $R^{32}$, and $R^{33}$ are independently selected from a hydrogen atom, an alkyl group, an aryl group, a protected hydroxy group, and an alkoxy group.

12. A method according to claim 9, wherein $R^{30}$, $R^{31}$, $R^{32}$, and $R^{33}$ are independently selected from a hydrogen atom, an alkyl group, an aryl group, an acyloxy group, a silyl ether group, and an alkoxy group.

13. A method according to claim 9, wherein $R^{30}$, $R^{31}$, $R^{32}$, and $R^{33}$ are independently selected from a hydrogen atom, an alkyl group, and an alkoxy group.

14. A method according to claim 9, wherein $R^{30}$, $R^{31}$, $R^{32}$, and $R^{33}$ are independently selected from a hydrogen atom, an alkyl group, a protected hydroxy group, and an alkoxy group.

15. A method according to claim 9, wherein $R^{30}$, $R^{31}$, $R^{32}$, and $R^{33}$ are independently selected from a hydrogen atom, an alkyl group, an acyloxy group, a silyl ether group, and an alkoxy group.

16. A method according to claim 9, wherein each of $R^{21}$ and $R^{23}$ is an alkyl group and wherein each of $R^{22}$, $R^{24}$, and $R^{25}$ are hydrogen atoms.

17. A method according to claim 9, wherein each of $R^{21}$ and $R^{23}$ is a methyl group and wherein each of $R^{22}$, $R^{24}$, and $R^{25}$ are hydrogen atoms.

18. A method according to claim 9, wherein $R^{30}$ is an alkoxy group, wherein $R^{31}$ is an alkoxy group, wherein $R^{32}$ is an alkyl group, and wherein $R^{33}$ is a hydrogen atom.

19. A method according to claim 9, wherein $R^{30}$ is a methoxy group, wherein $R^{31}$ is a methoxy group, wherein $R^{32}$ is a methyl group, and wherein $R^{33}$ is a hydrogen atom.

20. A method according to claim 9, wherein $R^{30}$ is an alkoxy group, wherein $R^{31}$ is an alkoxy group, wherein $R^{32}$ is an alkyl group, and wherein $R^{33}$ is an alkoxy group.

21. A method according to claim 9, wherein $R^{30}$ is a methoxy group, wherein $R^{31}$ is a methoxy group, wherein $R^{32}$ is a methyl group, and wherein $R^{33}$ is a methoxy group.

22. A method according to claim 9, wherein $R^{30}$ is a hydrogen atom, wherein $R^{31}$ is a hydrogen atom, wherein $R^{32}$ is an alkyl group, and wherein $R^{33}$ is a hydrogen atom.

23. A method according to claim 9, wherein $R^{30}$ is a hydrogen atom, wherein $R^{31}$ is a hydrogen atom, wherein $R^{32}$ is a methyl group, and wherein $R^{33}$ is a hydrogen atom.

24. A method according to claim 9, wherein $R^{30}$ is a protected hydroxy group, wherein $R^{31}$ is an alkoxy group, wherein $R^{32}$ is an alkyl group, and wherein $R^{33}$ is a protected hydroxy group.

25. A method according to claim 9, wherein $R^{30}$ is an acyloxy group, wherein $R^{31}$ is a methoxy group, wherein $R^{32}$ is a methyl group, and wherein $R^{33}$ is an acyloxy group.

26. A method according to claim 9, wherein $R^{30}$ is a silyl ether group, wherein $R^{31}$ is a methoxy group, wherein $R^{32}$ is a methyl group, and wherein $R^{33}$ is a silyl ether group.

27. A method according to claim 1, wherein the cyclohexene compound has the formula:

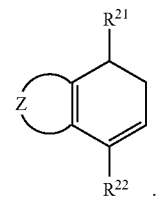

28. A method according to claim 1, wherein the cyclohexene compound has either of the following formulae:

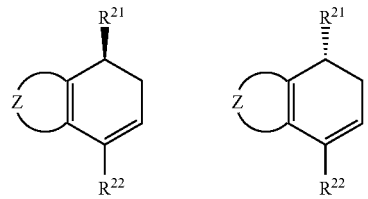

or is a mixture of compounds having such formulae.

29. A method according to claim 1, wherein the cyclohexene compound is a racemic mixture having the formula:

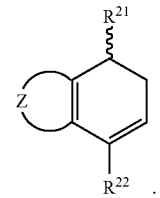

30. A method according to claim 1, wherein the dirhodium catalyst has $D_2$ symmetry.

31. A method according to claim 1, wherein the dirhodium catalyst is a dirhodium tetracarboxylate catalyst.

32. A method according to claim 31, wherein the dirhodium tetracarboxylate catalyst has the formula:

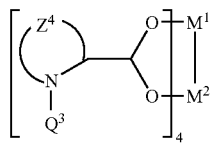

wherein each of $M^1$ and $M^2$ is Rh; $Z^4$ represents the atoms necessary to complete a 3-12 membered heterocyclic ring; and $Q^3$ is an electron withdrawing group.

33. A method according to claim 32, wherein $Z^4$ is a —$CH_2CH_2CH_2$— group and wherein $Q^3$ is a 4-dodecylphenylsulfonyl moiety.

34. A method according to claim 1, wherein the dirhodium catalyst is a dirhodium tetracarboxamidate catalyst.

35. A method according to claim 34, wherein the dirhodium tetracarboxamidate catalyst has the formula:

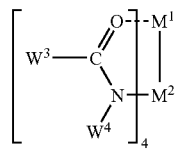

wherein each of $M^1$ and $M^2$ is Rh; wherein $W^3$ represents an alkyl group, an aryl group, an alkoxy group, or an amine group and wherein $W^4$ represents an alkyl group or an aryl group; or wherein $W^3$ and $W^4$, taken together with the atoms to which they are bonded, form a 3-12 membered ring.

* * * * *